US008222000B2

(12) United States Patent
Van Dyk

(10) Patent No.: US 8,222,000 B2
(45) Date of Patent: Jul. 17, 2012

(54) RECOMBINANT BACTERIA HAVING THE ABILITY TO METABOLIZE SUCROSE

(75) Inventor: Tina K. Van Dyk, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/960,634

(22) Filed: Dec. 6, 2010

(65) Prior Publication Data
US 2012/0142064 A1 Jun. 7, 2012

(51) Int. Cl.
*C12P 21/06* (2006.01)

(52) U.S. Cl. .... 435/69.1; 435/141; 435/252; 435/320.1; 435/7.1

(58) Field of Classification Search .................. None
See application file for complete search history.

(56) References Cited

U.S. PATENT DOCUMENTS

| | | | |
|---|---|---|---|
| 6,960,455 B2 | 11/2005 | Livshits et al. | |
| 7,018,794 B2 | 3/2006 | Berka et al. | |
| 7,494,798 B2 * | 2/2009 | Berka et al. | 435/209 |
| 7,863,032 B2 * | 1/2011 | Berka et al. | 435/209 |
| 2007/0015168 A1 | 1/2007 | Bolotine et al. | |
| 2008/0050774 A1 | 2/2008 | Berka et al. | |

FOREIGN PATENT DOCUMENTS

| | | |
|---|---|---|
| WO | WO2009078687 A2 | 6/2009 |
| WO | WO2010051849 A1 | 5/2010 |
| WO | WO2010093182 A2 | 8/2010 |
| WO | WO2010101359 | 9/2010 |
| WO | WO2010101360 | 9/2010 |

OTHER PUBLICATIONS

Olson et al, Production of tyrosine from sucrose or glucose achieved by rapid genetic changes to phenylalanine-producing *Escherichia coli* strains, Appl. Microbiol. Biotechnol., 2007, 1031-1040, 74.

Jahreis et al, Adaptation of Sucrose Metabolism in the *Escherichia coli* Wild-Type Strain EC3132, Journal of Bacteriology, Oct. 2002, 5307-5316, vol. 184, No. 19.

Moniruzzaman et al, Extracellular Melibiose and Fructose Are Intermediates in Raffinose Catabolism during Fermentation to Ethanol by Engineered Enteric Bacteria, Journal of Bacteriology, Mar. 1997, 1880-1886, vol. 179, No. 6.

Lee et al, Development of sucrose-utilizing *Escherichia coli* K-12 strain by cloning β-fructofuranosidases and its application for L-threonine production, Appl. Microbiol. Biotechnol., 2010, 905-913, 88.

* cited by examiner

*Primary Examiner* — Hope Robinson

(57) ABSTRACT

Recombinant bacteria capable of metabolizing sucrose are described. The recombinant bacteria comprise in their genome or on at least one recombinant construct: a nucleotide sequence from *Bacillus licheniformis* ATCC® 14580 encoding a polypeptide having sucrose transporter activity and a nucleotide sequence from *Bacillus licheniformis* ATCC® 14580 encoding a polypeptide having sucrose hydrolase activity. These nucleotide sequences are each operably linked to the same or a different promoter. Recombinant bacteria capable of metabolizing sucrose to produce glycerol and/or glycerol-derived products such as 1,3-propanediol and 3-hydroxypropionic acid are also described.

9 Claims, No Drawings

SEQUENCE LISTING

<160> NUMBER OF SEQ ID NOS: 63

<210> SEQ ID NO 1
<211> LENGTH: 1176
<212> TYPE: DNA
<213> ORGANISM: Saccharomyces cerevisiae

<400> SEQUENCE: 1

```
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac     180
ccagaagttt tcgctccaat agtacaaatg tgggtgttcg aagaagagat caatggtgaa     240
aaattgactg aaatcataaa tactagacat caaaacgtga aatacttgcc tggcatcact     300
ctacccgaca atttggttgc taatccagac ttgattgatt cagtcaagga tgtcgacatc     360
atcgttttca acattccaca tcaattttg ccccgtatct gtagccaatt gaaaggtcat      420
gttgattcac acgtcagagc tatctcctgt ctaaagggtt ttgaagttgg tgctaaaggt     480
gtccaattgc tatcctctta catcactgag gaactaggta ttcaatgtgg tgctctatct     540
ggtgctaaca ttgccaccga agtcgctcaa gaacactggt ctgaaacaac agttgcttac     600
cacattccaa aggatttcag aggcgagggc aaggacgtcg accataaggt tctaaaggcc     660
ttgttccaca gaccttactt ccacgttagt gtcatcgaag atgttgctgg tatctccatc     720
tgtggtgctt tgaagaacgt tgttgcctta ggttgtggtt tcgtcgaagg tctaggctgg     780
ggtaacaacg cttctgctgc catccaaaga gtcggtttgg gtgagatcat cagattcggt     840
```

-continued

```
caaatgtttt tcccagaatc tagagaagaa acatactacc aagagtctgc tggtgttgct    900
gatttgatca ccacctgcgc tggtggtaga acgtcaagg ttgctaggct aatggctact    960
tctggtaagg acgcctggga atgtgaaaag gagttgttga atggccaatc cgctcaaggt   1020
ttaattacct gcaaagaagt tcacgaatgg ttggaaacat gtggctctgt cgaagacttc   1080
ccattatttg aagccgtata ccaaatcgtt tacaacaact acccaatgaa gaacctgccg   1140
gacatgattg aagaattaga tctacatgaa gattag                             1176
```

<210> SEQ ID NO 2
<211> LENGTH: 391
<212> TYPE: PRT
<213> ORGANISM: Saccharomyces cerevisiae

<400> SEQUENCE: 2

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320
```

```
Ser Gly Lys Asp Ala Trp Glu Cys Glu Lys Glu Leu Leu Asn Gly Gln
            325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
            370                 375                 380

Glu Leu Asp Leu His Glu Asp
385                 390

<210> SEQ ID NO 3
<211> LENGTH: 1323
<212> TYPE: DNA
<213> ORGANISM: Saccharomyces cerevisiae

<400> SEQUENCE: 3
atgcttgctg tcagaagatt aacaagatac acattcctta agcgaacgca tccggtgtta      60
tatactcgtc gtgcatataa aattttgcct tcaagatcta ctttcctaag aagatcatta     120
ttacaaacac aactgcactc aaagatgact gctcatacta atatcaaaca gcacaaacac     180
tgtcatgagg accatcctat cagaagatcg gactctgccg tgtcaattgt acatttgaaa     240
cgtgcgccct tcaaggttac agtgattggt tctggtaact gggggaccac catcgccaaa     300
gtcattgcgg aaaacacaga attgcattcc catatcttcg agccagaggt gagaatgtgg     360 gttttttgatg aaaagatcgg cgacgaaaat ctgacggata tcataaatac aagacaccag     420
aacgttaaat atctacccaa tattgacctg ccccataatc tagtggccga tcctgatctt     480
ttacactcca tcaagggtgc tgacatcctt gttttcaaca tccctcatca attttttacca     540 aacatagtca acaattgca aggccacgtg gcccctcatg taagggccat ctcgtgtcta     600
aaagggttcg agttgggctc caagggtgtg caattgctat cctcctatgt tactgatgag     660
ttaggaatcc aatgtggcgc actatctggt gcaaacttgg caccggaagt ggccaaggag     720
cattggtccg aaaccaccgt ggcttaccaa ctaccaaagg attatcaagg tgatggcaag     780
gatgtagatc ataagatttt gaaattgctg ttccacagac cttacttcca cgtcaatgtc     840
atcgatgatg ttgctggtat atccattgcc ggtgccttga gaacgtcgt ggcacttgca     900 tgtggtttcg tagaaggtat gggatggggt aacaatgcct ccgcagccat tcaaaggctg     960
ggtttaggtg aaattatcaa gttcggtaga atgttttttcc cagaatccaa agtcgagacc    1020
tactatcaag aatccgctgg tgttgcagat ctgatcacca cctgctcagg cggtagaaac    1080
gtcaaggttg ccacatacat ggccaagacc ggtaagtcag ccttggaagc agaaaaggaa    1140
ttgcttaacg gtcaatccgc caagggata atcacatgca gagaagttca cgagtggcta    1200
caaacatgtg agttgaccca agaattccca ttattcgagg cagtctacca gatagtctac    1260
aacaacgtcc gcatggaaga cctaccggag atgattgaag agctagacat cgatgacgaa    1320
tag                                                                  1323

<210> SEQ ID NO 4
<211> LENGTH: 440
<212> TYPE: PRT
<213> ORGANISM: Saccharomyces cerevisiae

<400> SEQUENCE: 4

Met Leu Ala Val Arg Arg Leu Thr Arg Tyr Thr Phe Leu Lys Arg Thr
1               5                   10                  15
```

-continued

```
His Pro Val Leu Tyr Thr Arg Arg Ala Tyr Lys Ile Leu Pro Ser Arg
         20                  25                  30

Ser Thr Phe Leu Arg Arg Ser Leu Leu Gln Thr Gln Leu His Ser Lys
             35                  40                  45

Met Thr Ala His Thr Asn Ile Lys Gln His Lys His Cys His Glu Asp
 50                  55                  60

His Pro Ile Arg Arg Ser Asp Ser Ala Val Ser Ile Val His Leu Lys
 65                  70                  75                  80

Arg Ala Pro Phe Lys Val Thr Val Ile Gly Ser Gly Asn Trp Gly Thr
                 85                  90                  95

Thr Ile Ala Lys Val Ile Ala Glu Asn Thr Glu Leu His Ser His Ile
                100                 105                 110

Phe Glu Pro Glu Val Arg Met Trp Val Phe Asp Glu Lys Ile Gly Asp
            115                 120                 125

Glu Asn Leu Thr Asp Ile Ile Asn Thr Arg His Gln Asn Val Lys Tyr
        130                 135                 140

Leu Pro Asn Ile Asp Leu Pro His Asn Leu Val Ala Asp Pro Asp Leu
145                 150                 155                 160

Leu His Ser Ile Lys Gly Ala Asp Ile Leu Val Phe Asn Ile Pro His
                165                 170                 175

Gln Phe Leu Pro Asn Ile Val Lys Gln Leu Gln Gly His Val Ala Pro
            180                 185                 190

His Val Arg Ala Ile Ser Cys Leu Lys Gly Phe Glu Leu Gly Ser Lys
        195                 200                 205

Gly Val Gln Leu Leu Ser Ser Tyr Val Thr Asp Glu Leu Gly Ile Gln
210                 215                 220

Cys Gly Ala Leu Ser Gly Ala Asn Leu Ala Pro Glu Val Ala Lys Glu
225                 230                 235                 240

His Trp Ser Glu Thr Thr Val Ala Tyr Gln Leu Pro Lys Asp Tyr Gln
                245                 250                 255

Gly Asp Gly Lys Asp Val Asp His Lys Ile Leu Lys Leu Leu Phe His
            260                 265                 270

Arg Pro Tyr Phe His Val Asn Val Ile Asp Asp Val Ala Gly Ile Ser
        275                 280                 285

Ile Ala Gly Ala Leu Lys Asn Val Val Ala Leu Ala Cys Gly Phe Val
290                 295                 300

Glu Gly Met Gly Trp Gly Asn Asn Ala Ser Ala Ala Ile Gln Arg Leu
305                 310                 315                 320

Gly Leu Gly Glu Ile Ile Lys Phe Gly Arg Met Phe Phe Pro Glu Ser
                325                 330                 335

Lys Val Glu Thr Tyr Tyr Gln Glu Ser Ala Gly Val Ala Asp Leu Ile
            340                 345                 350

Thr Thr Cys Ser Gly Gly Arg Asn Val Lys Val Ala Thr Tyr Met Ala
        355                 360                 365

Lys Thr Gly Lys Ser Ala Leu Glu Ala Glu Lys Glu Leu Leu Asn Gly
370                 375                 380

Gln Ser Ala Gln Gly Ile Ile Thr Cys Arg Glu Val His Glu Trp Leu
385                 390                 395                 400

Gln Thr Cys Glu Leu Thr Gln Glu Phe Pro Leu Phe Glu Ala Val Tyr
                405                 410                 415

Gln Ile Val Tyr Asn Asn Val Arg Met Glu Asp Leu Pro Glu Met Ile
            420                 425                 430

Glu Glu Leu Asp Ile Asp Asp Glu
435                 440
```

<210> SEQ ID NO 5
<211> LENGTH: 816
<212> TYPE: DNA
<213> ORGANISM: Saccharomyces cerevisiae

<400> SEQUENCE: 5

```
atgaaacgtt tcaatgtttt aaaatatatc agaacaacaa aagcaaatat acaaaccatc    60
gcaatgcctt tgaccacaaa acctttatct ttgaaaatca acgccgctct attcgatgtt   120
gacggtacca tcatcatctc tcaaccagcc attgctgctt tctggagaga tttcggtaaa   180
gacaagcctt acttcgatgc cgaacacgtt attcacatct ctcacggttg agaacttac   240
gatgccattg ccaagttcgc tccagacttt gctgatgaag aatacgttaa caagctagaa   300
ggtgaaatcc cagaaaagta cggtgaacac tccatcgaag ttccaggtgc tgtcaagttg   360
tgtaatgctt tgaacgcctt gccaaaggaa aaatgggctg tcgccacctc tggtacccgt   420
gacatggcca gaaatggtt cgacattttg aagatcaaga accagaata cttcatcacc   480
gccaatgatg tcaagcaagg taagcctcac ccagaaccat acttaaaggg tagaaacggt   540
ttgggtttcc caattaatga acaagaccca tccaaatcta aggttgttgt ctttgaagac   600
gcaccagctg gtattgctgc tggtaaggct gctggctgta aaatcgttgg tattgctacc   660
actttcgatt ggacttctt gaaggaaaag ggttgtgaca tcattgtcaa gaaccacgaa   720
tctatcagag tcggtgaata caacgctgaa accgatgaag tcgaattgat ctttgatgac   780
tacttatacg ctaaggatga cttgttgaaa tggtaa                            816
```

<210> SEQ ID NO 6
<211> LENGTH: 271
<212> TYPE: PRT
<213> ORGANISM: Saccharomyces cerevisiae

<400> SEQUENCE: 6

```
Met Lys Arg Phe Asn Val Leu Lys Tyr Ile Arg Thr Thr Lys Ala Asn
1               5                   10                  15

Ile Gln Thr Ile Ala Met Pro Leu Thr Thr Lys Pro Leu Ser Leu Lys
            20                  25                  30

Ile Asn Ala Ala Leu Phe Asp Val Asp Gly Thr Ile Ile Ser Gln
        35                  40                  45

Pro Ala Ile Ala Ala Phe Trp Arg Asp Phe Gly Lys Asp Lys Pro Tyr
    50                  55                  60

Phe Asp Ala Glu His Val Ile His Ile Ser His Gly Trp Arg Thr Tyr
65                  70                  75                  80

Asp Ala Ile Ala Lys Phe Ala Pro Asp Phe Ala Asp Glu Glu Tyr Val
                85                  90                  95

Asn Lys Leu Glu Gly Glu Ile Pro Glu Lys Tyr Gly Glu His Ser Ile
            100                 105                 110

Glu Val Pro Gly Ala Val Lys Leu Cys Asn Ala Leu Asn Ala Leu Pro
        115                 120                 125

Lys Glu Lys Trp Ala Val Ala Thr Ser Gly Thr Arg Asp Met Ala Lys
    130                 135                 140

Lys Trp Phe Asp Ile Leu Lys Ile Lys Arg Pro Glu Tyr Phe Ile Thr
145                 150                 155                 160

Ala Asn Asp Val Lys Gln Gly Lys Pro His Pro Glu Pro Tyr Leu Lys
                165                 170                 175

Gly Arg Asn Gly Leu Gly Phe Pro Ile Asn Glu Gln Asp Pro Ser Lys
            180                 185                 190
```

Ser Lys Val Val Phe Glu Asp Ala Pro Ala Gly Ile Ala Ala Gly
        195                 200                 205

Lys Ala Ala Gly Cys Lys Ile Val Gly Ile Ala Thr Thr Phe Asp Leu
        210                 215                 220

Asp Phe Leu Lys Glu Lys Gly Cys Asp Ile Val Lys Asn His Glu
225                 230                 235                 240

Ser Ile Arg Val Gly Glu Tyr Asn Ala Glu Thr Asp Glu Val Glu Leu
                245                 250                 255

Ile Phe Asp Asp Tyr Leu Tyr Ala Lys Asp Leu Leu Lys Trp
                260                 265                 270

<210> SEQ ID NO 7
<211> LENGTH: 753
<212> TYPE: DNA
<213> ORGANISM: Saccharomyces cerevisiae

<400> SEQUENCE: 7

```
atgggattga ctactaaacc tctatctttg aaagttaacg ccgctttgtt cgacgtcgac      60
ggtaccatta tcatctctca accagccatt gctgcattct ggagggattt cggtaaggac     120
aaaccttatt tcgatgctga acacgttatc caagtctcgc atggttggag aacgtttgat     180
gccattgcta agttcgctcc agactttgcc aatgaagagt atgttaacaa attagaagct     240
gaaattccgg tcaagtacgg tgaaaaatcc attgaagtcc aggtgcagt taagctgtgc      300
aacgctttga cgctctacc aaaagagaaa tgggctgtgg caacttccgg tacccgtgat      360
atggcacaaa atggttcga gcatctggga atcaggagac caaagtactt cattaccgct      420
aatgatgtca acagggtaa gcctcatcca gaaccatatc tgaagggcag gaatggctta      480
ggatatccga tcaatgagca agacccttcc aaatctaagg tagtagtatt tgaagacgct      540
ccagcaggta ttgccgccgg aaaagccgcc ggttgtaaga tcattggtat tgccactact      600
ttcgacttgg acttcctaaa ggaaaaaggc tgtgacatca ttgtcaaaaa ccacgaatcc      660
atcagagttg cggctacaa tgccgaaaca gacgaagttg aattcatttt tgacgactac      720
ttatatgcta aggacgatct gttgaaatgg taa                                   753
```

<210> SEQ ID NO 8
<211> LENGTH: 250
<212> TYPE: PRT
<213> ORGANISM: Saccharomyces cerevisiae

<400> SEQUENCE: 8

Met Gly Leu Thr Thr Lys Pro Leu Ser Leu Lys Val Asn Ala Ala Leu
1               5                   10                  15

Phe Asp Val Asp Gly Thr Ile Ile Ile Ser Gln Pro Ala Ile Ala Ala
                20                  25                  30

Phe Trp Arg Asp Phe Gly Lys Asp Lys Pro Tyr Phe Asp Ala Glu His
        35                  40                  45

Val Ile Gln Val Ser His Gly Trp Arg Thr Phe Asp Ala Ile Ala Lys
    50                  55                  60

Phe Ala Pro Asp Phe Ala Asn Glu Glu Tyr Val Asn Lys Leu Glu Ala
65                  70                  75                  80

Glu Ile Pro Val Lys Tyr Gly Glu Lys Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Gln Lys Trp Phe Glu His

-continued

```
                 115                 120                 125
Leu Gly Ile Arg Arg Pro Lys Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Ile Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
    210                 215                 220

Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
                245                 250

<210> SEQ ID NO 9
<211> LENGTH: 1668
<212> TYPE: DNA
<213> ORGANISM: Klebsiella pneumoniae
<220> FEATURE:
<221> NAME/KEY: CDS
<222> LOCATION: (1)..(1668)

<400> SEQUENCE: 9 atg aaa aga tca aaa cga ttt gca gta ctg gcc cag cgc ccc gtc aat      48
Met Lys Arg Ser Lys Arg Phe Ala Val Leu Ala Gln Arg Pro Val Asn
1               5                   10                  15 cag gac ggg ctg att ggc gag tgg cct gaa gag ggg ctg atc gcc atg      96
Gln Asp Gly Leu Ile Gly Glu Trp Pro Glu Glu Gly Leu Ile Ala Met
            20                  25                  30 gac agc ccc ttt gac ccg gtc tct tca gta aaa gtg gac aac ggt ctg     144
Asp Ser Pro Phe Asp Pro Val Ser Ser Val Lys Val Asp Asn Gly Leu
        35                  40                  45 atc gtc gaa ctg gac ggc aaa cgc cgg gac cag ttt gac atg atc gac     192
Ile Val Glu Leu Asp Gly Lys Arg Arg Asp Gln Phe Asp Met Ile Asp
    50                  55                  60 cga ttt atc gcc gat tac gcg atc aac gtt gag cgc aca gag cag gca     240
Arg Phe Ile Ala Asp Tyr Ala Ile Asn Val Glu Arg Thr Glu Gln Ala
65                  70                  75                  80 atg cgc ctg gag gcg gtg gaa ata gcc cgt atg ctg gtg gat att cac     288
Met Arg Leu Glu Ala Val Glu Ile Ala Arg Met Leu Val Asp Ile His
            85                  90                  95 gtc agc cgg gag gag atc att gcc atc act acc gcc atc acg ccg gcc     336
Val Ser Arg Glu Glu Ile Ile Ala Ile Thr Thr Ala Ile Thr Pro Ala
        100                 105                 110 aaa gcg gtc gag gtg atg gcg cag atg aac gtg gtg gag atg atg atg     384
Lys Ala Val Glu Val Met Ala Gln Met Asn Val Val Glu Met Met Met
    115                 120                 125 gcg ctg cag aag atg cgt gcc cgc cgg acc ccc tcc aac cag tgc cac     432
Ala Leu Gln Lys Met Arg Ala Arg Arg Thr Pro Ser Asn Gln Cys His
130                 135                 140 gtc acc aat ctc aaa gat aat ccg gtg cag att gcc gct gac gcc gcc     480
Val Thr Asn Leu Lys Asp Asn Pro Val Gln Ile Ala Ala Asp Ala Ala
145                 150                 155                 160 gag gcc ggg atc cgc ggc ttc tca gaa cag gag acc acg gtc ggt atc     528
Glu Ala Gly Ile Arg Gly Phe Ser Glu Gln Glu Thr Thr Val Gly Ile
            165                 170                 175
```

| | | |
|---|---|---|
| gcg cgc tac gcg ccg ttt aac gcc ctg gcg ctg ttg gtc ggt tcg cag<br>Ala Arg Tyr Ala Pro Phe Asn Ala Leu Ala Leu Leu Val Gly Ser Gln<br>180 185 190 | | 576 |
| tgc ggc cgc ccc ggc gtg ttg acg cag tgc tcg gtg gaa gag gcc acc<br>Cys Gly Arg Pro Gly Val Leu Thr Gln Cys Ser Val Glu Glu Ala Thr<br>195 200 205 | | 624 |
| gag ctg gag ctg ggc atg cgt ggc tta acc agc tac gcc gag acg gtg<br>Glu Leu Glu Leu Gly Met Arg Gly Leu Thr Ser Tyr Ala Glu Thr Val<br>210 215 220 | | 672 |
| tcg gtc tac ggc acc gaa gcg gta ttt acc gac ggc gat gat acg ccg<br>Ser Val Tyr Gly Thr Glu Ala Val Phe Thr Asp Gly Asp Asp Thr Pro<br>225 230 235 240 | | 720 |
| tgg tca aag gcg ttc ctc gcc tcg gcc tac gcc tcc cgc ggg ttg aaa<br>Trp Ser Lys Ala Phe Leu Ala Ser Ala Tyr Ala Ser Arg Gly Leu Lys<br>245 250 255 | | 768 |
| atg cgc tac acc tcc ggc acc gga tcc gaa gcg ctg atg ggc tat tcg<br>Met Arg Tyr Thr Ser Gly Thr Gly Ser Glu Ala Leu Met Gly Tyr Ser<br>260 265 270 | | 816 |
| gag agc aag tcg atg ctc tac ctc gaa tcg cgc tgc atc ttc att act<br>Glu Ser Lys Ser Met Leu Tyr Leu Glu Ser Arg Cys Ile Phe Ile Thr<br>275 280 285 | | 864 |
| aaa ggc gcc ggg gtt cag gga ctg caa aac ggc gcg gtg agc tgt atc<br>Lys Gly Ala Gly Val Gln Gly Leu Gln Asn Gly Ala Val Ser Cys Ile<br>290 295 300 | | 912 |
| ggc atg acc ggc gct gtg ccg tcg ggc att cgg gcg gtg ctg gcg gaa<br>Gly Met Thr Gly Ala Val Pro Ser Gly Ile Arg Ala Val Leu Ala Glu<br>305 310 315 320 | | 960 |
| aac ctg atc gcc tct atg ctc gac ctc gaa gtg gcg tcc gcc aac gac<br>Asn Leu Ile Ala Ser Met Leu Asp Leu Glu Val Ala Ser Ala Asn Asp<br>325 330 335 | | 1008 |
| cag act ttc tcc cac tcg gat att cgc cgc acc gcg cgc acc ctg atg<br>Gln Thr Phe Ser His Ser Asp Ile Arg Arg Thr Ala Arg Thr Leu Met<br>340 345 350 | | 1056 |
| cag atg ctg ccg ggc acc gac ttt att ttc tcc ggc tac agc gcg gtg<br>Gln Met Leu Pro Gly Thr Asp Phe Ile Phe Ser Gly Tyr Ser Ala Val<br>355 360 365 | | 1104 |
| ccg aac tac gac aac atg ttc gcc ggc tcg aac ttc gat gcg gaa gat<br>Pro Asn Tyr Asp Asn Met Phe Ala Gly Ser Asn Phe Asp Ala Glu Asp<br>370 375 380 | | 1152 |
| ttt gat gat tac aac atc ctg cag cgt gac ctg atg gtt gac ggc ggc<br>Phe Asp Asp Tyr Asn Ile Leu Gln Arg Asp Leu Met Val Asp Gly Gly<br>385 390 395 400 | | 1200 |
| ctg cgt ccg gtg acc gag gcg gaa acc att gcc att cgc cag aaa gcg<br>Leu Arg Pro Val Thr Glu Ala Glu Thr Ile Ala Ile Arg Gln Lys Ala<br>405 410 415 | | 1248 |
| gcg cgg gcg atc cag gcg gtt ttc cgc gag ctg ggg ctg ccg cca atc<br>Ala Arg Ala Ile Gln Ala Val Phe Arg Glu Leu Gly Leu Pro Pro Ile<br>420 425 430 | | 1296 |
| gcc gac gag gag gtg gag gcc gcc acc tac gcg cac ggc agc aac gag<br>Ala Asp Glu Glu Val Glu Ala Ala Thr Tyr Ala His Gly Ser Asn Glu<br>435 440 445 | | 1344 |
| atg ccg ccg cgt aac gtg gtg gag gat ctg agt gcg gtg gaa gag atg<br>Met Pro Pro Arg Asn Val Val Glu Asp Leu Ser Ala Val Glu Glu Met<br>450 455 460 | | 1392 |
| atg aag cgc aac atc acc ggc ctc gat att gtc ggc gcg ctg agc cgc<br>Met Lys Arg Asn Ile Thr Gly Leu Asp Ile Val Gly Ala Leu Ser Arg<br>465 470 475 480 | | 1440 |
| agc ggc ttt gag gat atc gcc agc aat att ctc aat atg ctg cgc cag<br>Ser Gly Phe Glu Asp Ile Ala Ser Asn Ile Leu Asn Met Leu Arg Gln<br>485 490 495 | | 1488 |

-continued

```
cgg gtc acc ggc gat tac ctg cag acc tcg gcc att ctc gat cgg cag      1536
Arg Val Thr Gly Asp Tyr Leu Gln Thr Ser Ala Ile Leu Asp Arg Gln
        500                 505                 510 ttc gag gtg gtg agt gcg gtc aac gac atc aat gac tat cag ggg ccg      1584
Phe Glu Val Val Ser Ala Val Asn Asp Ile Asn Asp Tyr Gln Gly Pro
    515                 520                 525 ggc acc ggc tat cgc atc tct gcc gaa cgc tgg gcg gag atc aaa aat      1632
Gly Thr Gly Tyr Arg Ile Ser Ala Glu Arg Trp Ala Glu Ile Lys Asn
530                 535                 540 att ccg ggc gtg gtt cag ccc gac acc att gaa taa                       1668
Ile Pro Gly Val Val Gln Pro Asp Thr Ile Glu
545                 550                 555
```

<210> SEQ ID NO 10
<211> LENGTH: 555
<212> TYPE: PRT
<213> ORGANISM: Klebsiella pneumoniae

<400> SEQUENCE: 10

```
Met Lys Arg Ser Lys Arg Phe Ala Val Leu Ala Gln Arg Pro Val Asn
1               5                   10                  15

Gln Asp Gly Leu Ile Gly Glu Trp Pro Glu Gly Leu Ile Ala Met
            20                  25                  30

Asp Ser Pro Phe Asp Pro Val Ser Ser Val Lys Val Asp Asn Gly Leu
        35                  40                  45

Ile Val Glu Leu Asp Gly Lys Arg Arg Asp Gln Phe Asp Met Ile Asp
    50                  55                  60

Arg Phe Ile Ala Asp Tyr Ala Ile Asn Val Glu Arg Thr Glu Gln Ala
65                  70                  75                  80

Met Arg Leu Glu Ala Val Glu Ile Ala Arg Met Leu Val Asp Ile His
                85                  90                  95

Val Ser Arg Glu Glu Ile Ile Ala Ile Thr Thr Ala Ile Thr Pro Ala
            100                 105                 110

Lys Ala Val Glu Val Met Ala Gln Met Asn Val Val Glu Met Met Met
        115                 120                 125

Ala Leu Gln Lys Met Arg Ala Arg Arg Thr Pro Ser Asn Gln Cys His
    130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Glu Thr Thr Val Gly Ile
                165                 170                 175

Ala Arg Tyr Ala Pro Phe Asn Ala Leu Ala Leu Leu Val Gly Ser Gln
            180                 185                 190

Cys Gly Arg Pro Gly Val Leu Thr Gln Cys Ser Val Glu Glu Ala Thr
        195                 200                 205

Glu Leu Glu Leu Gly Met Arg Gly Leu Thr Ser Tyr Ala Glu Thr Val
    210                 215                 220

Ser Val Tyr Gly Thr Glu Ala Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255

Met Arg Tyr Thr Ser Gly Thr Gly Ser Glu Ala Leu Met Gly Tyr Ser
            260                 265                 270

Glu Ser Lys Ser Met Leu Tyr Leu Glu Ser Arg Cys Ile Phe Ile Thr
        275                 280                 285

Lys Gly Ala Gly Val Gln Gly Leu Gln Asn Gly Ala Val Ser Cys Ile
```

```
                    290                 295                 300
Gly Met Thr Gly Ala Val Pro Ser Gly Ile Arg Ala Val Leu Ala Glu
305                 310                 315                 320

Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
            340                 345                 350

Gln Met Leu Pro Gly Thr Asp Phe Ile Phe Ser Gly Tyr Ser Ala Val
                355                 360                 365

Pro Asn Tyr Asp Asn Met Phe Ala Gly Ser Asn Phe Asp Ala Glu Asp
        370                 375                 380

Phe Asp Asp Tyr Asn Ile Leu Gln Arg Asp Leu Met Val Asp Gly Gly
385                 390                 395                 400

Leu Arg Pro Val Thr Glu Ala Glu Thr Ile Ala Ile Arg Gln Lys Ala
                405                 410                 415

Ala Arg Ala Ile Gln Ala Val Phe Arg Glu Leu Gly Leu Pro Pro Ile
            420                 425                 430

Ala Asp Glu Glu Val Glu Ala Ala Thr Tyr Ala His Gly Ser Asn Glu
        435                 440                 445

Met Pro Pro Arg Asn Val Val Glu Asp Leu Ser Ala Val Glu Glu Met
450                 455                 460

Met Lys Arg Asn Ile Thr Gly Leu Asp Ile Val Gly Ala Leu Ser Arg
465                 470                 475                 480

Ser Gly Phe Glu Asp Ile Ala Ser Asn Ile Leu Asn Met Leu Arg Gln
                485                 490                 495

Arg Val Thr Gly Asp Tyr Leu Gln Thr Ser Ala Ile Leu Asp Arg Gln
            500                 505                 510

Phe Glu Val Val Ser Ala Val Asn Asp Ile Asn Asp Tyr Gln Gly Pro
        515                 520                 525

Gly Thr Gly Tyr Arg Ile Ser Ala Glu Arg Trp Ala Glu Ile Lys Asn
    530                 535                 540

Ile Pro Gly Val Val Gln Pro Asp Thr Ile Glu
545                 550                 555

<210> SEQ ID NO 11
<211> LENGTH: 585
<212> TYPE: DNA
<213> ORGANISM: Klebsiella pneumoniae
<220> FEATURE:
<221> NAME/KEY: CDS
<222> LOCATION: (1)..(585)

<400> SEQUENCE: 11 gtg caa cag aca acc caa att cag ccc tct ttt acc ctg aaa acc cgc     48
Val Gln Gln Thr Thr Gln Ile Gln Pro Ser Phe Thr Leu Lys Thr Arg
1               5                   10                  15 gag ggc ggg gta gct tct gcc gat gaa cgc gcc gat gaa gtg gtg atc     96
Glu Gly Gly Val Ala Ser Ala Asp Glu Arg Ala Asp Glu Val Val Ile
            20                  25                  30 ggc gtc ggc cct gcc ttc gat aaa cac cag cat cac act ctg atc gat    144
Gly Val Gly Pro Ala Phe Asp Lys His Gln His His Thr Leu Ile Asp
        35                  40                  45 atg ccc cat ggc gcg atc ctc aaa gag ctg att gcc ggg gtg gaa gaa    192
Met Pro His Gly Ala Ile Leu Lys Glu Leu Ile Ala Gly Val Glu Glu
    50                  55                  60 gag ggg ctt cac gcc cgg gtg gtg cgc att ctg cgc acg tcc gac gtc    240
Glu Gly Leu His Ala Arg Val Val Arg Ile Leu Arg Thr Ser Asp Val
65                  70                  75                  80
```

```
tcc ttt atg gcc tgg gat gcg gcc aac ctg agc ggc tcg ggg atc ggc    288
Ser Phe Met Ala Trp Asp Ala Ala Asn Leu Ser Gly Ser Gly Ile Gly
            85                  90                  95 atc ggt atc cag tcg aag ggg acc acg gtc atc cat cag cgc gat ctg    336
Ile Gly Ile Gln Ser Lys Gly Thr Thr Val Ile His Gln Arg Asp Leu
        100                 105                 110 ctg ccg ctc agc aac ctg gag ctg ttc tcc cag gcg ccg ctg ctg acg    384
Leu Pro Leu Ser Asn Leu Glu Leu Phe Ser Gln Ala Pro Leu Leu Thr
    115                 120                 125 ctg gag acc tac cgg cag att ggc aaa aac gct gcg cgc tat gcg cgc    432
Leu Glu Thr Tyr Arg Gln Ile Gly Lys Asn Ala Ala Arg Tyr Ala Arg
130                 135                 140 aaa gag tca cct tcg ccg gtg ccg gtg gtg aac gat cag atg gtg cgg    480
Lys Glu Ser Pro Ser Pro Val Pro Val Val Asn Asp Gln Met Val Arg
145                 150                 155                 160 ccg aaa ttt atg gcc aaa gcc gcg cta ttt cat atc aaa gag acc aaa    528
Pro Lys Phe Met Ala Lys Ala Ala Leu Phe His Ile Lys Glu Thr Lys
                165                 170                 175 cat gtg gtg cag gac gcc gag ccc gtc acc ctg cac atc gac tta gta    576
His Val Val Gln Asp Ala Glu Pro Val Thr Leu His Ile Asp Leu Val
            180                 185                 190 agg gag tga                                                         585
Arg Glu

<210> SEQ ID NO 12
<211> LENGTH: 194
<212> TYPE: PRT
<213> ORGANISM: Klebsiella pneumoniae

<400> SEQUENCE: 12

Val Gln Gln Thr Thr Gln Ile Gln Pro Ser Phe Thr Leu Lys Thr Arg
1               5                   10                  15

Glu Gly Gly Val Ala Ser Ala Asp Glu Arg Ala Asp Glu Val Val Ile
            20                  25                  30

Gly Val Gly Pro Ala Phe Asp Lys His Gln His His Thr Leu Ile Asp
        35                  40                  45

Met Pro His Gly Ala Ile Leu Lys Glu Leu Ile Ala Gly Val Glu Glu
    50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
    130                 135                 140

Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Gln Asp Ala Glu Pro Val Thr Leu His Ile Asp Leu Val
            180                 185                 190

Arg Glu

<210> SEQ ID NO 13
```

```
<211> LENGTH: 426
<212> TYPE: DNA
<213> ORGANISM: Klebsiella pneumoniae
<220> FEATURE:
<221> NAME/KEY: CDS
<222> LOCATION: (1)..(426)

<400> SEQUENCE: 13 atg agc gag aaa acc atg cgc gtg cag gat tat ccg tta gcc acc cgc      48
Met Ser Glu Lys Thr Met Arg Val Gln Asp Tyr Pro Leu Ala Thr Arg
1               5                   10                  15 tgc ccg gag cat atc ctg acg cct acc ggc aaa cca ttg acc gat att      96
Cys Pro Glu His Ile Leu Thr Pro Thr Gly Lys Pro Leu Thr Asp Ile
                20                  25                  30 acc ctc gag aag gtg ctc tct ggc gag gtg ggc ccg cag gat gtg cgg     144
Thr Leu Glu Lys Val Leu Ser Gly Glu Val Gly Pro Gln Asp Val Arg
            35                  40                  45 atc tcc cgc cag acc ctt gag tac cag gcg cag att gcc gag cag atg     192
Ile Ser Arg Gln Thr Leu Glu Tyr Gln Ala Gln Ile Ala Glu Gln Met
    50                  55                  60 cag cgc cat gcg gtg gcg cgc aat ttc cgc cgc gcg gcg gag ctt atc     240
Gln Arg His Ala Val Ala Arg Asn Phe Arg Arg Ala Ala Glu Leu Ile
65                  70                  75                  80 gcc att cct gac gag cgc att ctg gct atc tat aac gcg ctg cgc ccg     288
Ala Ile Pro Asp Glu Arg Ile Leu Ala Ile Tyr Asn Ala Leu Arg Pro
                85                  90                  95 ttc cgc tcc tcg cag gcg gag ctg ctg gcg atc gcc gac gag ctg gag     336
Phe Arg Ser Ser Gln Ala Glu Leu Leu Ala Ile Ala Asp Glu Leu Glu
                100                 105                 110 cac acc tgg cat gcg aca gtg aat gcc gcc ttt gtc cgg gag tcg gcg     384
His Thr Trp His Ala Thr Val Asn Ala Ala Phe Val Arg Glu Ser Ala
            115                 120                 125 gaa gtg tat cag cag cgg cat aag ctg cgt aaa gga agc taa             426
Glu Val Tyr Gln Gln Arg His Lys Leu Arg Lys Gly Ser
    130                 135                 140

<210> SEQ ID NO 14
<211> LENGTH: 141
<212> TYPE: PRT
<213> ORGANISM: Klebsiella pneumoniae

<400> SEQUENCE: 14

Met Ser Glu Lys Thr Met Arg Val Gln Asp Tyr Pro Leu Ala Thr Arg
1               5                   10                  15

Cys Pro Glu His Ile Leu Thr Pro Thr Gly Lys Pro Leu Thr Asp Ile
                20                  25                  30

Thr Leu Glu Lys Val Leu Ser Gly Glu Val Gly Pro Gln Asp Val Arg
            35                  40                  45

Ile Ser Arg Gln Thr Leu Glu Tyr Gln Ala Gln Ile Ala Glu Gln Met
    50                  55                  60

Gln Arg His Ala Val Ala Arg Asn Phe Arg Arg Ala Ala Glu Leu Ile
65                  70                  75                  80

Ala Ile Pro Asp Glu Arg Ile Leu Ala Ile Tyr Asn Ala Leu Arg Pro
                85                  90                  95

Phe Arg Ser Ser Gln Ala Glu Leu Leu Ala Ile Ala Asp Glu Leu Glu
                100                 105                 110

His Thr Trp His Ala Thr Val Asn Ala Ala Phe Val Arg Glu Ser Ala
            115                 120                 125

Glu Val Tyr Gln Gln Arg His Lys Leu Arg Lys Gly Ser
    130                 135                 140
```

<210> SEQ ID NO 15
<211> LENGTH: 1539
<212> TYPE: DNA
<213> ORGANISM: Escherichia coli
<220> FEATURE:
<221> NAME/KEY: CDS
<222> LOCATION: (1)..(1539)

<400> SEQUENCE: 15

| | | |
|---|---|---|
| atg acc aat aat ccc cct tca gca cag att aag ccc ggc gag tat ggt<br>Met Thr Asn Asn Pro Pro Ser Ala Gln Ile Lys Pro Gly Glu Tyr Gly<br>1               5                   10                  15 | | 48 |
| ttc ccc ctc aag tta aaa gcc cgc tat gac aac ttt att ggc ggc gaa<br>Phe Pro Leu Lys Leu Lys Ala Arg Tyr Asp Asn Phe Ile Gly Gly Glu<br>            20                  25                  30 | | 96 |
| tgg gta gcc cct gcc gac ggc gag tat tac cag aat ctg acg ccg gtg<br>Trp Val Ala Pro Ala Asp Gly Glu Tyr Tyr Gln Asn Leu Thr Pro Val<br>        35                  40                  45 | | 144 |
| acc ggg cag ctg ctg tgc gaa gtg gcg tct tcg ggc aaa cga gac atc<br>Thr Gly Gln Leu Leu Cys Glu Val Ala Ser Ser Gly Lys Arg Asp Ile<br>    50                  55                  60 | | 192 |
| gat ctg gcg ctg gat gct gcg cac aaa gtg aaa gat aaa tgg gcg cac<br>Asp Leu Ala Leu Asp Ala Ala His Lys Val Lys Asp Lys Trp Ala His<br>65                  70                  75                  80 | | 240 |
| acc tcg gtg cag gat cgt gcg gcg att ctg ttt aag att gcc gat cga<br>Thr Ser Val Gln Asp Arg Ala Ala Ile Leu Phe Lys Ile Ala Asp Arg<br>                85                  90                  95 | | 288 |
| atg gaa caa aac ctc gag ctg tta gcg aca gct gaa acc tgg gat aac<br>Met Glu Gln Asn Leu Glu Leu Leu Ala Thr Ala Glu Thr Trp Asp Asn<br>            100                 105                 110 | | 336 |
| ggc aaa ccc att cgc gaa acc agt gct gcg gat gta ccg ctg gcg att<br>Gly Lys Pro Ile Arg Glu Thr Ser Ala Ala Asp Val Pro Leu Ala Ile<br>        115                 120                 125 | | 384 |
| gac cat ttc cgc tat ttc gcc tcg tgt att cgg gcg cag gaa ggt ggg<br>Asp His Phe Arg Tyr Phe Ala Ser Cys Ile Arg Ala Gln Glu Gly Gly<br>    130                 135                 140 | | 432 |
| atc agt gaa gtt gat agc gaa acc gtg gcc tat cat ttc cat gaa ccg<br>Ile Ser Glu Val Asp Ser Glu Thr Val Ala Tyr His Phe His Glu Pro<br>145                 150                 155                 160 | | 480 |
| tta ggc gtg gtg ggg cag att atc ccg tgg aac ttc ccg ctg ctg atg<br>Leu Gly Val Val Gly Gln Ile Ile Pro Trp Asn Phe Pro Leu Leu Met<br>                165                 170                 175 | | 528 |
| gcg agc tgg aaa atg gct ccc gcg ctg gcg gcg ggc aac tgt gtg gtg<br>Ala Ser Trp Lys Met Ala Pro Ala Leu Ala Ala Gly Asn Cys Val Val<br>            180                 185                 190 | | 576 |
| ctg aaa ccc gca cgt ctt acc ccg ctt tct gta ctg cta atg gaa<br>Leu Lys Pro Ala Arg Leu Thr Pro Leu Ser Val Leu Leu Met Glu<br>        195                 200                 205 | | 624 |
| att gtc ggt gat tta ctg ccg ccg ggc gtg gtg aac gtg gtc aat ggc<br>Ile Val Gly Asp Leu Leu Pro Pro Gly Val Val Asn Val Val Asn Gly<br>    210                 215                 220 | | 672 |
| gca ggt ggg gta att ggc gaa tat ctg gcg acc tcg aaa cgc atc gcc<br>Ala Gly Gly Val Ile Gly Glu Tyr Leu Ala Thr Ser Lys Arg Ile Ala<br>225                 230                 235                 240 | | 720 |
| aaa gtg gcg ttt acc ggc tca acg gaa gtg ggc caa caa att atg caa<br>Lys Val Ala Phe Thr Gly Ser Thr Glu Val Gly Gln Gln Ile Met Gln<br>                245                 250                 255 | | 768 |
| tac gca acg caa aac att att ccg gtg acg ctg gag ttg ggc ggt aag<br>Tyr Ala Thr Gln Asn Ile Ile Pro Val Thr Leu Glu Leu Gly Gly Lys<br>            260                 265                 270 | | 816 |
| tcg cca aat atc ttc ttt gct gat gtg atg gat gaa gaa gat gcc ttt<br> | | 864 |

-continued

| | | |
|---|---|---|
| Ser Pro Asn Ile Phe Phe Ala Asp Val Met Asp Glu Glu Asp Ala Phe<br>275 280 285 | | |
| ttc gat aaa gcg ctg gaa ggc ttt gca ctg ttt gcc ttt aac cag ggc<br>Phe Asp Lys Ala Leu Glu Gly Phe Ala Leu Phe Ala Phe Asn Gln Gly<br>290 295 300 | 912 | |
| gaa gtt tgc acc tgt ccg agt cgt gct tta gtg cag gaa tct atc tac<br>Glu Val Cys Thr Cys Pro Ser Arg Ala Leu Val Gln Glu Ser Ile Tyr<br>305 310 315 320 | 960 | |
| gaa cgc ttt atg gaa cgc gcc atc cgc gtc gaa agc att cgt agc<br>Glu Arg Phe Met Glu Arg Ala Ile Arg Val Glu Ser Ile Arg Ser<br>325 330 335 | 1008 | |
| ggt aac ccg ctc gac agc gtg acg caa atg ggc gcg cag gtt tct cac<br>Gly Asn Pro Leu Asp Ser Val Thr Gln Met Gly Ala Gln Val Ser His<br>340 345 350 | 1056 | |
| ggg caa ctg gaa acc atc ctc aac tac att gat atc ggt aaa aaa gag<br>Gly Gln Leu Glu Thr Ile Leu Asn Tyr Ile Asp Ile Gly Lys Lys Glu<br>355 360 365 | 1104 | |
| ggc gct gac gtg ctc aca ggc ggg cgg cgc aag ctg ctg gaa ggt gaa<br>Gly Ala Asp Val Leu Thr Gly Gly Arg Arg Lys Leu Leu Glu Gly Glu<br>370 375 380 | 1152 | |
| ctg aaa gac ggc tac tac ctc gaa ccg acg att ctg ttt ggt cag aac<br>Leu Lys Asp Gly Tyr Tyr Leu Glu Pro Thr Ile Leu Phe Gly Gln Asn<br>385 390 395 400 | 1200 | |
| aat atg cgg gtg ttc cag gag gag att ttt ggc ccg gtg ctg gcg gtg<br>Asn Met Arg Val Phe Gln Glu Glu Ile Phe Gly Pro Val Leu Ala Val<br>405 410 415 | 1248 | |
| acc acc ttc aaa acg atg gaa gaa gcg ctg gag ctg gcg aac gat acg<br>Thr Thr Phe Lys Thr Met Glu Glu Ala Leu Glu Leu Ala Asn Asp Thr<br>420 425 430 | 1296 | |
| caa tat ggc ctg ggc gcg ggc gtc tgg agc cgc aac ggt aat ctg gcc<br>Gln Tyr Gly Leu Gly Ala Gly Val Trp Ser Arg Asn Gly Asn Leu Ala<br>435 440 445 | 1344 | |
| tat aag atg ggg cgc ggc ata cag gct ggg cgc gtg tgg acc aac tgt<br>Tyr Lys Met Gly Arg Gly Ile Gln Ala Gly Arg Val Trp Thr Asn Cys<br>450 455 460 | 1392 | |
| tat cac gct tac ccg gca cat gcg gcg ttt ggt ggc tac aaa caa tca<br>Tyr His Ala Tyr Pro Ala His Ala Ala Phe Gly Gly Tyr Lys Gln Ser<br>465 470 475 480 | 1440 | |
| ggt atc ggt cgc gaa acc cac aag atg atg ctg gag cat tac cag caa<br>Gly Ile Gly Arg Glu Thr His Lys Met Met Leu Glu His Tyr Gln Gln<br>485 490 495 | 1488 | |
| acc aag tgc ctg ctg gtg agc tac tcg gat aaa ccg ttg ggg ctg ttc<br>Thr Lys Cys Leu Leu Val Ser Tyr Ser Asp Lys Pro Leu Gly Leu Phe<br>500 505 510 | 1536 | |
| tga | 1539 | |

<210> SEQ ID NO 16
<211> LENGTH: 512
<212> TYPE: PRT
<213> ORGANISM: Escherichia coli

<400> SEQUENCE: 16

Met Thr Asn Asn Pro Pro Ser Ala Gln Ile Lys Pro Gly Glu Tyr Gly
1               5                   10                  15

Phe Pro Leu Lys Leu Lys Ala Arg Tyr Asp Asn Phe Ile Gly Gly Glu
            20                  25                  30

Trp Val Ala Pro Ala Asp Gly Glu Tyr Tyr Gln Asn Leu Thr Pro Val
        35                  40                  45

Thr Gly Gln Leu Leu Cys Glu Val Ala Ser Ser Gly Lys Arg Asp Ile
    50                  55                  60

```
Asp Leu Ala Leu Asp Ala Ala His Lys Val Lys Asp Lys Trp Ala His
 65                  70                  75                  80

Thr Ser Val Gln Asp Arg Ala Ala Ile Leu Phe Lys Ile Ala Asp Arg
                 85                  90                  95

Met Glu Gln Asn Leu Glu Leu Leu Ala Thr Ala Glu Thr Trp Asp Asn
            100                 105                 110

Gly Lys Pro Ile Arg Glu Thr Ser Ala Ala Asp Val Pro Leu Ala Ile
        115                 120                 125

Asp His Phe Arg Tyr Phe Ala Ser Cys Ile Arg Ala Gln Glu Gly Gly
    130                 135                 140

Ile Ser Glu Val Asp Ser Glu Thr Val Ala Tyr His Phe His Glu Pro
145                 150                 155                 160

Leu Gly Val Val Gly Gln Ile Ile Pro Trp Asn Phe Pro Leu Leu Met
                165                 170                 175

Ala Ser Trp Lys Met Ala Pro Ala Leu Ala Ala Gly Asn Cys Val Val
            180                 185                 190

Leu Lys Pro Ala Arg Leu Thr Pro Leu Ser Val Leu Leu Leu Met Glu
        195                 200                 205

Ile Val Gly Asp Leu Leu Pro Pro Gly Val Val Asn Val Val Asn Gly
    210                 215                 220

Ala Gly Gly Val Ile Gly Glu Tyr Leu Ala Thr Ser Lys Arg Ile Ala
225                 230                 235                 240

Lys Val Ala Phe Thr Gly Ser Thr Glu Val Gly Gln Gln Ile Met Gln
                245                 250                 255

Tyr Ala Thr Gln Asn Ile Ile Pro Val Thr Leu Glu Leu Gly Gly Lys
            260                 265                 270

Ser Pro Asn Ile Phe Phe Ala Asp Val Met Asp Glu Glu Asp Ala Phe
        275                 280                 285

Phe Asp Lys Ala Leu Glu Gly Phe Ala Leu Phe Ala Phe Asn Gln Gly
    290                 295                 300

Glu Val Cys Thr Cys Pro Ser Arg Ala Leu Val Gln Glu Ser Ile Tyr
305                 310                 315                 320

Glu Arg Phe Met Glu Arg Ala Ile Arg Arg Val Glu Ser Ile Arg Ser
                325                 330                 335

Gly Asn Pro Leu Asp Ser Val Thr Gln Met Gly Ala Gln Val Ser His
            340                 345                 350

Gly Gln Leu Glu Thr Ile Leu Asn Tyr Ile Asp Ile Gly Lys Lys Glu
        355                 360                 365

Gly Ala Asp Val Leu Thr Gly Gly Arg Arg Lys Leu Leu Glu Gly Glu
    370                 375                 380

Leu Lys Asp Gly Tyr Tyr Leu Glu Pro Thr Ile Leu Phe Gly Gln Asn
385                 390                 395                 400

Asn Met Arg Val Phe Gln Glu Glu Ile Phe Gly Pro Val Leu Ala Val
                405                 410                 415

Thr Thr Phe Lys Thr Met Glu Glu Ala Leu Glu Leu Ala Asn Asp Thr
            420                 425                 430

Gln Tyr Gly Leu Gly Ala Gly Val Trp Ser Arg Asn Gly Asn Leu Ala
        435                 440                 445

Tyr Lys Met Gly Arg Gly Ile Gln Ala Gly Arg Val Trp Thr Asn Cys
    450                 455                 460

Tyr His Ala Tyr Pro Ala His Ala Ala Phe Gly Gly Tyr Lys Gln Ser
465                 470                 475                 480

Gly Ile Gly Arg Glu Thr His Lys Met Met Leu Glu His Tyr Gln Gln
```

```
                    485                 490                 495
Thr Lys Cys Leu Leu Val Ser Tyr Ser Asp Lys Pro Leu Gly Leu Phe
            500                 505                 510

<210> SEQ ID NO 17
<211> LENGTH: 1440
<212> TYPE: DNA
<213> ORGANISM: Escherichia coli
<220> FEATURE:
<221> NAME/KEY: CDS
<222> LOCATION: (1)..(1440)

<400> SEQUENCE: 17 atg tca gta ccc gtt caa cat cct atg tat atc gat gga cag ttt gtt      48
Met Ser Val Pro Val Gln His Pro Met Tyr Ile Asp Gly Gln Phe Val
1               5                   10                  15 acc tgg cgt gga gac gca tgg att gat gtg gta aac cct gct aca gag      96
Thr Trp Arg Gly Asp Ala Trp Ile Asp Val Val Asn Pro Ala Thr Glu
            20                  25                  30 gct gtc att tcc cgc ata ccc gat ggt cag gcc gag gat gcc cgt aag     144
Ala Val Ile Ser Arg Ile Pro Asp Gly Gln Ala Glu Asp Ala Arg Lys
        35                  40                  45 gca atc gat gca gca gaa cgt gca caa cca gaa tgg gaa gcg ttg cct     192
Ala Ile Asp Ala Ala Glu Arg Ala Gln Pro Glu Trp Glu Ala Leu Pro
    50                  55                  60 gct att gaa cgc gcc agt tgg ttg cgc aaa atc tcc gcc ggg atc cgc     240
Ala Ile Glu Arg Ala Ser Trp Leu Arg Lys Ile Ser Ala Gly Ile Arg
65                  70                  75                  80 gaa cgc gcc agt gaa atc agt gcg ctg att gtt gaa gaa ggg ggc aag     288
Glu Arg Ala Ser Glu Ile Ser Ala Leu Ile Val Glu Glu Gly Gly Lys
                85                  90                  95 atc cag cag ctg gct gaa gtc gaa gtg gct ttt act gcc gac tat atc     336
Ile Gln Gln Leu Ala Glu Val Glu Val Ala Phe Thr Ala Asp Tyr Ile
            100                 105                 110 gat tac atg gcg gag tgg gca cgg cgt tac gag ggc gag att att caa     384
Asp Tyr Met Ala Glu Trp Ala Arg Arg Tyr Glu Gly Glu Ile Ile Gln
        115                 120                 125 agc gat cgt cca gga gaa aat att ctt ttg ttt aaa cgt gcg ctt ggt     432
Ser Asp Arg Pro Gly Glu Asn Ile Leu Leu Phe Lys Arg Ala Leu Gly
    130                 135                 140 gtg act acc ggc att ctg ccg tgg aac ttc ccg ttc ttc ctc att gcc     480
Val Thr Thr Gly Ile Leu Pro Trp Asn Phe Pro Phe Phe Leu Ile Ala
145                 150                 155                 160 cgc aaa atg gct ccc gct ctt ttg acc ggt aat acc atc gtc att aaa     528
Arg Lys Met Ala Pro Ala Leu Leu Thr Gly Asn Thr Ile Val Ile Lys
                165                 170                 175 cct agt gaa ttt acg cca aac aat gcg att gca ttc gcc aaa atc gtc     576
Pro Ser Glu Phe Thr Pro Asn Asn Ala Ile Ala Phe Ala Lys Ile Val
            180                 185                 190 gat gaa ata ggc ctt ccg cgc ggc gtg ttt aac ctt gta ctg ggg cgt     624
Asp Glu Ile Gly Leu Pro Arg Gly Val Phe Asn Leu Val Leu Gly Arg
        195                 200                 205 ggt gaa acc gtt ggg caa gaa ctg gcg ggt aac cca aag gtc gca atg     672
Gly Glu Thr Val Gly Gln Glu Leu Ala Gly Asn Pro Lys Val Ala Met
    210                 215                 220 gtc agt atg aca ggc agc gtc tct gca ggt gag aag atc atg gcg act     720
Val Ser Met Thr Gly Ser Val Ser Ala Gly Glu Lys Ile Met Ala Thr
225                 230                 235                 240 gcg gcg aaa aac atc acc aaa gtg tgt ctg gaa ttg ggg ggt aaa gca     768
Ala Ala Lys Asn Ile Thr Lys Val Cys Leu Glu Leu Gly Gly Lys Ala
                245                 250                 255
```

```
cca gct atc gta atg gac gat gcc gat ctt gaa ctg gca gtc aaa gcc      816
Pro Ala Ile Val Met Asp Asp Ala Asp Leu Glu Leu Ala Val Lys Ala
        260                 265                 270 atc gtt gat tca cgc gtc att aat agt ggg caa gtg tgt aac tgt gca      864
Ile Val Asp Ser Arg Val Ile Asn Ser Gly Gln Val Cys Asn Cys Ala
275                 280                 285 gaa cgt gtt tat gta cag aaa ggc att tat gat cag ttc gtc aat cgg      912
Glu Arg Val Tyr Val Gln Lys Gly Ile Tyr Asp Gln Phe Val Asn Arg
    290                 295                 300 ctg ggt gaa gcg atg cag gcg gtt caa ttt ggt aac ccc gct gaa cgc      960
Leu Gly Glu Ala Met Gln Ala Val Gln Phe Gly Asn Pro Ala Glu Arg
305                 310                 315                 320 aac gac att gcg atg ggg ccg ttg att aac gcc gcg gcg ctg gaa agg     1008
Asn Asp Ile Ala Met Gly Pro Leu Ile Asn Ala Ala Ala Leu Glu Arg
                325                 330                 335 gtc gag caa aaa gtg gcg cgc gca gta gaa gaa ggg gcg aga gtg gcg     1056
Val Glu Gln Lys Val Ala Arg Ala Val Glu Glu Gly Ala Arg Val Ala
            340                 345                 350 ttc ggt ggc aaa gcg gta gag ggg aaa gga tat tat tat ccg ccg aca     1104
Phe Gly Gly Lys Ala Val Glu Gly Lys Gly Tyr Tyr Tyr Pro Pro Thr
        355                 360                 365 ttg ctg ctg gat gtt cgc cag gaa atg tcg att atg cat gag gaa acc     1152
Leu Leu Leu Asp Val Arg Gln Glu Met Ser Ile Met His Glu Glu Thr
    370                 375                 380 ttt ggc ccg gtg ctg cca gtt gtc gca ttt gac acg ctg gaa gat gct     1200
Phe Gly Pro Val Leu Pro Val Val Ala Phe Asp Thr Leu Glu Asp Ala
385                 390                 395                 400 atc tca atg gct aat gac agt gat tac ggc ctg acc tca tca atc tat     1248
Ile Ser Met Ala Asn Asp Ser Asp Tyr Gly Leu Thr Ser Ser Ile Tyr
                405                 410                 415 acc caa aat ctg aac gtc gcg atg aaa gcc att aaa ggg ctg aag ttt     1296
Thr Gln Asn Leu Asn Val Ala Met Lys Ala Ile Lys Gly Leu Lys Phe
            420                 425                 430 ggt gaa act tac atc aac cgt gaa aac ttc gaa gct atg caa ggc ttc     1344
Gly Glu Thr Tyr Ile Asn Arg Glu Asn Phe Glu Ala Met Gln Gly Phe
        435                 440                 445 cac gcc gga tgg cgt aaa tcc ggt att ggc ggc gca gat ggt aaa cat     1392
His Ala Gly Trp Arg Lys Ser Gly Ile Gly Gly Ala Asp Gly Lys His
    450                 455                 460 ggc ttg cat gaa tat ctg cag acc cag gtg gtt tat tta cag tct taa     1440
Gly Leu His Glu Tyr Leu Gln Thr Gln Val Val Tyr Leu Gln Ser
465                 470                 475

<210> SEQ ID NO 18
<211> LENGTH: 479
<212> TYPE: PRT
<213> ORGANISM: Escherichia coli

<400> SEQUENCE: 18

Met Ser Val Pro Val Gln His Pro Met Tyr Ile Asp Gly Gln Phe Val
1               5                   10                  15

Thr Trp Arg Gly Asp Ala Trp Ile Asp Val Val Asn Pro Ala Thr Glu
            20                  25                  30

Ala Val Ile Ser Arg Ile Pro Asp Gly Gln Ala Glu Asp Ala Arg Lys
        35                  40                  45

Ala Ile Asp Ala Ala Glu Arg Ala Gln Pro Glu Trp Glu Ala Leu Pro
    50                  55                  60

Ala Ile Glu Arg Ala Ser Trp Leu Arg Lys Ile Ser Ala Gly Ile Arg
65                  70                  75                  80

Glu Arg Ala Ser Glu Ile Ser Ala Leu Ile Val Glu Gly Gly Gly Lys
```

```
                    85                  90                  95
Ile Gln Gln Leu Ala Glu Val Glu Val Ala Phe Thr Ala Asp Tyr Ile
                100                 105                 110

Asp Tyr Met Ala Glu Trp Ala Arg Arg Tyr Glu Gly Glu Ile Ile Gln
            115                 120                 125

Ser Asp Arg Pro Gly Glu Asn Ile Leu Leu Phe Lys Arg Ala Leu Gly
        130                 135                 140

Val Thr Thr Gly Ile Leu Pro Trp Asn Phe Pro Phe Phe Leu Ile Ala
145                 150                 155                 160

Arg Lys Met Ala Pro Ala Leu Leu Thr Gly Asn Thr Ile Val Ile Lys
                165                 170                 175

Pro Ser Glu Phe Thr Pro Asn Asn Ala Ile Ala Phe Ala Lys Ile Val
            180                 185                 190

Asp Glu Ile Gly Leu Pro Arg Gly Val Phe Asn Leu Val Leu Gly Arg
        195                 200                 205

Gly Glu Thr Val Gly Gln Glu Leu Ala Gly Asn Pro Lys Val Ala Met
210                 215                 220

Val Ser Met Thr Gly Ser Val Ser Ala Gly Glu Lys Ile Met Ala Thr
225                 230                 235                 240

Ala Ala Lys Asn Ile Thr Lys Val Cys Leu Glu Leu Gly Gly Lys Ala
                245                 250                 255

Pro Ala Ile Val Met Asp Asp Ala Asp Leu Glu Leu Ala Val Lys Ala
            260                 265                 270

Ile Val Asp Ser Arg Val Ile Asn Ser Gly Gln Val Cys Asn Cys Ala
        275                 280                 285

Glu Arg Val Tyr Val Gln Lys Gly Ile Tyr Asp Gln Phe Val Asn Arg
290                 295                 300

Leu Gly Glu Ala Met Gln Ala Val Gln Phe Gly Asn Pro Ala Glu Arg
305                 310                 315                 320

Asn Asp Ile Ala Met Gly Pro Leu Ile Asn Ala Ala Ala Leu Glu Arg
                325                 330                 335

Val Glu Gln Lys Val Ala Arg Ala Val Glu Glu Gly Ala Arg Val Ala
            340                 345                 350

Phe Gly Gly Lys Ala Val Glu Gly Lys Gly Tyr Tyr Tyr Pro Pro Thr
        355                 360                 365

Leu Leu Leu Asp Val Arg Gln Glu Met Ser Ile Met His Glu Glu Thr
370                 375                 380

Phe Gly Pro Val Leu Pro Val Val Ala Phe Asp Thr Leu Glu Asp Ala
385                 390                 395                 400

Ile Ser Met Ala Asn Asp Ser Asp Tyr Gly Leu Thr Ser Ser Ile Tyr
                405                 410                 415

Thr Gln Asn Leu Asn Val Ala Met Lys Ala Ile Lys Gly Leu Lys Phe
            420                 425                 430

Gly Glu Thr Tyr Ile Asn Arg Glu Asn Phe Glu Ala Met Gln Gly Phe
        435                 440                 445

His Ala Gly Trp Arg Lys Ser Gly Ile Gly Gly Ala Asp Gly Lys His
450                 455                 460

Gly Leu His Glu Tyr Leu Gln Thr Gln Val Val Tyr Leu Gln Ser
465                 470                 475

<210> SEQ ID NO 19
<211> LENGTH: 1488
<212> TYPE: DNA
<213> ORGANISM: Escherichia coli
<220> FEATURE:
```

<221> NAME/KEY: CDS
<222> LOCATION: (1)..(1488)

<400> SEQUENCE: 19

| | | | | | | | | | | | | | | | | |
|---|---|---|---|---|---|---|---|---|---|---|---|---|---|---|---|---|
| atg | aat | ttt | cat | cat | ctg | gct | tac | tgg | cag | gat | aaa | gcg | tta | agt | ctc | 48 |
| Met | Asn | Phe | His | His | Leu | Ala | Tyr | Trp | Gln | Asp | Lys | Ala | Leu | Ser | Leu | |
| 1 | | | | 5 | | | | | 10 | | | | | 15 | | |

| gcc | att | gaa | aac | cgc | tta | ttt | att | aac | ggt | gaa | tat | act | gct | gcg | gcg | 96 |
|---|---|---|---|---|---|---|---|---|---|---|---|---|---|---|---|---|
| Ala | Ile | Glu | Asn | Arg | Leu | Phe | Ile | Asn | Gly | Glu | Tyr | Thr | Ala | Ala | Ala | |
| | | 20 | | | | | 25 | | | | | 30 | | | | |

| gaa | aat | gaa | acc | ttt | gaa | acc | gtt | gat | ccg | gtc | acc | cag | gca | ccg | ctg | 144 |
|---|---|---|---|---|---|---|---|---|---|---|---|---|---|---|---|---|
| Glu | Asn | Glu | Thr | Phe | Glu | Thr | Val | Asp | Pro | Val | Thr | Gln | Ala | Pro | Leu | |
| | 35 | | | | | 40 | | | | | 45 | | | | | |

| gcg | aaa | att | gcc | cgc | ggc | aag | agc | gtc | gat | atc | gac | cgt | gcg | atg | agc | 192 |
|---|---|---|---|---|---|---|---|---|---|---|---|---|---|---|---|---|
| Ala | Lys | Ile | Ala | Arg | Gly | Lys | Ser | Val | Asp | Ile | Asp | Arg | Ala | Met | Ser | |
| 50 | | | | | 55 | | | | | 60 | | | | | | |

| gca | gca | cgc | ggc | gta | ttt | gaa | cgc | ggc | gac | tgg | tca | ctc | tct | tct | ccg | 240 |
|---|---|---|---|---|---|---|---|---|---|---|---|---|---|---|---|---|
| Ala | Ala | Arg | Gly | Val | Phe | Glu | Arg | Gly | Asp | Trp | Ser | Leu | Ser | Ser | Pro | |
| 65 | | | | | 70 | | | | | 75 | | | | | 80 | |

| gct | aaa | cgt | aaa | gcg | gta | ctg | aat | aaa | ctc | gcc | gat | tta | atg | gaa | gcc | 288 |
|---|---|---|---|---|---|---|---|---|---|---|---|---|---|---|---|---|
| Ala | Lys | Arg | Lys | Ala | Val | Leu | Asn | Lys | Leu | Ala | Asp | Leu | Met | Glu | Ala | |
| | | | | 85 | | | | | 90 | | | | | 95 | | |

| cac | gcc | gaa | gag | ctg | gca | ctg | ctg | gaa | act | ctc | gac | acc | ggc | aaa | ccg | 336 |
|---|---|---|---|---|---|---|---|---|---|---|---|---|---|---|---|---|
| His | Ala | Glu | Glu | Leu | Ala | Leu | Leu | Glu | Thr | Leu | Asp | Thr | Gly | Lys | Pro | |
| | | | 100 | | | | | 105 | | | | | 110 | | | |

| att | cgt | cac | agt | ctg | cgt | gat | gat | att | ccc | ggc | gcg | gcg | cgc | gcc | att | 384 |
|---|---|---|---|---|---|---|---|---|---|---|---|---|---|---|---|---|
| Ile | Arg | His | Ser | Leu | Arg | Asp | Asp | Ile | Pro | Gly | Ala | Ala | Arg | Ala | Ile | |
| | | 115 | | | | | 120 | | | | | 125 | | | | |

| cgc | tgg | tac | gcc | gaa | gcg | atc | gac | aaa | gtg | tat | ggc | gaa | gtg | gcg | acc | 432 |
|---|---|---|---|---|---|---|---|---|---|---|---|---|---|---|---|---|
| Arg | Trp | Tyr | Ala | Glu | Ala | Ile | Asp | Lys | Val | Tyr | Gly | Glu | Val | Ala | Thr | |
| 130 | | | | | 135 | | | | | 140 | | | | | | |

| acc | agt | agc | cat | gag | ctg | gcg | atg | atc | gtg | cgt | gaa | ccg | gtc | ggc | gtg | 480 |
|---|---|---|---|---|---|---|---|---|---|---|---|---|---|---|---|---|
| Thr | Ser | Ser | His | Glu | Leu | Ala | Met | Ile | Val | Arg | Glu | Pro | Val | Gly | Val | |
| 145 | | | | | 150 | | | | | 155 | | | | | 160 | |

| att | gcc | gcc | atc | gtg | ccg | tgg | aac | ttc | ccg | ctg | ttg | ctg | act | tgc | tgg | 528 |
|---|---|---|---|---|---|---|---|---|---|---|---|---|---|---|---|---|
| Ile | Ala | Ala | Ile | Val | Pro | Trp | Asn | Phe | Pro | Leu | Leu | Leu | Thr | Cys | Trp | |
| | | | | 165 | | | | | 170 | | | | | 175 | | |

| aaa | ctc | ggc | ccg | gcg | ctg | gcg | gcg | gga | aac | agc | gtg | att | cta | aaa | ccg | 576 |
|---|---|---|---|---|---|---|---|---|---|---|---|---|---|---|---|---|
| Lys | Leu | Gly | Pro | Ala | Leu | Ala | Ala | Gly | Asn | Ser | Val | Ile | Leu | Lys | Pro | |
| | | | 180 | | | | | 185 | | | | | 190 | | | |

| tct | gaa | aaa | tca | ccg | ctc | agt | gcg | att | cgt | ctc | gcg | ggg | ctg | gcg | aaa | 624 |
|---|---|---|---|---|---|---|---|---|---|---|---|---|---|---|---|---|
| Ser | Glu | Lys | Ser | Pro | Leu | Ser | Ala | Ile | Arg | Leu | Ala | Gly | Leu | Ala | Lys | |
| | | 195 | | | | | 200 | | | | | 205 | | | | |

| gaa | gca | ggc | ttg | ccg | gat | ggt | gtg | ttg | aac | gtg | gtg | acg | ggt | ttt | ggt | 672 |
|---|---|---|---|---|---|---|---|---|---|---|---|---|---|---|---|---|
| Glu | Ala | Gly | Leu | Pro | Asp | Gly | Val | Leu | Asn | Val | Val | Thr | Gly | Phe | Gly | |
| 210 | | | | | 215 | | | | | 220 | | | | | | |

| cat | gaa | gcc | ggg | cag | gcg | ctg | tcg | cgt | cat | aac | gat | atc | gac | gcc | att | 720 |
|---|---|---|---|---|---|---|---|---|---|---|---|---|---|---|---|---|
| His | Glu | Ala | Gly | Gln | Ala | Leu | Ser | Arg | His | Asn | Asp | Ile | Asp | Ala | Ile | |
| 225 | | | | | 230 | | | | | 235 | | | | | 240 | |

| gcc | ttt | acc | ggt | tca | acc | cgt | acc | ggg | aaa | cag | ctg | ctg | aaa | gat | gcg | 768 |
|---|---|---|---|---|---|---|---|---|---|---|---|---|---|---|---|---|
| Ala | Phe | Thr | Gly | Ser | Thr | Arg | Thr | Gly | Lys | Gln | Leu | Leu | Lys | Asp | Ala | |
| | | | | 245 | | | | | 250 | | | | | 255 | | |

| ggc | gac | agc | aac | atg | aaa | cgc | gtc | tgg | ctg | gaa | gcg | ggc | ggc | aaa | agc | 816 |
|---|---|---|---|---|---|---|---|---|---|---|---|---|---|---|---|---|
| Gly | Asp | Ser | Asn | Met | Lys | Arg | Val | Trp | Leu | Glu | Ala | Gly | Gly | Lys | Ser | |
| | | | 260 | | | | | 265 | | | | | 270 | | | |

| gcc | aac | atc | gtt | ttc | gct | gac | tgc | ccg | gat | ttg | caa | cag | gcg | gca | agc | 864 |
|---|---|---|---|---|---|---|---|---|---|---|---|---|---|---|---|---|
| Ala | Asn | Ile | Val | Phe | Ala | Asp | Cys | Pro | Asp | Leu | Gln | Gln | Ala | Ala | Ser | |
| | | 275 | | | | | 280 | | | | | 285 | | | | |

| gcc | acc | gca | gca | ggc | att | ttc | tac | aac | cag | gga | cag | gtg | tgc | atc | gcc | 912 |
|---|---|---|---|---|---|---|---|---|---|---|---|---|---|---|---|---|
| Ala | Thr | Ala | Ala | Gly | Ile | Phe | Tyr | Asn | Gln | Gly | Gln | Val | Cys | Ile | Ala | |
| | 290 | | | | | 295 | | | | | 300 | | | | | |

|  |  |  |  |  |  |  |  |  |  |  |  |  |  |  |  |  |
|---|---|---|---|---|---|---|---|---|---|---|---|---|---|---|---|---|
| gga | acg | cgc | ctg | ttg | ctg | gaa | gag | agc | atc | gcc | gat | gaa | ttc | tta | gcc | 960 |
| Gly | Thr | Arg | Leu | Leu | Leu | Glu | Glu | Ser | Ile | Ala | Asp | Glu | Phe | Leu | Ala |  |
| 305 |  |  |  |  | 310 |  |  |  |  | 315 |  |  |  |  | 320 |  |
| ctg | tta | aaa | cag | cag | gcg | caa | aac | tgg | cag | ccg | ggc | cat | cca | ctt | gat | 1008 |
| Leu | Leu | Lys | Gln | Gln | Ala | Gln | Asn | Trp | Gln | Pro | Gly | His | Pro | Leu | Asp |  |
|  |  |  |  | 325 |  |  |  |  | 330 |  |  |  |  | 335 |  |  |
| ccc | gca | acc | acc | atg | ggc | acc | tta | atc | gac | tgc | gcc | cac | gcc | gac | tcg | 1056 |
| Pro | Ala | Thr | Thr | Met | Gly | Thr | Leu | Ile | Asp | Cys | Ala | His | Ala | Asp | Ser |  |
|  |  || 340 |  |  |  |  | 345 |  |  |  |  | 350 |  |  |  |
| gtc | cat | agc | ttt | att | cgg | gaa | ggc | gaa | agc | aaa | ggg | caa | ctg | ttg | ttg | 1104 |
| Val | His | Ser | Phe | Ile | Arg | Glu | Gly | Glu | Ser | Lys | Gly | Gln | Leu | Leu | Leu |  |
|  |  | 355 |  |  |  |  | 360 |  |  |  |  | 365 |  |  |  |  |
| gat | ggc | cgt | aac | gcc | ggg | ctg | gct | gcc | gcc | atc | ggc | ccg | acc | atc | ttt | 1152 |
| Asp | Gly | Arg | Asn | Ala | Gly | Leu | Ala | Ala | Ala | Ile | Gly | Pro | Thr | Ile | Phe |  |
| 370 |  |  |  |  | 375 |  |  |  |  | 380 |  |  |  |  |  |  |
| gtg | gat | gtg | gac | ccg | aat | gcg | tcc | tta | agt | cgc | gaa | gag | att | ttc | ggt | 1200 |
| Val | Asp | Val | Asp | Pro | Asn | Ala | Ser | Leu | Ser | Arg | Glu | Glu | Ile | Phe | Gly |  |
| 385 |  |  |  |  | 390 |  |  |  |  | 395 |  |  |  |  | 400 |  |
| ccg | gtg | ctg | gtg | gtc | acg | cgt | ttc | aca | tca | gaa | gaa | cag | gcg | cta | cag | 1248 |
| Pro | Val | Leu | Val | Val | Thr | Arg | Phe | Thr | Ser | Glu | Glu | Gln | Ala | Leu | Gln |  |
|  |  |  |  | 405 |  |  |  |  | 410 |  |  |  |  | 415 |  |  |
| ctt | gcc | aac | gac | agc | cag | tac | ggc | ctt | ggc | gcg | gcg | gta | tgg | acg | cgc | 1296 |
| Leu | Ala | Asn | Asp | Ser | Gln | Tyr | Gly | Leu | Gly | Ala | Ala | Val | Trp | Thr | Arg |  |
|  |  |  | 420 |  |  |  |  | 425 |  |  |  |  | 430 |  |  |  |
| gac | ctc | tcc | cgc | gcg | cac | cgc | atg | agc | cga | cgc | ctg | aaa | gcc | ggt | tcc | 1344 |
| Asp | Leu | Ser | Arg | Ala | His | Arg | Met | Ser | Arg | Arg | Leu | Lys | Ala | Gly | Ser |  |
|  |  | 435 |  |  |  |  | 440 |  |  |  |  | 445 |  |  |  |  |
| gtc | ttc | gtc | aat | aac | tac | aac | gac | ggc | gat | atg | acc | gtg | ccg | ttt | ggc | 1392 |
| Val | Phe | Val | Asn | Asn | Tyr | Asn | Asp | Gly | Asp | Met | Thr | Val | Pro | Phe | Gly |  |
| 450 |  |  |  |  | 455 |  |  |  |  | 460 |  |  |  |  |  |  |
| ggc | tat | aag | cag | agc | ggc | aac | ggt | cgc | gac | aaa | tcc | ctg | cat | gcc | ctt | 1440 |
| Gly | Tyr | Lys | Gln | Ser | Gly | Asn | Gly | Arg | Asp | Lys | Ser | Leu | His | Ala | Leu |  |
| 465 |  |  |  |  | 470 |  |  |  |  | 475 |  |  |  |  | 480 |  |
| gaa | aaa | ttc | act | gaa | ctg | aaa | acc | atc | tgg | ata | agc | ctg | gag | gcc | tga | 1488 |
| Glu | Lys | Phe | Thr | Glu | Leu | Lys | Thr | Ile | Trp | Ile | Ser | Leu | Glu | Ala |  |  |
|  |  |  |  | 485 |  |  |  |  | 490 |  |  |  |  | 495 |  |  |

<210> SEQ ID NO 20
<211> LENGTH: 495
<212> TYPE: PRT
<213> ORGANISM: Escherichia coli

<400> SEQUENCE: 20

Met Asn Phe His His Leu Ala Tyr Trp Gln Asp Lys Ala Leu Ser Leu
1               5                   10                  15

Ala Ile Glu Asn Arg Leu Phe Ile Asn Gly Glu Tyr Thr Ala Ala
            20                  25                  30

Glu Asn Glu Thr Phe Glu Thr Val Asp Pro Val Thr Gln Ala Pro Leu
        35                  40                  45

Ala Lys Ile Ala Arg Gly Lys Ser Val Asp Ile Asp Arg Ala Met Ser
    50                  55                  60

Ala Ala Arg Gly Val Phe Glu Arg Gly Asp Trp Ser Leu Ser Ser Pro
65                  70                  75                  80

Ala Lys Arg Lys Ala Val Leu Asn Lys Leu Ala Asp Leu Met Glu Ala
                85                  90                  95

His Ala Glu Glu Leu Ala Leu Leu Glu Thr Leu Asp Thr Gly Lys Pro
            100                 105                 110

Ile Arg His Ser Leu Arg Asp Asp Ile Pro Gly Ala Ala Arg Ala Ile
        115                 120                 125

Arg Trp Tyr Ala Glu Ala Ile Asp Lys Val Tyr Gly Glu Val Ala Thr
130                 135                 140

Thr Ser Ser His Glu Leu Ala Met Ile Val Arg Glu Pro Val Gly Val
145                 150                 155                 160

Ile Ala Ala Ile Val Pro Trp Asn Phe Pro Leu Leu Leu Thr Cys Trp
                165                 170                 175

Lys Leu Gly Pro Ala Leu Ala Ala Gly Asn Ser Val Ile Leu Lys Pro
            180                 185                 190

Ser Glu Lys Ser Pro Leu Ser Ala Ile Arg Leu Ala Gly Leu Ala Lys
        195                 200                 205

Glu Ala Gly Leu Pro Asp Gly Val Leu Asn Val Val Thr Gly Phe Gly
210                 215                 220

His Glu Ala Gly Gln Ala Leu Ser Arg His Asn Asp Ile Asp Ala Ile
225                 230                 235                 240

Ala Phe Thr Gly Ser Thr Arg Thr Gly Lys Gln Leu Leu Lys Asp Ala
                245                 250                 255

Gly Asp Ser Asn Met Lys Arg Val Trp Leu Glu Ala Gly Gly Lys Ser
            260                 265                 270

Ala Asn Ile Val Phe Ala Asp Cys Pro Asp Leu Gln Gln Ala Ala Ser
        275                 280                 285

Ala Thr Ala Ala Gly Ile Phe Tyr Asn Gln Gly Gln Val Cys Ile Ala
290                 295                 300

Gly Thr Arg Leu Leu Leu Glu Glu Ser Ile Ala Asp Glu Phe Leu Ala
305                 310                 315                 320

Leu Leu Lys Gln Gln Ala Gln Asn Trp Gln Pro Gly His Pro Leu Asp
                325                 330                 335

Pro Ala Thr Thr Met Gly Thr Leu Ile Asp Cys Ala His Ala Asp Ser
            340                 345                 350

Val His Ser Phe Ile Arg Glu Gly Glu Ser Lys Gly Gln Leu Leu Leu
        355                 360                 365

Asp Gly Arg Asn Ala Gly Leu Ala Ala Ala Ile Gly Pro Thr Ile Phe
370                 375                 380

Val Asp Val Asp Pro Asn Ala Ser Leu Ser Arg Glu Glu Ile Phe Gly
385                 390                 395                 400

Pro Val Leu Val Val Thr Arg Phe Thr Ser Glu Glu Gln Ala Leu Gln
                405                 410                 415

Leu Ala Asn Asp Ser Gln Tyr Gly Leu Gly Ala Ala Val Trp Thr Arg
            420                 425                 430

Asp Leu Ser Arg Ala His Arg Met Ser Arg Arg Leu Lys Ala Gly Ser
        435                 440                 445

Val Phe Val Asn Asn Tyr Asn Asp Gly Asp Met Thr Val Pro Phe Gly
450                 455                 460

Gly Tyr Lys Gln Ser Gly Asn Gly Arg Asp Lys Ser Leu His Ala Leu
465                 470                 475                 480

Glu Lys Phe Thr Glu Leu Lys Thr Ile Trp Ile Ser Leu Glu Ala
                485                 490                 495

<210> SEQ ID NO 21
<211> LENGTH: 1395
<212> TYPE: DNA
<213> ORGANISM: Escherichia coli

<400> SEQUENCE: 21
atgcctgacg ctaaaaaaca ggggcggtca acaaggcaa tgacgttttt cgtctgcttc    60

```
cttgccgctc tggcgggatt actctttggc ctggatatcg gtgtaattgc tggcgcactg      120
ccgtttattg cagatgaatt ccagattact tcgcacacgc aagaatgggt cgtaagctcc      180
atgatgttcg gtgcggcagt cggtgcggtg ggcagcggct ggctctcctt taaactcggg      240
cgcaaaaaga gcctgatgat cggcgcaatt ttgtttgttg ccggttcgct gttctctgcg      300
gctgcgccaa acgttgaagt actgattctt tcccgcgttc tactggggct ggcggtgggt      360
gtggcctctt ataccgcacc gctgtacctc tctgaaattg cgccggaaaa aattcgtggc      420
agtatgatct cgatgtatca gttgatgatc actatcggga tcctcggtgc ttatctttct      480
gataccgcct tcagctacac cggtgcatgg cgctggatgc tgggtgtgat tatcatcccg      540 gcaatttttgc tgctgattgg tgtcttcttc ctgccagaca gcccacgttg gtttgccgcc      600
aaacgccgtt ttgttgatgc cgaacgcgtg ctgctacgcc tgcgtgacac cagcgcggaa      660
gcgaaacgcg aactggatga atccgtgaaa gtttgcaggg ttaaacagag tggctgggcg      720
ctgtttaaag agaacagcaa cttccgccgc gcggtgttcc ttggcgtact gttgcaggta      780
atgcagcaat tcaccgggat gaacgtcatc atgtattacg cgccgaaaat cttcgaactg      840
gcgggttata ccaacactac cgagcaaatg tgggggaccg tgattgtcgg cctgaccaac      900
gtacttgcca cctttatcgc aatcggcctt gttgaccgct ggggacgtaa accaacgcta      960
acgctgggct tcctggtgat ggctgctggc atgggcgtac tcggtacaat gatgcatatc     1020
ggtattcact ctccgtcggc gcagtatttc gccatcgcca tgctgctgat gtttattgtc     1080
ggttttgcca tgagtgccgg tccgctgatt tgggtactgt gctccgaaat tcagccgctg     1140
aaaggccgcg attttggcat cacctgctcc actgccacca actggattgc caacatgatc     1200
gttggcgcaa cgttcctgac catgctcaac acgctgggta acgccaacac cttctgggtg     1260
tatgcggctc tgaacgtact gtttatcctg ctgacattgt ggctggtacc ggaaaccaaa     1320
cacgtttcgc tggaacatat tgaacgtaat ctgatgaaag gtcgtaaact gcgcgaaata     1380
ggcgctcacg attaa                                                       1395

<210> SEQ ID NO 22
<211> LENGTH: 464
<212> TYPE: PRT
<213> ORGANISM: Escherichia coli

<400> SEQUENCE: 22

Met Pro Asp Ala Lys Lys Gln Gly Arg Ser Asn Lys Ala Met Thr Phe
1               5                   10                  15

Phe Val Cys Phe Leu Ala Ala Leu Ala Gly Leu Leu Phe Gly Leu Asp
            20                  25                  30

Ile Gly Val Ile Ala Gly Ala Leu Pro Phe Ile Ala Asp Glu Phe Gln
        35                  40                  45

Ile Thr Ser His Thr Gln Glu Trp Val Val Ser Met Met Phe Gly
    50                  55                  60

Ala Ala Val Gly Ala Val Gly Ser Gly Trp Leu Ser Phe Lys Leu Gly
65                  70                  75                  80

Arg Lys Lys Ser Leu Met Ile Gly Ala Ile Leu Phe Val Ala Gly Ser
                85                  90                  95

Leu Phe Ser Ala Ala Pro Asn Val Glu Val Leu Ile Leu Ser Arg
            100                 105                 110

Val Leu Leu Gly Leu Ala Val Gly Val Ala Ser Tyr Thr Ala Pro Leu
        115                 120                 125

Tyr Leu Ser Glu Ile Ala Pro Glu Lys Ile Arg Gly Ser Met Ile Ser
    130                 135                 140
```

```
Met Tyr Gln Leu Met Ile Thr Ile Gly Ile Leu Gly Ala Tyr Leu Ser
145                 150                 155                 160

Asp Thr Ala Phe Ser Tyr Thr Gly Ala Trp Arg Trp Met Leu Gly Val
                165                 170                 175

Ile Ile Ile Pro Ala Ile Leu Leu Ile Gly Val Phe Phe Leu Pro
            180                 185                 190

Asp Ser Pro Arg Trp Phe Ala Ala Lys Arg Arg Phe Val Asp Ala Glu
            195                 200                 205

Arg Val Leu Leu Arg Leu Arg Asp Thr Ser Ala Glu Ala Lys Arg Glu
        210                 215                 220

Leu Asp Glu Ile Arg Glu Ser Leu Gln Val Lys Gln Ser Gly Trp Ala
225                 230                 235                 240

Leu Phe Lys Glu Asn Ser Asn Phe Arg Arg Ala Val Phe Leu Gly Val
                245                 250                 255

Leu Leu Gln Val Met Gln Gln Phe Thr Gly Met Asn Val Ile Met Tyr
            260                 265                 270

Tyr Ala Pro Lys Ile Phe Glu Leu Ala Gly Tyr Thr Asn Thr Thr Glu
        275                 280                 285

Gln Met Trp Gly Thr Val Ile Val Gly Leu Thr Asn Val Leu Ala Thr
290                 295                 300

Phe Ile Ala Ile Gly Leu Val Asp Arg Trp Gly Arg Lys Pro Thr Leu
305                 310                 315                 320

Thr Leu Gly Phe Leu Val Met Ala Ala Gly Met Gly Val Leu Gly Thr
                325                 330                 335

Met Met His Ile Gly Ile His Ser Pro Ser Ala Gln Tyr Phe Ala Ile
            340                 345                 350

Ala Met Leu Leu Met Phe Ile Val Gly Phe Ala Met Ser Ala Gly Pro
        355                 360                 365

Leu Ile Trp Val Leu Cys Ser Glu Ile Gln Pro Leu Lys Gly Arg Asp
370                 375                 380

Phe Gly Ile Thr Cys Ser Thr Ala Thr Asn Trp Ile Ala Asn Met Ile
385                 390                 395                 400

Val Gly Ala Thr Phe Leu Thr Met Leu Asn Thr Leu Gly Asn Ala Asn
                405                 410                 415

Thr Phe Trp Val Tyr Ala Ala Leu Asn Val Leu Phe Ile Leu Leu Thr
            420                 425                 430

Leu Trp Leu Val Pro Glu Thr Lys His Val Ser Leu Glu His Ile Glu
        435                 440                 445

Arg Asn Leu Met Lys Gly Arg Lys Leu Arg Glu Ile Gly Ala His Asp
450                 455                 460
```

<210> SEQ ID NO 23
<211> LENGTH: 1236
<212> TYPE: DNA
<213> ORGANISM: Bacillus licheniformis

<400> SEQUENCE: 23

```
atgaaaagct caaacagtct gtattggaaa ctaagcgcct attttttctt ttctttttt      60 acttggtctt ccagctattc tttatttgcg atttggttag ggcaagaaat caatttgaac    120
gggtccgcga cgggcattat cttttctgta acgctatctt tactttgtg catgcagcct     180 ttgtacggtt ttatctccga taagctcggg ctgaagaaaa acatattatt tatgatcagt    240
ttgctgctcg tatttacggg tcccttttat attttcgtct acggaccgct tttgcaatac    300
aacgtctttc ttggggctat cgtcggggga atttatttgg gaactgcttt tctcgccgga    360
```

```
atcggtgcga ttgaaacctt tattgaaaag gtcagccgca aatatcaatt tgaatatgga    420
agaacaagga tgtgggggtc cctcggctgg gctgcggcga catttttgc aggtcagctg     480 ttcaatatcg atccgaatat caacttctgg gttgcgtccg cctcagcaat catattggtg    540
gccattattg tttccgtaaa aattgagatg acagatgatg aaaaggaaag agcagactcg    600
gtcggattaa aagacgtagg aggcttttt ctcttaaaag atttctggtt tttgatgctg     660
tacgtgatcg gcgtaacatg cgtgtacggc gtctatgacc agcagttccc gctttactac    720
gcttccttat ttccgactgc ggccttgggg aaccaaatat ttggatacct taattcattc    780
caagtattta ttgaagcggg catgatgttt cttgcgcctt tcatcgtcaa taagctcggt    840
cctaaaaaaa gcttgatttt agcggggctg ttaatggctt ccggattat cggttccgga    900 cttgtcagcg gaccggtcgg aatttcatcg atgaaactca ttcatgcttt agaattgccg    960
attatgctga ttgcgatgtt taaatatttg gcgactaatt tgataatcg tctttcatcc    1020 gtactttatc ttgtcggctt tcaattcgca tcccaggtag gcacgtcgat ttttcgccg    1080 cttgcgggag gtttatacga cagcatcgga tttcgccaca cttatctcat catgggagca    1140
atggtccttt gttttaccat tatttcgatt tttaccttgc tagactcaaa gaaagatgtt    1200
gaatttgctc aaaatctaca aagcaatcat atatag                              1236
```

<210> SEQ ID NO 24
<211> LENGTH: 411
<212> TYPE: PRT
<213> ORGANISM: Bacillus licheniformis

<400> SEQUENCE: 24

Met Lys Ser Ser Asn Ser Leu Tyr Trp Lys Leu Ser Ala Tyr Phe Phe
1               5                   10                  15

Phe Phe Phe Phe Thr Trp Ser Ser Ser Tyr Ser Leu Phe Ala Ile Trp
                20                  25                  30

Leu Gly Gln Glu Ile Asn Leu Asn Gly Ser Ala Thr Gly Ile Ile Phe
            35                  40                  45

Ser Val Asn Ala Ile Phe Thr Leu Cys Met Gln Pro Leu Tyr Gly Phe
        50                  55                  60

Ile Ser Asp Lys Leu Gly Leu Lys Lys Asn Ile Leu Phe Met Ile Ser
65                  70                  75                  80

Leu Leu Leu Val Phe Thr Gly Pro Phe Tyr Ile Phe Val Tyr Gly Pro
                85                  90                  95

Leu Leu Gln Tyr Asn Val Phe Leu Gly Ala Ile Val Gly Gly Ile Tyr
                100                 105                 110

Leu Gly Thr Ala Phe Leu Ala Gly Ile Gly Ala Ile Glu Thr Phe Ile
            115                 120                 125

Glu Lys Val Ser Arg Lys Tyr Gln Phe Glu Tyr Gly Arg Thr Arg Met
        130                 135                 140

Trp Gly Ser Leu Gly Trp Ala Ala Ala Thr Phe Phe Ala Gly Gln Leu
145                 150                 155                 160

Phe Asn Ile Asp Pro Asn Ile Asn Phe Trp Val Ala Ser Ala Ser Ala
                165                 170                 175

Ile Ile Leu Val Ala Ile Ile Val Ser Val Lys Ile Glu Met Thr Asp
                180                 185                 190

Asp Glu Lys Glu Arg Ala Asp Ser Val Gly Leu Lys Asp Val Gly Gly
            195                 200                 205

Leu Phe Leu Leu Lys Asp Phe Trp Phe Leu Met Leu Tyr Val Ile Gly
        210                 215                 220

```
Val Thr Cys Val Tyr Gly Val Tyr Asp Gln Gln Phe Pro Leu Tyr Tyr
225                 230                 235                 240

Ala Ser Leu Phe Pro Thr Ala Ala Leu Gly Asn Gln Ile Phe Gly Tyr
            245                 250                 255

Leu Asn Ser Phe Gln Val Phe Ile Glu Ala Gly Met Met Phe Leu Ala
        260                 265                 270

Pro Phe Ile Val Asn Lys Leu Gly Pro Lys Lys Ser Leu Ile Leu Ala
    275                 280                 285

Gly Leu Leu Met Ala Phe Arg Ile Ile Gly Ser Gly Leu Val Ser Gly
290                 295                 300

Pro Val Gly Ile Ser Ser Met Lys Leu Ile His Ala Leu Glu Leu Pro
305                 310                 315                 320

Ile Met Leu Ile Ala Met Phe Lys Tyr Leu Ala Thr Asn Phe Asp Asn
                325                 330                 335

Arg Leu Ser Ser Val Leu Tyr Leu Val Gly Phe Gln Phe Ala Ser Gln
            340                 345                 350

Val Gly Thr Ser Ile Phe Ser Pro Leu Ala Gly Gly Leu Tyr Asp Ser
        355                 360                 365

Ile Gly Phe Arg His Thr Tyr Leu Ile Met Gly Ala Met Val Leu Cys
    370                 375                 380

Phe Thr Ile Ile Ser Ile Phe Thr Leu Leu Asp Ser Lys Lys Asp Val
385                 390                 395                 400

Glu Phe Ala Gln Asn Leu Gln Ser Asn His Ile
                405                 410

<210> SEQ ID NO 25
<211> LENGTH: 1479
<212> TYPE: DNA
<213> ORGANISM: Bacillus licheniformis

<400> SEQUENCE: 25
atgaacagaa ttcagcaggc agaagaagca ttaaagaaag ccgggaaaaa agtgaatcgc      60
cgttaccgaa tgggctatca catgatgccc cgggcaaact ggataaatga tccaaacgga     120
cttattcaat ataaggggga gtatcatgtc ttttatcaac atcatccgta tgatgagaat     180
tgggggccga tgcattgggg ccatttgaag agcaaggatc ttattcactg ggagcacttg     240
ccggttgctt tagcgccggg agacgaattt gatgagagcg gctgtttctc aggaagcgca     300
gtcgaatata acggcgacct cgctttaatc tatactgggc ataatatgat agatgaagag     360
aaagacgatt tctaccaaac tcagaatata gcagtcagca agacggtat cgtctttgaa      420
aaactgaaag aaaaccctgt tattgcagag ccgccggaag acagcgcacg tcactttcgc     480
gatccaaaag tatggaagca tcgtgagaac tggtatatgg tggtcggaaa ctcctcaaaa     540
gagaacgtcg gcgggtcat cttataccgc tcgcctaact tgtagattg ggagtacgta       600
ggcgttctcg cccaaagcga cggaaatctc ggctttatgt gggaatgtcc ggatttcttt     660
gaactagacg gcaaacacat tttgctgatt cccctcagg gtatagaggc tgatggtgaa      720
tcatatcaaa atctgtatca aacaggctat ttgattggag actatgatga agaaacgaat     780
gagtttgtac atggctcctt taaagagttg gatcacggcc acgactttta tgccgtgcaa     840
actttattgg atgacaaagg ccgcagaatt gcgattggct ggatggatat gtgggagtca     900
gagatgccga cgaaagcaga cggatggtgc ggggcattaa ctttgccgcg tgaattgacg     960
ttgaaggatg tcacaaaat tttaatgaat cccgtcagg agactaaatt acttcgtgga     1020
tcggaacatc atgagtgtga caatcaatcg atttccggca gctatttat aaagacagcc    1080
```

```
gaaaagcttc ttgaagtggt ggccgttttt gatttgacaa tttgcagtgc cgaaacggtt       1140
ggcttaaaga tccggggaat tgaacaggaa gaaacaacca tcaagtacag cttgattgat       1200
caaaagctga cgctcgactg ttcaaagtcc ggcaaagcga gggacggtgt gagaaacgta       1260
cggcttgaag cggatgagaa gctcactttg catctgtttc tcgacagatc gtctattgaa       1320
gtatttgcaa atcatggtga agcgacaatg acaagccgca tatatccgaa ggaaggaaga       1380
gcggggattg agctgttttc tgagaaaggc aacgtacggg ttgaagaatt cacttactgg       1440
acgttgaaag atatttggaa aggtgatgaa gccaaatga                             1479
```

<210> SEQ ID NO 26
<211> LENGTH: 492
<212> TYPE: PRT
<213> ORGANISM: Bacillus licheniformis

<400> SEQUENCE: 26

```
Met Asn Arg Ile Gln Gln Ala Glu Glu Ala Leu Lys Lys Ala Gly Lys
  1               5                  10                  15

Lys Val Asn Arg Arg Tyr Arg Met Gly Tyr His Met Met Pro Arg Ala
             20                  25                  30

Asn Trp Ile Asn Asp Pro Asn Gly Leu Ile Gln Tyr Lys Gly Glu Tyr
         35                  40                  45

His Val Phe Tyr Gln His Pro Tyr Asp Glu Asn Trp Gly Pro Met
     50                  55                  60

His Trp Gly His Leu Lys Ser Lys Asp Leu Ile His Trp Glu His Leu
 65                  70                  75                  80

Pro Val Ala Leu Ala Pro Gly Asp Glu Phe Asp Glu Ser Gly Cys Phe
                 85                  90                  95

Ser Gly Ser Ala Val Glu Tyr Asn Gly Asp Leu Ala Leu Ile Tyr Thr
            100                 105                 110

Gly His Asn Met Ile Asp Glu Glu Lys Asp Asp Phe Tyr Gln Thr Gln
        115                 120                 125

Asn Ile Ala Val Ser Lys Asp Gly Ile Val Phe Glu Lys Leu Lys Glu
    130                 135                 140

Asn Pro Val Ile Ala Glu Pro Pro Glu Asp Ser Ala Arg His Phe Arg
145                 150                 155                 160

Asp Pro Lys Val Trp Lys His Arg Glu Asn Trp Tyr Met Val Val Gly
                165                 170                 175

Asn Ser Ser Lys Glu Asn Val Gly Arg Val Ile Leu Tyr Arg Ser Pro
            180                 185                 190

Asn Phe Val Asp Trp Glu Tyr Val Gly Val Leu Ala Gln Ser Asp Gly
        195                 200                 205

Asn Leu Gly Phe Met Trp Glu Cys Pro Asp Phe Phe Glu Leu Asp Gly
    210                 215                 220

Lys His Ile Leu Leu Ile Ser Pro Gln Gly Ile Glu Ala Asp Gly Glu
225                 230                 235                 240

Ser Tyr Gln Asn Leu Tyr Gln Thr Gly Tyr Leu Ile Gly Asp Tyr Asp
                245                 250                 255

Glu Glu Thr Asn Glu Phe Val His Gly Ser Phe Lys Glu Leu Asp His
            260                 265                 270

Gly His Asp Phe Tyr Ala Val Gln Thr Leu Leu Asp Lys Gly Arg
        275                 280                 285

Arg Ile Ala Ile Gly Trp Met Asp Met Trp Glu Ser Glu Met Pro Thr
    290                 295                 300
```

Lys Ala Asp Gly Trp Cys Gly Ala Leu Thr Leu Pro Arg Glu Leu Thr
305                 310                 315                 320

Leu Lys Asp Gly His Lys Ile Leu Met Asn Pro Val Glu Glu Thr Lys
                325                 330                 335

Leu Leu Arg Gly Ser Glu His His Glu Cys Asp Asn Gln Ser Ile Ser
            340                 345                 350

Gly Ser Tyr Phe Ile Lys Thr Ala Glu Lys Leu Leu Glu Val Val Ala
        355                 360                 365

Val Phe Asp Leu Thr Ile Cys Ser Ala Glu Thr Val Gly Leu Lys Ile
370                 375                 380

Arg Gly Ile Glu Gln Glu Thr Thr Ile Lys Tyr Ser Leu Ile Asp
385                 390                 395                 400

Gln Lys Leu Thr Leu Asp Cys Ser Lys Ser Gly Lys Ala Arg Asp Gly
                405                 410                 415

Val Arg Asn Val Arg Leu Glu Ala Asp Glu Lys Leu Thr Leu His Leu
            420                 425                 430

Phe Leu Asp Arg Ser Ser Ile Glu Val Phe Ala Asn His Gly Glu Ala
        435                 440                 445

Thr Met Thr Ser Arg Ile Tyr Pro Lys Glu Gly Arg Ala Gly Ile Glu
    450                 455                 460

Leu Phe Ser Glu Lys Gly Asn Val Arg Val Glu Glu Phe Thr Tyr Trp
465                 470                 475                 480

Thr Leu Lys Asp Ile Trp Lys Gly Asp Glu Ala Lys
                485                 490

<210> SEQ ID NO 27
<211> LENGTH: 1248
<212> TYPE: DNA
<213> ORGANISM: Escherichia coli

<400> SEQUENCE: 27
atggcactga atattccatt cagaaatgcg tactatcgtt ttgcatccag ttactcattt      60 ctcttttta tttcctggtc gctgtggtgg tcgttatacg ctatttggct gaaaggacat     120
ctaggattaa cagggacgga attaggtaca ctttattcgg tcaaccagtt taccagcatt     180
ctatttatga tgttctacgg catcgttcag gataaactcg gtctgaagaa accgctcatc     240
tggtgtatga gtttcattct ggtcttgacc ggaccgttta tgatttacgt ttatgaaccg     300
ttactgcaaa gcaattttc tgtaggtcta attctggggg cgctcttttt tggcctgggg     360
tatctggcgg gatgcggttt gcttgacagc ttcaccgaaa aaatggcgcg aaattttcat     420
ttcgaatatg aacagcgcg cgcctgggga tcttttggct atgctattgg cgcgttcttt     480
gccggtatat tttttagtat cagtccccat atcaacttct ggttggtctc gctatttggc     540
gctgtattta tgatgatcaa catgcgtttt aaagataagg atcaccagtg catagcggcg     600
gatgcgggag gggtaaaaaa agaggatttt atcgcagttt tcaaggatcg aaacttctgg     660
gttttcgtca tatttattgt ggggacgtgg tctttctata acatttttga tcaacaactc     720
tttcctgtct tttatgcagg tttattcgaa tcacacgatg taggaacgcg cctgtatggt     780
tatctcaact cattccaggt ggtactcgaa gcgctgtgca tggcgattat ccttttcttt     840
gtgaatcggg tagggccaaa aaatgcatta cttatcggtg ttgtgattat ggcgttgcgt     900
atcctttcct gcgcgttgtt cgttaacccc tggattattt cattagtgaa gctgttacat     960
gccattgagg ttccactttg tgtcatatcc gtcttcaaat acagcgtggc aaactttgat    1020
aagcgcctgt cgtcgacgat ctttctgatt ggttttcaaa ttgccagttc gcttgggatt    1080

```
gtgctgcttt caacgccgac tgggatactc tttgaccacg caggctacca gacagttttc    1140
ttcgcaattt cgggtattgt ctgcctgatg ttgctatttg gcattttctt cctgagtaaa    1200
aaacgcgagc aaatagttat ggaaacgcct gtaccttcag caatatag                 1248
```

<210> SEQ ID NO 28
<211> LENGTH: 415
<212> TYPE: PRT
<213> ORGANISM: Escherichia coli

<400> SEQUENCE: 28

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Ile Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ala Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350
```

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
    370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
            405                 410                 415

<210> SEQ ID NO 29
<211> LENGTH: 1434
<212> TYPE: DNA
<213> ORGANISM: Escherichia coli

<400> SEQUENCE: 29

```
atgacgcaat ctcgattgca tgcggcgcaa aacgcactag caaaacttca cgagcgccga      60
ggtaacactt tctatcccca ttttcacctc gcgcctcctg ccgggtggat gaacgatcca     120
aacggcctga tctggtttaa cgatcgttat cacgcgtttt atcaacatca cccgatgagc     180
gaacactggg ggccaatgca ctggggacat gccaccagcg acgatatgat ccactggcag     240
catgagccta ttgcgctagc gccaggagac gagaatgaca agacggggtg tttttcaggt     300
agtgctgtcg atgacaatgg tgtcctctca cttatctaca ccggacacgt ctggctcgat     360
ggtgcaggta atgacgatgc aattcgcgaa gtacaatgtc tggctaccag tcgggatggt     420
attcatttcg agaaacaggg tgtgatcctc actccaccag aaggcatcat gcacttccgc     480
gatcctaaag tgtggcgtga agccgacaca tggtggatgg tagtcggggc gaaagaccca     540
ggcaacacgg ggcagatcct gctttatcgc ggcagttcat tgcgtgaatg gactttcgat     600
cgcgtactgg cccacgctga tgcgggtgaa agctatatgt gggaatgtcc ggactttttc     660
agccttggcg atcagcatta tctgatgttt tccccgcagg gaatgaatgc cgagggatac     720
agttatcgaa atcgctttca aagtggcgta atacccggaa tgtggtcgcc aggacgactt     780
tttgcacaat ccgggcattt tactgaactt gataacgggc atgactttta tgcaccacaa     840
agctttgtag cgaaggatgg tcggcgtatt gttatcggct ggatggatat gtgggaatcg     900
ccaatgccct caaaacgtga aggctgggca ggctgcatga cgctggcgcg cgagctatca     960
gagagcaatg gcaaactcct acaacgcccg gtacacgaag ctgagtcgtt acgccagcag    1020
catcaatcta tctctccccg cacaatcagc aataaatatg ttttgcagga aaacgcgcaa    1080
gcagttgaga ttcagttgca gtgggcgctg aagaacagtg atgccgaaca ttacggatta    1140
cagctcggcg ctggaatgcg gctgtatatt gataaccaat ctgagcgact tgttttgtgg    1200
cggtattacc cacacgagaa tttagatggc taccgtagta ttccccctccc gcagggtgac    1260
atgctcgccc taaggatatt tatcgataca tcatccgtgg aagtatttat taacgacggg    1320
gaggcggtga tgagtagccg aatatatccg cagccagaag aacgggaact gtcgctctat    1380
gcctcccacg gagtggctgt gctgcaacat ggagcactct ggcaactggg ttaa           1434
```

<210> SEQ ID NO 30
<211> LENGTH: 477
<212> TYPE: PRT
<213> ORGANISM: Escherichia coli

<400> SEQUENCE: 30

Met Thr Gln Ser Arg Leu His Ala Ala Gln Asn Ala Leu Ala Lys Leu
1               5                   10                  15

His Glu Arg Arg Gly Asn Thr Phe Tyr Pro His Phe His Leu Ala Pro

-continued

```
                20                  25                  30
Pro Ala Gly Trp Met Asn Asp Pro Asn Gly Leu Ile Trp Phe Asn Asp
             35                  40                  45
Arg Tyr His Ala Phe Tyr Gln His His Pro Met Ser Glu His Trp Gly
         50                  55                  60
Pro Met His Trp Gly His Ala Thr Ser Asp Asp Met Ile His Trp Gln
65                  70                  75                  80
His Glu Pro Ile Ala Leu Ala Pro Gly Asp Glu Asn Asp Lys Asp Gly
                 85                  90                  95
Cys Phe Ser Gly Ser Ala Val Asp Asp Asn Gly Val Leu Ser Leu Ile
            100                 105                 110
Tyr Thr Gly His Val Trp Leu Asp Gly Ala Gly Asn Asp Asp Ala Ile
        115                 120                 125
Arg Glu Val Gln Cys Leu Ala Thr Ser Arg Asp Gly Ile His Phe Glu
    130                 135                 140
Lys Gln Gly Val Ile Leu Thr Pro Pro Glu Gly Ile Met His Phe Arg
145                 150                 155                 160
Asp Pro Lys Val Trp Arg Glu Ala Asp Thr Trp Trp Met Val Val Gly
                165                 170                 175
Ala Lys Asp Pro Gly Asn Thr Gly Gln Ile Leu Leu Tyr Arg Gly Ser
            180                 185                 190
Ser Leu Arg Glu Trp Thr Phe Asp Arg Val Leu Ala His Ala Asp Ala
        195                 200                 205
Gly Glu Ser Tyr Met Trp Glu Cys Pro Asp Phe Phe Ser Leu Gly Asp
    210                 215                 220
Gln His Tyr Leu Met Phe Ser Pro Gln Gly Met Asn Ala Glu Gly Tyr
225                 230                 235                 240
Ser Tyr Arg Asn Arg Phe Gln Ser Gly Val Ile Pro Gly Met Trp Ser
                245                 250                 255
Pro Gly Arg Leu Phe Ala Gln Ser Gly His Phe Thr Glu Leu Asp Asn
            260                 265                 270
Gly His Asp Phe Tyr Ala Pro Gln Ser Phe Val Ala Lys Asp Gly Arg
        275                 280                 285
Arg Ile Val Ile Gly Trp Met Asp Met Trp Glu Ser Pro Met Pro Ser
    290                 295                 300
Lys Arg Glu Gly Trp Ala Gly Cys Met Thr Leu Ala Arg Glu Leu Ser
305                 310                 315                 320
Glu Ser Asn Gly Lys Leu Leu Gln Arg Pro Val His Glu Ala Glu Ser
                325                 330                 335
Leu Arg Gln Gln His Gln Ser Ile Ser Pro Arg Thr Ile Ser Asn Lys
            340                 345                 350
Tyr Val Leu Gln Glu Asn Ala Gln Ala Val Glu Ile Gln Leu Gln Trp
        355                 360                 365
Ala Leu Lys Asn Ser Asp Ala His Tyr Gly Leu Gln Leu Gly Ala
    370                 375                 380
Gly Met Arg Leu Tyr Ile Asp Asn Gln Ser Glu Arg Leu Val Leu Trp
385                 390                 395                 400
Arg Tyr Tyr Pro His Glu Asn Leu Asp Gly Tyr Arg Ser Ile Pro Leu
                405                 410                 415
Pro Gln Gly Asp Met Leu Ala Leu Arg Ile Phe Ile Asp Thr Ser Ser
            420                 425                 430
Val Glu Val Phe Ile Asn Asp Gly Glu Ala Val Met Ser Ser Arg Ile
        435                 440                 445
```

Tyr Pro Gln Pro Glu Glu Arg Glu Leu Ser Leu Tyr Ala Ser His Gly
    450                 455                 460

Val Ala Val Leu Gln His Gly Ala Leu Trp Gln Leu Gly
465                 470                 475

<210> SEQ ID NO 31
<211> LENGTH: 927
<212> TYPE: DNA
<213> ORGANISM: Agrobacterium tumefaciens

<400> SEQUENCE: 31

```
atgatcctgt gttgtggtga agccctgatc gacatgctgc cccggcagac gacgctgggt    60
gaggcgggct ttgccccta cgcaggcgga gcggtcttca acacggcaat tgcgctgggg   120
cgtcttggcg tcccttcagc ctttttacc ggtctttccg acgacatgat gggcgatatc   180
ctgcgggaga ccctgcgggc cagcaaggtg gatttcagct attgcgccac cctgtcgcgc   240
cccaccacca ttgcgttcgt taagctggtt gatggccatg cgacctacgc ttttacgac   300
gagaacaccg ccggccggat gatcaccgag gccgaacttc cggccttggg agcggattgc   360
gaagcgctgc atttcggcgc catcagcctt attcccgaac cctgcggcag cacctatgag   420
gcgctgatga cgcgcgagca tgagacccgc gtcatctcgc tcgatccgaa cattcgtccc   480
ggcttcatcc agaacaagca gtcgcacatg cccgcatcc gccgcatggc ggcgatgtct   540
gacatcgtca agttctcgga tgaggacctg gcgtggttcg gtctggaagg cgacgaggac   600
acgcttgccc gccactggct gcaccacggt gcaaaactcg tcgttgtcac ccgtggcgcc   660
aagggtgccg tgggttacag cgccaatctc aaggtggaag tggcctccga gcgcgtcgaa   720
gtggtcgata cggtcggcgc cggcgatacg ttcgatgccg gcattcttgc ttcgctgaaa   780
atgcagggcc tgctgaccaa agcgcaggtg gcttcgctga gcgaagagca gatcagaaaa   840
gcttttggcgc ttggcgcgaa agccgctgcg gtcactgtct cgcgggctgg cgcaaatccg   900
cctttcgcgc atgaaatcgg tttgtga                                       927
```

<210> SEQ ID NO 32
<211> LENGTH: 308
<212> TYPE: PRT
<213> ORGANISM: Agrobacterium tumefaciens

<400> SEQUENCE: 32

Met Ile Leu Cys Cys Gly Glu Ala Leu Ile Asp Met Leu Pro Arg Gln
1               5                   10                  15

Thr Thr Leu Gly Glu Ala Gly Phe Ala Pro Tyr Ala Gly Gly Ala Val
                20                  25                  30

Phe Asn Thr Ala Ile Ala Leu Gly Arg Leu Gly Val Pro Ser Ala Phe
            35                  40                  45

Phe Thr Gly Leu Ser Asp Asp Met Met Gly Asp Ile Leu Arg Glu Thr
        50                  55                  60

Leu Arg Ala Ser Lys Val Asp Phe Ser Tyr Cys Ala Thr Leu Ser Arg
65                  70                  75                  80

Pro Thr Thr Ile Ala Phe Val Lys Leu Val Asp Gly His Ala Thr Tyr
                85                  90                  95

Ala Phe Tyr Asp Glu Asn Thr Ala Gly Arg Met Ile Thr Glu Ala Glu
            100                 105                 110

Leu Pro Ala Leu Gly Ala Asp Cys Glu Ala Leu His Phe Gly Ala Ile
        115                 120                 125

Ser Leu Ile Pro Glu Pro Cys Gly Ser Thr Tyr Glu Ala Leu Met Thr
    130                 135                 140

```
Arg Glu His Glu Thr Arg Val Ile Ser Leu Asp Pro Asn Ile Arg Pro
145                 150                 155                 160

Gly Phe Ile Gln Asn Lys Gln Ser His Met Ala Arg Ile Arg Arg Met
            165                 170                 175

Ala Ala Met Ser Asp Ile Val Lys Phe Ser Asp Glu Asp Leu Ala Trp
        180                 185                 190

Phe Gly Leu Glu Gly Asp Glu Asp Thr Leu Ala Arg His Trp Leu His
    195                 200                 205

His Gly Ala Lys Leu Val Val Thr Arg Gly Ala Lys Gly Ala Val
    210                 215                 220

Gly Tyr Ser Ala Asn Leu Lys Val Glu Val Ala Ser Glu Arg Val Glu
225                 230                 235                 240

Val Val Asp Thr Val Gly Ala Gly Asp Thr Phe Asp Ala Gly Ile Leu
                245                 250                 255

Ala Ser Leu Lys Met Gln Gly Leu Leu Thr Lys Ala Gln Val Ala Ser
            260                 265                 270

Leu Ser Glu Glu Gln Ile Arg Lys Ala Leu Ala Leu Gly Ala Lys Ala
        275                 280                 285

Ala Ala Val Thr Val Ser Arg Ala Gly Ala Asn Pro Pro Phe Ala His
    290                 295                 300

Glu Ile Gly Leu
305

<210> SEQ ID NO 33
<211> LENGTH: 1404
<212> TYPE: DNA
<213> ORGANISM: Streptococcus mutans

<400> SEQUENCE: 33
cagctgatta tgcgtcagtt gaaaccctcg cttcttcagg aactgttgct gtaggtgata      60
gcttacttga agttaaaaaa taagaaatat tatcagaaag accgtaaggt cttttttgact   120 gcttaaaaga ttcagtaaca atagtattaa agccttttgg ctaactaata cttgaaattt    180
agcaaattat gatataatgt taagtagtcc ttaagggtag attaagggta ttcaaatcca    240
aaaattgatt tggtaagtta agtaaaatat aagaggttta ttatgtctaa attatatggc    300
agcatcgaag ctggcggaac aaaatttgtc tgtgctgtag gtgatgaaaa ttttcaaatt    360
ttagaaaaag ttcagttccc aacaacaaca ccttatgaaa caatagaaaa aacagttgct    420
ttctttaaaa aatttgaagc tgatttagcc agtgttgcca ttggttcttt tggccctatt    480
gatattgatc aaaattcaga cacttatggt tacattactt caacaccaaa gccaaactgg    540
gctaacgttg attttgtcgg cttaatttct aaagattta aaattccatt ttactttacg    600
acagatgtta attcttctgc ttatggggaa acaattgctc gttcaaatgt taaaagtctg    660
gtttattata ctattggaac aggcattgga gcagggcta ttcaaaatgg cgaattcatt    720
ggcggtatgg gacatacgga agctggacac gtttacatgg ctccgcatcc caatgatgtt    780
catcatggtt ttgtaggcac ctgtcctttc cataaaggct gtttagaagg acttgcagcg    840
ggtcctagct tagaggctcg tactggtatt cgtggtgagt taattgagca aaactcagaa    900
gtttgggata ttcaggcata ctacattgct caggcggcta ttcaagcgac tgtcctttat    960
cgtccgcaag tcattgtatt tggcggaggc gttatggcac aagaacatat gctcaatcgg   1020
gttcgtgaaa aatttacttc acttttgaat gactatcttc cagttccaga tgttaaagat   1080
tatattgtga caccagctgt tgcagaaaat ggttcagcaa cattgggaaa tctcgcttta   1140
```

-continued

```
gctaaaaaga tagcagcgcg ttaattaaaa atgaattgga agattaaagc accttctaat    1200
attcaatatt aaactgttag aatttacgtg aacgaaattt tcattttatg aggataatga    1260
agtgaatata attactcttg atttcctctg aaactagata gtggtatatt gaaaaacaga    1320
aaggagaaca ctatggaagg acctttgttt tacaatcac aaatgcataa aaaaatctgg     1380
ggcggcaatc ggctcagaaa agaa                                           1404
```

<210> SEQ ID NO 34
<211> LENGTH: 293
<212> TYPE: PRT
<213> ORGANISM: Streptococcus mutans

<400> SEQUENCE: 34

```
Met Ser Lys Leu Tyr Gly Ser Ile Glu Ala Gly Gly Thr Lys Phe Val
1               5                  10                  15

Cys Ala Val Gly Asp Glu Asn Phe Gln Ile Leu Glu Lys Val Gln Phe
            20                  25                  30

Pro Thr Thr Thr Pro Tyr Glu Thr Ile Glu Lys Thr Val Ala Phe Phe
        35                  40                  45

Lys Lys Phe Glu Ala Asp Leu Ala Ser Val Ala Ile Gly Ser Phe Gly
    50                  55                  60

Pro Ile Asp Ile Asp Gln Asn Ser Asp Thr Tyr Gly Tyr Ile Thr Ser
65                  70                  75                  80

Thr Pro Lys Pro Asn Trp Ala Asn Val Asp Phe Val Gly Leu Ile Ser
                85                  90                  95

Lys Asp Phe Lys Ile Pro Phe Tyr Phe Thr Thr Asp Val Asn Ser Ser
            100                 105                 110

Ala Tyr Gly Glu Thr Ile Ala Arg Ser Asn Val Lys Ser Leu Val Tyr
        115                 120                 125

Tyr Thr Ile Gly Thr Gly Ile Gly Ala Gly Ala Ile Gln Asn Gly Glu
    130                 135                 140

Phe Ile Gly Gly Met Gly His Thr Glu Ala Gly His Val Tyr Met Ala
145                 150                 155                 160

Pro His Pro Asn Asp Val His His Gly Phe Val Gly Thr Cys Pro Phe
                165                 170                 175

His Lys Gly Cys Leu Glu Gly Leu Ala Ala Gly Pro Ser Leu Glu Ala
            180                 185                 190

Arg Thr Gly Ile Arg Gly Glu Leu Ile Glu Gln Asn Ser Glu Val Trp
        195                 200                 205

Asp Ile Gln Ala Tyr Tyr Ile Ala Gln Ala Ala Ile Gln Ala Thr Val
    210                 215                 220

Leu Tyr Arg Pro Gln Val Ile Val Phe Gly Gly Gly Val Met Ala Gln
225                 230                 235                 240

Glu His Met Leu Asn Arg Val Arg Glu Lys Phe Thr Ser Leu Leu Asn
                245                 250                 255

Asp Tyr Leu Pro Val Pro Asp Val Lys Asp Tyr Ile Val Thr Pro Ala
            260                 265                 270

Val Ala Glu Asn Gly Ser Ala Thr Leu Gly Asn Leu Ala Leu Ala Lys
        275                 280                 285

Lys Ile Ala Ala Arg
    290
```

<210> SEQ ID NO 35
<211> LENGTH: 915
<212> TYPE: DNA
<213> ORGANISM: Escherichia coli

<400> SEQUENCE: 35

```
atgtcagcca aagtatgggt tttaggggat gcggtcgtag atctcttgcc agaatcagac        60
gggcgcctac tgccttgtcc tggcggcgcg ccagctaacg ttgcggtggg aatcgccaga       120
ttaggcggaa caagtgggtt tataggtcgg gtggggatg atccttttgg tgcgttaatg        180
caaagaacgc tgctaactga gggagtcgat atcacgtatc tgaagcaaga tgaatggcac       240
cggacatcca cggtgcttgt cgatctgaac gatcaagggg aacgttcatt tacgtttatg       300
gtccgcccca gtgccgatct ttttttagag acgacagact tgccctgctg gcgacatggc       360
gaatggttac atctctgttc aattgcgttg tctgccgagc cttgcgtac cagcgcattt        420
actgcgatga cggcgatccg gcatgccgga ggttttgtca gcttcgatcc taatattcgt       480
gaagatctat ggcaagacga gcatttgctc cgcttgtgtt gcggcaggc gctacaactg        540
gcggatgtcg tcaagctctc ggaagaagaa tggcgactta tcagtggaaa aacacagaac       600
gatcaggata tatgcgccct ggcaaaagag tatgagatcg ccatgctgtt ggtgactaaa       660
ggtgcagaag gggtggtggt ctgttatcga ggacaagttc accattttgc tggaatgtct       720
gtgaattgtg tcgatagcac gggggcggga gatgcgttcg ttgccgggtt actcacaggt       780
ctgtcctcta cgggattatc tacagatgag agagaaatgc gacgaattat cgatctcgct       840
caacgttgcg gagcgcttgc agtaacggcg aaggggcaa tgacagcgct gccatgtcga        900
caagaactgg aatag                                                        915
```

<210> SEQ ID NO 36
<211> LENGTH: 304
<212> TYPE: PRT
<213> ORGANISM: Escherichia coli

<400> SEQUENCE: 36

```
Met Ser Ala Lys Val Trp Val Leu Gly Asp Ala Val Val Asp Leu Leu
1               5                   10                  15

Pro Glu Ser Asp Gly Arg Leu Leu Pro Cys Pro Gly Gly Ala Pro Ala
            20                  25                  30

Asn Val Ala Val Gly Ile Ala Arg Leu Gly Gly Thr Ser Gly Phe Ile
        35                  40                  45

Gly Arg Val Gly Asp Asp Pro Phe Gly Ala Leu Met Gln Arg Thr Leu
    50                  55                  60

Leu Thr Glu Gly Val Asp Ile Thr Tyr Leu Lys Gln Asp Glu Trp His
65                  70                  75                  80

Arg Thr Ser Thr Val Leu Val Asp Leu Asn Asp Gln Gly Glu Arg Ser
                85                  90                  95

Phe Thr Phe Met Val Arg Pro Ser Ala Asp Leu Phe Leu Glu Thr Thr
            100                 105                 110

Asp Leu Pro Cys Trp Arg His Gly Glu Trp Leu His Leu Cys Ser Ile
        115                 120                 125

Ala Leu Ser Ala Glu Pro Ser Arg Thr Ser Ala Phe Thr Ala Met Thr
    130                 135                 140

Ala Ile Arg His Ala Gly Gly Phe Val Ser Phe Asp Pro Asn Ile Arg
145                 150                 155                 160

Glu Asp Leu Trp Gln Asp Glu His Leu Leu Arg Leu Cys Leu Arg Gln
                165                 170                 175

Ala Leu Gln Leu Ala Asp Val Val Lys Leu Ser Glu Glu Trp Arg
            180                 185                 190

Leu Ile Ser Gly Lys Thr Gln Asn Asp Gln Asp Ile Cys Ala Leu Ala
```

```
                195                 200                 205
Lys Glu Tyr Glu Ile Ala Met Leu Leu Val Thr Lys Gly Ala Glu Gly
            210                 215                 220

Val Val Val Cys Tyr Arg Gly Gln Val His His Phe Ala Gly Met Ser
225                 230                 235                 240

Val Asn Cys Val Asp Ser Thr Gly Ala Gly Asp Ala Phe Val Ala Gly
                245                 250                 255

Leu Leu Thr Gly Leu Ser Ser Thr Gly Leu Ser Thr Asp Glu Arg Glu
            260                 265                 270

Met Arg Arg Ile Ile Asp Leu Ala Gln Arg Cys Gly Ala Leu Ala Val
            275                 280                 285

Thr Ala Lys Gly Ala Met Thr Ala Leu Pro Cys Arg Gln Glu Leu Glu
            290                 295                 300
```

<210> SEQ ID NO 37
<211> LENGTH: 924
<212> TYPE: DNA
<213> ORGANISM: Klebsiella pneumoniae

<400> SEQUENCE: 37

```
atgaatggaa aaatctgggt actcggcgat gcggtcgtcg atctcctgcc cgatggagag      60
ggccgcctgc tgcaatgccc cggcggcgcg ccggccaacg tggcggtcgg cgtggcgcgg     120
ctcggcggtg acagcgggtt tatcggccgc gtcggcgacg atcccttcgg ccgtttttatg    180
cgtcacaccc tggcgcagga gcaagtggat gtgaactata tgcgcctcga tgcggcgcag     240
cgcacctcca cggtggtggt cgatctcgat agccacgggg agcgcacctt tacctttatg     300
gtccgtccga gcgccgacct gttccttcag cccgaggatc tcccgccgtt tgccgccggt     360
cagtggctgc acgtctgctc catcgctctc agcgcggagc cgagccgcag cacgacattc     420
gcggcgatgg aggcgataaa gcgccggggg gctatgtca gcttcgaccc caatatccgc      480
agcgacctgt ggcaggatcc gcaggacctt cgcgactgtc tcgaccgggc gctggccctc     540
gccgacgcca taaaactttc ggaagaggag ctggcgttta tcagcggcag cgacgacatc     600
gtcagcggca ccgcccggct gaacgccgc ttccagccga cgctactgct ggtgacccag      660
ggtaaagcgg ggtccaggc cgccctgcgc gggcaggtta gccacttccc tgcccgcccg      720
gtggtggccg tcgataccac cggcgccggc gatgcctttg tcgccgggct actcgccggc     780
ctcgccgccc acggtatccc ggacaacctc gcagccctgg ctcccgacct cgcgctggcg     840
caaacctgcg cgcccctggc caccaccgcc aaaggcgcca tgaccgccct gccctacagg     900
gacgatcttc agcgctcgct gtga                                            924
```

<210> SEQ ID NO 38
<211> LENGTH: 307
<212> TYPE: PRT
<213> ORGANISM: Klebsiella pneumoniae

<400> SEQUENCE: 38

```
Met Asn Gly Lys Ile Trp Val Leu Gly Asp Ala Val Val Asp Leu Leu
1               5                   10                  15

Pro Asp Gly Glu Gly Arg Leu Leu Gln Cys Pro Gly Gly Ala Pro Ala
            20                  25                  30

Asn Val Ala Val Gly Val Ala Arg Leu Gly Gly Asp Ser Gly Phe Ile
        35                  40                  45

Gly Arg Val Gly Asp Asp Pro Phe Gly Arg Phe Met Arg His Thr Leu
    50                  55                  60
```

```
Ala Gln Glu Gln Val Asp Val Asn Tyr Met Arg Leu Asp Ala Ala Gln
 65                  70                  75                  80

Arg Thr Ser Thr Val Val Asp Leu Asp Ser His Gly Glu Arg Thr
                 85                  90                  95

Phe Thr Phe Met Val Arg Pro Ser Ala Asp Leu Phe Leu Gln Pro Glu
            100                 105                 110

Asp Leu Pro Pro Phe Ala Ala Gly Gln Trp Leu His Val Cys Ser Ile
        115                 120                 125

Ala Leu Ser Ala Glu Pro Ser Arg Ser Thr Thr Phe Ala Ala Met Glu
    130                 135                 140

Ala Ile Lys Arg Ala Gly Gly Tyr Val Ser Phe Asp Pro Asn Ile Arg
145                 150                 155                 160

Ser Asp Leu Trp Gln Asp Pro Gln Asp Leu Arg Asp Cys Leu Asp Arg
                165                 170                 175

Ala Leu Ala Leu Ala Asp Ala Ile Lys Leu Ser Glu Glu Glu Leu Ala
            180                 185                 190

Phe Ile Ser Gly Ser Asp Asp Ile Val Ser Gly Thr Ala Arg Leu Asn
        195                 200                 205

Ala Arg Phe Gln Pro Thr Leu Leu Leu Val Thr Gln Gly Lys Ala Gly
    210                 215                 220

Val Gln Ala Ala Leu Arg Gly Gln Val Ser His Phe Pro Ala Arg Pro
225                 230                 235                 240

Val Val Ala Val Asp Thr Thr Gly Ala Gly Asp Ala Phe Val Ala Gly
                245                 250                 255

Leu Leu Ala Gly Leu Ala Ala His Gly Ile Pro Asp Asn Leu Ala Ala
            260                 265                 270

Leu Ala Pro Asp Leu Ala Leu Ala Gln Thr Cys Gly Ala Leu Ala Thr
        275                 280                 285

Thr Ala Lys Gly Ala Met Thr Ala Leu Pro Tyr Arg Asp Asp Leu Gln
    290                 295                 300

Arg Ser Leu
305

<210> SEQ ID NO 39
<211> LENGTH: 915
<212> TYPE: DNA
<213> ORGANISM: Escherichia coli

<400> SEQUENCE: 39
atgtcagcca aagtatgggt tttaggggat gcggtcgtag atctcttgcc agaatcagac      60
gggcgcctac tgccttgtcc tggcggcgcg ccagctaacg ttgcggtggg aatcgccaga     120
ttaggcggaa caagtgggtt tataggtcgg gtggggatg atcctttttgg tgcgttaatg     180 caaagaacgc tgctaactga gggagtcgat atcacgtatc tgaagcaaga tgaatggcac     240
cggacatcca cggtgcttgt cgatctgaac gatcaagggg aacgttcatt tacgtttatg     300
gtccgcccca gtgccgatct ttttttagag acgacagact tgccctgctg gcgacatggc     360
gaatggttac atctctgttc aattgcgttg tctgccgagc cttcgcgtac cagcgcattt     420
actgcgatga cggcgatccg gcatgccgga ggttttgtca gcttcgatcc taatattcgt     480
gaagatctat ggcaagacga gcatttgctc cgcttgtgtt tgcggcaggc gctacaactg     540
gcggatgtcg tcaagctctc ggaagaagaa tggcgactta tcagtggaaa acacagaac      600 gatcaggata tatgcgccct ggcaaaagag tatgagatcg ccatgctgtt ggtgactaaa     660
ggtgcagaag gggtggtggt ctgttatcga ggacaagttc accattttgc tggaatgtct     720
```

-continued

```
gtgaattgtg tcgatagcac gggggcggga gatgcgttcg ttgccgggtt actcacaggt    780
ctgtcctcta cgggattatc tacagatgag agagaaatgc gacgaattat cgatctcgct    840
caacgttgcg gagcgcttgc agtaacggcg aaagggcaa tgacagcgct gccatgtcga    900
caagaactgg aatag                                                     915
```

<210> SEQ ID NO 40
<211> LENGTH: 304
<212> TYPE: PRT
<213> ORGANISM: Escherichia coli

<400> SEQUENCE: 40

Met Ser Ala Lys Val Trp Val Leu Gly Asp Ala Val Val Asp Leu Leu
1               5                   10                  15

Pro Glu Ser Asp Gly Arg Leu Leu Pro Cys Pro Gly Gly Ala Pro Ala
            20                  25                  30

Asn Val Ala Val Gly Ile Ala Arg Leu Gly Gly Thr Ser Gly Phe Ile
        35                  40                  45

Gly Arg Val Gly Asp Asp Pro Phe Gly Ala Leu Met Gln Arg Thr Leu
    50                  55                  60

Leu Thr Glu Gly Val Asp Ile Thr Tyr Leu Lys Gln Asp Glu Trp His
65                  70                  75                  80

Arg Thr Ser Thr Val Leu Val Asp Leu Asn Asp Gln Gly Glu Arg Ser
                85                  90                  95

Phe Thr Phe Met Val Arg Pro Ser Ala Asp Leu Phe Leu Glu Thr Thr
            100                 105                 110

Asp Leu Pro Cys Trp Arg His Gly Glu Trp Leu His Leu Cys Ser Ile
        115                 120                 125

Ala Leu Ser Ala Glu Pro Ser Arg Thr Ser Ala Phe Thr Ala Met Thr
    130                 135                 140

Ala Ile Arg His Ala Gly Gly Phe Val Ser Phe Asp Pro Asn Ile Arg
145                 150                 155                 160

Glu Asp Leu Trp Gln Asp Glu His Leu Leu Arg Leu Cys Leu Arg Gln
                165                 170                 175

Ala Leu Gln Leu Ala Asp Val Val Lys Leu Ser Glu Glu Glu Trp Arg
            180                 185                 190

Leu Ile Ser Gly Lys Thr Gln Asn Asp Gln Asp Ile Cys Ala Leu Ala
        195                 200                 205

Lys Glu Tyr Glu Ile Ala Met Leu Leu Val Thr Lys Gly Ala Glu Gly
    210                 215                 220

Val Val Val Cys Tyr Arg Gly Gln Val His His Phe Ala Gly Met Ser
225                 230                 235                 240

Val Asn Cys Val Asp Ser Thr Gly Ala Gly Asp Ala Phe Val Ala Gly
                245                 250                 255

Leu Leu Thr Gly Leu Ser Ser Thr Gly Leu Ser Thr Asp Glu Arg Glu
            260                 265                 270

Met Arg Arg Ile Ile Asp Leu Ala Gln Arg Cys Gly Ala Leu Ala Val
        275                 280                 285

Thr Ala Lys Gly Ala Met Thr Ala Leu Pro Cys Arg Gln Glu Leu Glu
    290                 295                 300

<210> SEQ ID NO 41
<211> LENGTH: 879
<212> TYPE: DNA
<213> ORGANISM: Enterococcus faecalis

<400> SEQUENCE: 41

-continued

```
atgacagaaa aacttttagg aagtatcgaa gccggtggca caaaatttgt atgtggcgtt      60
gggacagatg atttgaccat cgtagaacgt gtcagttttc ccacaacaac cccagaagaa     120
acaatgaaaa agtaataga atttttccaa caatatcctt taaaagcgat tgggattggt     180
tcatttggtc cgattgatat tcacgttgat tctcctacgt atggttatat cacttctaca     240
ccaaaattag cttggcgtaa ctttgacttg ttaggaacta tgaaacaaca ttttgatgtg     300
ccaatggctt ggacaacgga tgtgaatgct gcggcatatg gtgagtatgt tgctggaaat     360
gggcaacata catctagttg tgtatattat acaattggaa ctggtgttgg cgctggagcg     420
attcaaaacg gtgagtttat tgaaggcttt agccacccag aaatggggca tgcgttagtt     480
cgtcgtcatc ctgaagatac gtatgcagga aattgtcctt atcatggaga ttgtttagaa     540
gggattgcag caggaccagc agttgaaggt cgttctggta aaaaaggaca tttattggaa     600
gaggatcata aaacttggga attagaagct tattatttag cgcaagcggc gtacaatacg     660
actttattat tagcgccaga agtgatcatt ttaggtggcg gcgtcatgaa acaacgtcat     720
ttgatgccga agttcgtga aaaatttgct gaattagtca atggatatgt ggaaacaccg     780
cctttagaaa aatacttggt gacgcctctt ttagaagata tccaggaac aatcggttgc     840 tttgccttgg caaaaaagc tttaatggct caaaaataa                             879
```

<210> SEQ ID NO 42
<211> LENGTH: 292
<212> TYPE: PRT
<213> ORGANISM: Enterococcus faecalis

<400> SEQUENCE: 42

```
Met Thr Glu Lys Leu Leu Gly Ser Ile Glu Ala Gly Gly Thr Lys Phe
1               5                   10                  15

Val Cys Gly Val Gly Thr Asp Asp Leu Thr Ile Val Glu Arg Val Ser
                20                  25                  30

Phe Pro Thr Thr Thr Pro Glu Thr Met Lys Lys Val Ile Glu Phe
            35                  40                  45

Phe Gln Gln Tyr Pro Leu Lys Ala Ile Gly Ile Gly Ser Phe Gly Pro
        50                  55                  60

Ile Asp Ile His Val Asp Ser Pro Thr Tyr Gly Tyr Ile Thr Ser Thr
65                  70                  75                  80

Pro Lys Leu Ala Trp Arg Asn Phe Asp Leu Leu Gly Thr Met Lys Gln
                85                  90                  95

His Phe Asp Val Pro Met Ala Trp Thr Thr Asp Val Asn Ala Ala Ala
                100                 105                 110

Tyr Gly Glu Tyr Val Ala Gly Asn Gly Gln His Thr Ser Ser Cys Val
            115                 120                 125

Tyr Tyr Thr Ile Gly Thr Gly Val Gly Ala Gly Ala Ile Gln Asn Gly
        130                 135                 140

Glu Phe Ile Glu Gly Phe Ser His Pro Glu Met Gly His Ala Leu Val
145                 150                 155                 160

Arg Arg His Pro Glu Asp Thr Tyr Ala Gly Asn Cys Pro Tyr His Gly
                165                 170                 175

Asp Cys Leu Glu Gly Ile Ala Ala Gly Pro Ala Val Glu Gly Arg Ser
                180                 185                 190

Gly Lys Lys Gly His Leu Leu Glu Glu Asp His Lys Thr Trp Glu Leu
        195                 200                 205

Glu Ala Tyr Tyr Leu Ala Gln Ala Ala Tyr Asn Thr Thr Leu Leu Leu
    210                 215                 220
```

```
Ala Pro Glu Val Ile Ile Leu Gly Gly Val Met Lys Gln Arg His
225                 230                 235                 240

Leu Met Pro Lys Val Arg Glu Lys Phe Ala Glu Leu Val Asn Gly Tyr
                245                 250                 255

Val Glu Thr Pro Pro Leu Glu Lys Tyr Leu Val Thr Pro Leu Leu Glu
            260                 265                 270

Asp Asn Pro Gly Thr Ile Gly Cys Phe Ala Leu Ala Lys Lys Ala Leu
        275                 280                 285

Met Ala Gln Lys
    290

<210> SEQ ID NO 43
<211> LENGTH: 1458
<212> TYPE: DNA
<213> ORGANISM: Saccharomyces cerevisiae

<400> SEQUENCE: 43
ttaagcgcca atgataccaa gagacttacc ttcggcaatt ctttttttcgg acaatgcagc    60 aataacagca gcacctgcac ctgaaccatc ctcagctgga acaatcgtaa ttggatcttt   120
gcttgcgtca ccagtccatc catagatatc tctcaaaccc ttagcggcgg cttccttgaa   180
acctgggtat ttgttataga cagaaccgtc agcggcaatg tgaccagtct tgtaacctct   240
cttttggcaa atagcggcaa taccacaaac agctaatcta gcagctctgg taccgatcaa   300
ttcacaaagt cttctaatca acttacgttc tggcagagtg tcttgacac caaagtcctt    360 ttggaagatg tcatcagtat cttccaagtt ttcaaatgga tcatcctcga ttcttgctgg   420
gtaggaggta tccatgatgt atggttgttt caacttgctt agatcttgat ccttcaacat   480
caagcccttc tcgtttaatt caagtaacac tagacgcaac aattcaccca agtagtaacc   540
ggaggtcatc ttttcaaaag cttgttgacc aggtcttgga gattgttcgt cgacagcaac   600
atcgtacttg gttcttggca agaccaaatg ttcattatcg aaggaaccat attcacaatt   660
gatagccatt ggagagttac ttggaatatc gtctgctaat ttgccctcca acttttcgat   720
atcggaaaca acatcataga aagcaccgtt gacaccagta ccgaaaatca cacccatctt   780
agtctctggg tcagtgtagt atgaggcaat taaagtacca acagtatcat taatcaatgc   840
tacaatttca ataggcaact ctctcttgga aatttcgttt tgtagcaatg ggacgacatc   900
gtggccttcg acatttggaa tatcgaaacc cttggtccat ctttgcaaaa taccttcgtt   960
aatcttgttt tgggaagctg gtacgagaa ggtgaaacct aatggtaagg tgtccttggt   1020
gtttagcaat tcttgctcga ccataaagtc cttcaaagag tcggcaataa aggaccataa   1080
ctcctcttgg tgcttagtgg ttctcatgtc atgtggtagt ttatacttgg attgagtggt   1140
gtcaaaggta tggttaccgc tcaacttgac caacacgact cttaagttag taccacccaa   1200
atcaatggcc aaatagttac cagattcttt acctgtgggg aattccatga cccaaccggg   1260
aatcattgga atgttaccct ccttctttgt caaaccttta ttcaattcgt cgataaagtg   1320
cttaacaacc tttctcaagg tctcgctgtc aactgtaaac atatcttcca actgatgaat   1380
ttcatccatc aattccttgg gcacatcagc catggaaccc tttctagcct gtggtttctt   1440
tggacctaaa tgaaccat                                                1458

<210> SEQ ID NO 44
<211> LENGTH: 485
<212> TYPE: PRT
<213> ORGANISM: Saccharomyces cerevisiae
```

```
<400> SEQUENCE: 44

Met Val His Leu Gly Pro Lys Lys Pro Gln Ala Arg Lys Gly Ser Met
1               5                   10                  15

Ala Asp Val Pro Lys Glu Leu Met Asp Glu Ile His Gln Leu Glu Asp
            20                  25                  30

Met Phe Thr Val Asp Ser Glu Thr Leu Arg Lys Val Val Lys His Phe
            35                  40                  45

Ile Asp Glu Leu Asn Lys Gly Leu Thr Lys Lys Gly Gly Asn Ile Pro
50                  55                  60

Met Ile Pro Gly Trp Val Met Glu Phe Pro Thr Gly Lys Glu Ser Gly
65                  70                  75                  80

Asn Tyr Leu Ala Ile Asp Leu Gly Gly Thr Asn Leu Arg Val Val Leu
                85                  90                  95

Val Lys Leu Ser Gly Asn His Thr Phe Asp Thr Thr Gln Ser Lys Tyr
            100                 105                 110

Lys Leu Pro His Asp Met Arg Thr Thr Lys His Gln Glu Glu Leu Trp
            115                 120                 125

Ser Phe Ile Ala Asp Ser Leu Lys Asp Phe Met Val Glu Gln Glu Leu
130                 135                 140

Leu Asn Thr Lys Asp Thr Leu Pro Leu Gly Phe Thr Phe Ser Tyr Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Val Glu Gly His Asp Val Val Pro Leu Leu
            180                 185                 190

Gln Asn Glu Ile Ser Lys Arg Glu Leu Pro Ile Glu Ile Val Ala Leu
            195                 200                 205

Ile Asn Asp Thr Val Gly Thr Leu Ile Ala Ser Tyr Tyr Thr Asp Pro
210                 215                 220

Glu Thr Lys Met Gly Val Ile Phe Gly Thr Gly Val Asn Gly Ala Phe
225                 230                 235                 240

Tyr Asp Val Val Ser Asp Ile Glu Lys Leu Glu Gly Lys Leu Ala Asp
                245                 250                 255

Asp Ile Pro Ser Asn Ser Pro Met Ala Ile Asn Cys Glu Tyr Gly Ser
            260                 265                 270

Phe Asp Asn Glu His Leu Val Leu Pro Arg Thr Lys Tyr Asp Val Ala
            275                 280                 285

Val Asp Glu Gln Ser Pro Arg Pro Gly Gln Gln Ala Phe Glu Lys Met
            290                 295                 300

Thr Ser Gly Tyr Tyr Leu Gly Glu Leu Leu Arg Leu Val Leu Leu Glu
305                 310                 315                 320

Leu Asn Glu Lys Gly Leu Met Leu Lys Asp Gln Asp Leu Ser Lys Leu
                325                 330                 335

Lys Gln Pro Tyr Ile Met Asp Thr Ser Tyr Pro Ala Arg Ile Glu Asp
            340                 345                 350

Asp Pro Phe Glu Asn Leu Glu Asp Thr Asp Ile Phe Gln Lys Asp
            355                 360                 365

Phe Gly Val Lys Thr Thr Leu Pro Glu Arg Lys Leu Ile Arg Arg Leu
            370                 375                 380

Cys Glu Leu Ile Gly Thr Arg Ala Ala Arg Leu Ala Val Cys Gly Ile
385                 390                 395                 400

Ala Ala Ile Cys Gln Lys Arg Gly Tyr Lys Thr Gly His Ile Ala Ala
                405                 410                 415
```

```
Asp Gly Ser Val Tyr Asn Lys Tyr Pro Gly Phe Lys Glu Ala Ala Ala
            420                 425                 430

Lys Gly Leu Arg Asp Ile Tyr Gly Trp Thr Gly Asp Ala Ser Lys Asp
        435                 440                 445

Pro Ile Thr Ile Val Pro Ala Glu Asp Gly Ser Gly Ala Gly Ala Ala
    450                 455                 460

Val Ile Ala Ala Leu Ser Glu Lys Arg Ile Ala Glu Gly Lys Ser Leu
465                 470                 475                 480

Gly Ile Ile Gly Ala
                485

<210> SEQ ID NO 45
<211> LENGTH: 1461
<212> TYPE: DNA
<213> ORGANISM: Saccharomyces cerevisiae

<400> SEQUENCE: 45
```

| | | |
|---|---|---|
| atggttcatt taggtccaaa aaaccacaa gccagaaagg gttccatggc cgatgtgcca | 60 |
| aaggaattga tgcaacaaat tgagaatttt gaaaaatttt tcactgttcc aactgaaact | 120 |
| ttacaagccg ttaccaagca cttcatttcc gaattggaaa agggtttgtc caagaagggt | 180 |
| ggtaacattc aatgattcc aggttgggtt atggatttcc caactggtaa ggaatccggt | 240 |
| gatttcttgg ccattgattt gggtggtacc aacttgagag ttgtcttagt caagttgggc | 300 |
| ggtgaccgta cctttgacac cactcaatct aagtacagat accagatgc tatgagaact | 360 |
| actcaaaatc cagacgaatt gtgggaattt attgccgact ctttgaaagc ttttattgat | 420 |
| gagcaattcc cacaaggtat ctctgagcca attccattgg gtttcaccctt ttctttccca | 480 |
| gcttctcaaa acaaaatcaa tgaaggtatc ttgcaaagat ggactaaagg ttttgatatt | 540 |
| ccaaacattg aaaaccacga tgttgttcca atgttgcaaa agcaaatcac taagaggaat | 600 |
| atcccaattg aagttgttgc tttgataaac gacactaccg gtactttggt tgcttcttac | 660 |
| tacactgacc cagaaactaa gatgggtgtt atcttcggta ctggtgtcaa tggtgcttac | 720 |
| tacgatgttt gttccgatat cgaaaagcta caaggaaaac tatctgatga cattccacca | 780 |
| tctgctccaa tggccatcaa ctgtgaatac ggttccttcg ataatgaaca tgtcgttttg | 840 |
| ccaagaacta aatacgatat caccattgat gaagaatctc caagaccagg ccaacaaacc | 900 |
| tttgaaaaaa tgtcttctgg ttactactta ggtgaaattt tgcgtttggc cttgatggac | 960 |
| atgtacaaac aaggtttcat cttcaagaac caagacttgt ctaagttcga caagcctttc | 1020 |
| gtcatggaca cttcttaccc agccagaatc gaggaagatc cattcgagaa cctagaagat | 1080 |
| accgatgact tgttccaaaa tgagttcggt atcaacacta ctgttcaaga cgtaaattg | 1140 |
| atcagacgtt tatctgaatt gattggtgct agagctgcta gattgtccgt ttgtggtatt | 1200 |
| gctgctatct gtcaaaagag aggttacaag accggtcaca tcgctgcaga cggttccgtt | 1260 |
| tacaacagat acccaggttt caagaaaag gctgccaatg ctttgaagga catttacggc | 1320 |
| tggactcaaa cctcactaga cgactaccca atcaagattg ttcctgctga agatggttcc | 1380 |
| ggtgctggtg ccgctgttat tgctgctttg gcccaaaaaa gaattgctga aggtaagtcc | 1440 |
| gttggtatca tcggtgctta a | 1461 |

```
<210> SEQ ID NO 46
<211> LENGTH: 486
<212> TYPE: PRT
<213> ORGANISM: Saccharomyces cerevisiae

<400> SEQUENCE: 46
```

-continued

```
Met Val His Leu Gly Pro Lys Lys Pro Gln Ala Arg Lys Gly Ser Met
1               5                   10                  15

Ala Asp Val Pro Lys Glu Leu Met Gln Gln Ile Glu Asn Phe Glu Lys
            20                  25                  30

Ile Phe Thr Val Pro Thr Glu Thr Leu Gln Ala Val Thr Lys His Phe
            35                  40                  45

Ile Ser Glu Leu Glu Lys Gly Leu Ser Lys Lys Gly Gly Asn Ile Pro
        50                  55                  60

Met Ile Pro Gly Trp Val Met Asp Phe Pro Thr Gly Lys Glu Ser Gly
65                  70                  75                  80

Asp Phe Leu Ala Ile Asp Leu Gly Gly Thr Asn Leu Arg Val Val Leu
                85                  90                  95

Val Lys Leu Gly Gly Asp Arg Thr Phe Asp Thr Thr Gln Ser Lys Tyr
                100                 105                 110

Arg Leu Pro Asp Ala Met Arg Thr Thr Gln Asn Pro Asp Glu Leu Trp
            115                 120                 125

Glu Phe Ile Ala Asp Ser Leu Lys Ala Phe Ile Asp Glu Gln Phe Pro
        130                 135                 140

Gln Gly Ile Ser Glu Pro Ile Pro Leu Gly Phe Thr Phe Ser Phe Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Ile Glu Asn His Asp Val Val Pro Met Leu
            180                 185                 190

Gln Lys Gln Ile Thr Lys Arg Asn Ile Pro Ile Glu Val Val Ala Leu
        195                 200                 205

Ile Asn Asp Thr Thr Gly Thr Leu Val Ala Ser Tyr Tyr Thr Asp Pro
        210                 215                 220

Glu Thr Lys Met Gly Val Ile Phe Gly Thr Gly Val Asn Gly Ala Tyr
225                 230                 235                 240

Tyr Asp Val Cys Ser Asp Ile Glu Lys Leu Gln Gly Lys Leu Ser Asp
                245                 250                 255

Asp Ile Pro Pro Ser Ala Pro Met Ala Ile Asn Cys Glu Tyr Gly Ser
            260                 265                 270

Phe Asp Asn Glu His Val Val Leu Pro Arg Thr Lys Tyr Asp Ile Thr
        275                 280                 285

Ile Asp Glu Glu Ser Pro Arg Pro Gly Gln Gln Thr Phe Glu Lys Met
        290                 295                 300

Ser Ser Gly Tyr Tyr Leu Gly Glu Ile Leu Arg Leu Ala Leu Met Asp
305                 310                 315                 320

Met Tyr Lys Gln Gly Phe Ile Phe Lys Asn Gln Asp Leu Ser Lys Phe
            325                 330                 335

Asp Lys Pro Phe Val Met Asp Thr Ser Tyr Pro Ala Arg Ile Glu Glu
            340                 345                 350

Asp Pro Phe Glu Asn Leu Glu Asp Thr Asp Asp Leu Phe Gln Asn Glu
        355                 360                 365

Phe Gly Ile Asn Thr Thr Val Gln Glu Arg Lys Leu Ile Arg Arg Leu
        370                 375                 380

Ser Glu Leu Ile Gly Ala Arg Ala Ala Arg Leu Ser Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Arg Tyr Pro Gly Phe Lys Glu Lys Ala Ala
```

```
              420                 425                 430
Asn Ala Leu Lys Asp Ile Tyr Gly Trp Thr Gln Thr Ser Leu Asp Asp
            435                 440                 445

Tyr Pro Ile Lys Ile Val Pro Ala Glu Asp Gly Ser Gly Ala Gly Ala
        450                 455                 460

Ala Val Ile Ala Ala Leu Ala Gln Lys Arg Ile Ala Glu Gly Lys Ser
465                 470                 475                 480

Val Gly Ile Ile Gly Ala
            485

<210> SEQ ID NO 47
<211> LENGTH: 1164
<212> TYPE: DNA
<213> ORGANISM: Klebsiella pneumoniae

<400> SEQUENCE: 47
tcagaatgcc tggcggaaaa tcgcggcaat ctcctgctcg ttgcctttac gcgggttcga      60
gaacgcattg ccgtctttca gagccatctc cgccatgtag gggaagtcgg cctcttttac     120
tcccagatcg cgcagatgct gcggaatacc gatatccatc gacagacgcg tgatagcggc     180
gatggctttt ccgccgcgt cgagagtgga cagtccggtg atattttcgc ccatcagttc     240
agcgatatcg gcgaatttct ccgggttggc gatcaggttg tagcgggcca catgcggcag     300
caggacagcg ttggccacgc cgtgcggcat gtcgtacagg ccgcccagct ggtgcgccat     360
ggcgtgcacg tagccgaggt tggcgttatt gaaagccatc ccggccagca gagaggcata     420
ggccatgttt tcccgcgcct gcagattgct gccgagggcc acggcctggc gcaggttgcg     480
ggcgatgagg cggatcgcct gcatggcggc ggcgtccgtc accgggttag cgtctttgga     540
gatataggcc tctacggcgt gggtcagggc atccatcccg gtcgccgcgg tcagggcggc     600
cggtttaccg atcatcagca gcggatcgtt gatagagacc gacggcaggt tgcgccagct     660
gacgatcaca aacttcactt tggtttcggt gttggtcagg acgcagtggc gggtgacctc     720
gctggcggtg ccggcggtgg tattgaccgc gacgataggc ggcagcgggt tggtcagggt     780
ctcgattccg gcatactggt acagatcgcc ctcatgggtg gcggcgatgc cgatgccttt     840
gccgcaatcg tgcgggctgc cgccgcccac ggtgacgatg atgtcgcact gttcgcggcg     900
aaacacggcg aggccgtcgc gcacgttggt gtctttcggg ttcggctcga cgccgtcaaa     960
gatcgccacc tcgatcccgg cctcccgcag ataatgcagg ttttgtccca ctgcgccatc    1020
tttaattgcc cgcaggcctt tgtcggtgac cagcagggct ttttccccc ccagcagctg    1080
gcagcgttcg ccgactacgg aaatggcgtt ggggccaaaa aagttaacgt ttggcaccag    1140
ataatcaaac atacgatagc tcat                                           1164

<210> SEQ ID NO 48
<211> LENGTH: 387
<212> TYPE: PRT
<213> ORGANISM: Klebsiella pneumoniae

<400> SEQUENCE: 48

Met Ser Tyr Arg Met Phe Asp Tyr Leu Val Pro Asn Val Asn Phe Phe
1               5                   10                  15

Gly Pro Asn Ala Ile Ser Val Val Gly Glu Arg Cys Gln Leu Leu Gly
            20                  25                  30

Gly Lys Lys Ala Leu Leu Val Thr Asp Lys Gly Leu Arg Ala Ile Lys
        35                  40                  45

Asp Gly Ala Val Asp Lys Thr Leu His Tyr Leu Arg Glu Ala Gly Ile
```

```
            50                  55                  60
Glu Val Ala Ile Phe Asp Gly Val Pro Asn Pro Lys Asp Thr Asn
 65                  70                  75                  80

Val Arg Asp Gly Leu Ala Val Phe Arg Arg Glu Gln Cys Asp Ile Ile
                 85                  90                  95

Val Thr Val Gly Gly Ser Pro His Asp Cys Gly Lys Gly Ile Gly
            100                 105                 110

Ile Ala Ala Thr His Glu Gly Asp Leu Tyr Gln Tyr Ala Gly Ile Glu
            115                 120                 125

Thr Leu Thr Asn Pro Leu Pro Pro Ile Val Ala Val Asn Thr Thr Ala
130                 135                 140

Gly Thr Ala Ser Glu Val Thr Arg His Cys Val Leu Thr Asn Thr Glu
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Ile Gly Lys Pro Ala Ala Leu Thr
                180                 185                 190

Ala Ala Thr Gly Met Asp Ala Leu Thr His Ala Val Glu Ala Tyr Ile
                195                 200                 205

Ser Lys Asp Ala Asn Pro Val Thr Asp Ala Ala Met Gln Ala Ile
210                 215                 220

Arg Leu Ile Ala Arg Asn Leu Arg Gln Ala Val Ala Leu Gly Ser Asn
225                 230                 235                 240

Leu Gln Ala Arg Glu Asn Met Ala Tyr Ala Ser Leu Leu Ala Gly Met
                245                 250                 255

Ala Phe Asn Asn Ala Asn Leu Gly Tyr Val His Ala Met Ala His Gln
                260                 265                 270

Leu Gly Gly Leu Tyr Asp Met Pro His Gly Val Ala Asn Ala Val Leu
                275                 280                 285

Leu Pro His Val Ala Arg Tyr Asn Leu Ile Ala Asn Pro Glu Lys Phe
                290                 295                 300

Ala Asp Ile Ala Glu Leu Met Gly Glu Asn Ile Thr Gly Leu Ser Thr
305                 310                 315                 320

Leu Asp Ala Ala Glu Lys Ala Ile Ala Ala Ile Thr Arg Leu Ser Met
                325                 330                 335

Asp Ile Gly Ile Pro Gln His Leu Arg Asp Leu Gly Val Lys Glu Ala
                340                 345                 350

Asp Phe Pro Tyr Met Ala Glu Met Ala Leu Lys Asp Gly Asn Ala Phe
                355                 360                 365

Ser Asn Pro Arg Lys Gly Asn Glu Gln Glu Ile Ala Ala Ile Phe Arg
370                 375                 380

Gln Ala Phe
385

<210> SEQ ID NO 49
<211> LENGTH: 1824
<212> TYPE: DNA
<213> ORGANISM: Klebsiella pneumoniae
<220> FEATURE:
<221> NAME/KEY: CDS
<222> LOCATION: (1)..(1824)

<400> SEQUENCE: 49 atg ccg tta ata gcc ggg att gat atc ggc aac gcc acc acc gag gtg    48
Met Pro Leu Ile Ala Gly Ile Asp Ile Gly Asn Ala Thr Thr Glu Val
 1               5                  10                  15
```

```
gcg ctg gcg tcc gac tac ccg cag gcg agg gcg ttt gtt gcc agc ggg      96
Ala Leu Ala Ser Asp Tyr Pro Gln Ala Arg Ala Phe Val Ala Ser Gly
         20                  25                  30 atc gtc gcg acg acg ggc atg aaa ggg acg cgg gac aat atc gcc ggg     144
Ile Val Ala Thr Thr Gly Met Lys Gly Thr Arg Asp Asn Ile Ala Gly
             35                  40                  45 acc ctc gcc gcg ctg gag cag gcc ctg gcg aaa aca ccg tgg tcg atg     192
Thr Leu Ala Ala Leu Glu Gln Ala Leu Ala Lys Thr Pro Trp Ser Met
 50                  55                  60 agc gat gtc tct cgc atc tat ctt aac gaa gcc gcg ccg gtg att ggc     240
Ser Asp Val Ser Arg Ile Tyr Leu Asn Glu Ala Ala Pro Val Ile Gly
 65                  70                  75                  80 gat gtg gcg atg gag acc atc acc gag acc att atc acc gaa tcg acc     288
Asp Val Ala Met Glu Thr Ile Thr Glu Thr Ile Ile Thr Glu Ser Thr
                 85                  90                  95 atg atc ggt cat aac ccg cag acg ccg ggc ggg gtg ggc gtt ggc gtg     336
Met Ile Gly His Asn Pro Gln Thr Pro Gly Gly Val Gly Val Gly Val
             100                 105                 110 ggg acg act atc gcc ctc ggg cgg ctg gcg acg ctg ccg gcg gcg cag     384
Gly Thr Thr Ile Ala Leu Gly Arg Leu Ala Thr Leu Pro Ala Ala Gln
         115                 120                 125 tat gcc gag ggg tgg atc gta ctg att gac gac gcc gtc gat ttc ctt     432
Tyr Ala Glu Gly Trp Ile Val Leu Ile Asp Asp Ala Val Asp Phe Leu
130                 135                 140 gac gcc gtg tgg tgg ctc aat gag gcg ctc gac cgg ggg atc aac gtg     480
Asp Ala Val Trp Trp Leu Asn Glu Ala Leu Asp Arg Gly Ile Asn Val
145                 150                 155                 160 gtg gcg gcg atc ctc aaa aag gac gac ggc gtg ctg gtg aac aac cgc     528
Val Ala Ala Ile Leu Lys Lys Asp Asp Gly Val Leu Val Asn Asn Arg
                165                 170                 175 ctg cgt aaa acc ctg ccg gtg gtg gat gaa gtg acg ctg ctg gag cag     576
Leu Arg Lys Thr Leu Pro Val Val Asp Glu Val Thr Leu Leu Glu Gln
            180                 185                 190 gtc ccc gag ggg gta atg gcg gcg gtg gaa gtg gcc gcg ccg ggc cag     624
Val Pro Glu Gly Val Met Ala Ala Val Glu Val Ala Ala Pro Gly Gln
        195                 200                 205 gtg gtg cgg atc ctg tcg aat ccc tac ggg atc gcc acc ttc ttc ggg     672
Val Val Arg Ile Leu Ser Asn Pro Tyr Gly Ile Ala Thr Phe Phe Gly
210                 215                 220 cta agc ccg gaa gag acc cag gcc atc gtc ccc atc gcc cgc gcc ctg     720
Leu Ser Pro Glu Glu Thr Gln Ala Ile Val Pro Ile Ala Arg Ala Leu
225                 230                 235                 240 att ggc aac cgt tcc gcg gtg gtg ctc aag acc ccg cag ggg gat gtg     768
Ile Gly Asn Arg Ser Ala Val Val Leu Lys Thr Pro Gln Gly Asp Val
                245                 250                 255 cag tcg cgg gtg atc ccg gcg ggc aac ctc tac att agc ggc gaa aag     816
Gln Ser Arg Val Ile Pro Ala Gly Asn Leu Tyr Ile Ser Gly Glu Lys
            260                 265                 270 cgc cgc gga gag gcc gat gtc gcc gag ggc gcg gaa gcc atc atg cag     864
Arg Arg Gly Glu Ala Asp Val Ala Glu Gly Ala Glu Ala Ile Met Gln
        275                 280                 285 gcg atg agc gcc tgc gct ccg gta cgc gac atc cgc ggc gaa ccg ggc     912
Ala Met Ser Ala Cys Ala Pro Val Arg Asp Ile Arg Gly Glu Pro Gly
290                 295                 300 acc cac gcc ggc ggc atg ctt gag cgg gtg cgc aag gta atg gcg tcc     960
Thr His Ala Gly Gly Met Leu Glu Arg Val Arg Lys Val Met Ala Ser
305                 310                 315                 320 ctg acc ggc cat gag atg agc gcg ata tac atc cag gat ctg ctg gcg    1008
Leu Thr Gly His Glu Met Ser Ala Ile Tyr Ile Gln Asp Leu Leu Ala
                325                 330                 335
```

```
gtg gat acg ttt att ccg cgc aag gtg cag ggc ggg atg gcc ggc gag    1056
Val Asp Thr Phe Ile Pro Arg Lys Val Gln Gly Gly Met Ala Gly Glu
        340                 345                 350 tgc gcc atg gag aat gcc gtc ggg atg gcg gcg atg gtg aaa gcg gat    1104
Cys Ala Met Glu Asn Ala Val Gly Met Ala Ala Met Val Lys Ala Asp
            355                 360                 365 cgt ctg caa atg cag gtt atc gcc cgc gaa ctg agc gcc cga ctg cag    1152
Arg Leu Gln Met Gln Val Ile Ala Arg Glu Leu Ser Ala Arg Leu Gln
        370                 375                 380 acc gag gtg gtg gtg ggc ggc gtg gag gcc aac atg gcc atc gcc ggg    1200
Thr Glu Val Val Val Gly Gly Val Glu Ala Asn Met Ala Ile Ala Gly
385                 390                 395                 400 gcg tta acc act ccc ggc tgt gcg gcg ccg ctg gcg atc ctc gac ctc    1248
Ala Leu Thr Thr Pro Gly Cys Ala Ala Pro Leu Ala Ile Leu Asp Leu
            405                 410                 415 ggc gcc ggc tcg acg gat gcg gcg atc gtc aac gcg gag ggg cag ata    1296
Gly Ala Gly Ser Thr Asp Ala Ala Ile Val Asn Ala Glu Gly Gln Ile
        420                 425                 430 acg gcg gtc cat ctc gcc ggg gcg ggg aat atg gtc agc ctg ttg att    1344
Thr Ala Val His Leu Ala Gly Ala Gly Asn Met Val Ser Leu Leu Ile
    435                 440                 445 aaa acc gag ctg ggc ctc gag gat ctt tcg ctg gcg gaa gcg ata aaa    1392
Lys Thr Glu Leu Gly Leu Glu Asp Leu Ser Leu Ala Glu Ala Ile Lys
450                 455                 460 aaa tac ccg ctg gcc aaa gtg gaa agc ctg ttc agt att cgt cac gag    1440
Lys Tyr Pro Leu Ala Lys Val Glu Ser Leu Phe Ser Ile Arg His Glu
465                 470                 475                 480 aat ggc gcg gtg gag ttc ttt cgg gaa gcc ctc agc ccg gcg gtg ttc    1488
Asn Gly Ala Val Glu Phe Phe Arg Glu Ala Leu Ser Pro Ala Val Phe
            485                 490                 495 gcc aaa gtg gtg tac atc aag gag ggc gaa ctg gtg ccg atc gat aac    1536
Ala Lys Val Val Tyr Ile Lys Glu Gly Glu Leu Val Pro Ile Asp Asn
        500                 505                 510 gcc agc ccg ctg gaa aaa att cgt ctc gtg cgc cgg cag gcg aaa gag    1584
Ala Ser Pro Leu Glu Lys Ile Arg Leu Val Arg Arg Gln Ala Lys Glu
    515                 520                 525 aaa gtg ttt gtc acc aac tgc ctg cgc gcg ctg cgc cag gtc tca ccc    1632
Lys Val Phe Val Thr Asn Cys Leu Arg Ala Leu Arg Gln Val Ser Pro
530                 535                 540 ggc ggt tcc att cgc gat atc gcc ttt gtg gtg ctg gtg ggc ggc tca    1680
Gly Gly Ser Ile Arg Asp Ile Ala Phe Val Val Leu Val Gly Gly Ser
545                 550                 555                 560 tcg ctg gac ttt gag atc ccg cag ctt atc acg gaa gcc ttg tcg cac    1728
Ser Leu Asp Phe Glu Ile Pro Gln Leu Ile Thr Glu Ala Leu Ser His
            565                 570                 575 tat ggc gtg gtc gcc ggg cag ggc aat att cgg gga aca gaa ggg ccg    1776
Tyr Gly Val Val Ala Gly Gln Gly Asn Ile Arg Gly Thr Glu Gly Pro
        580                 585                 590 cgc aat gcg gtc gcc acc ggg ctg cta ctg gcc ggt cag gcg aat taa    1824
Arg Asn Ala Val Ala Thr Gly Leu Leu Leu Ala Gly Gln Ala Asn
    595                 600                 605

<210> SEQ ID NO 50
<211> LENGTH: 607
<212> TYPE: PRT
<213> ORGANISM: Klebsiella pneumoniae

<400> SEQUENCE: 50

Met Pro Leu Ile Ala Gly Ile Asp Ile Gly Asn Ala Thr Thr Glu Val
1               5                   10                  15

Ala Leu Ala Ser Asp Tyr Pro Gln Ala Arg Ala Phe Val Ala Ser Gly
```

```
                    20                  25                  30
Ile Val Ala Thr Thr Gly Met Lys Gly Thr Arg Asp Asn Ile Ala Gly
                35                  40                  45
Thr Leu Ala Ala Leu Glu Gln Ala Leu Ala Lys Thr Pro Trp Ser Met
                50                  55                  60
Ser Asp Val Ser Arg Ile Tyr Leu Asn Glu Ala Ala Pro Val Ile Gly
65                  70                  75                  80
Asp Val Ala Met Glu Thr Ile Thr Glu Thr Ile Thr Glu Ser Thr
                    85                  90                  95
Met Ile Gly His Asn Pro Gln Thr Pro Gly Gly Val Gly Val Gly Val
                    100                 105                 110
Gly Thr Thr Ile Ala Leu Gly Arg Leu Ala Thr Leu Pro Ala Ala Gln
                    115                 120                 125
Tyr Ala Glu Gly Trp Ile Val Leu Ile Asp Asp Ala Val Asp Phe Leu
                    130                 135                 140
Asp Ala Val Trp Trp Leu Asn Glu Ala Leu Asp Arg Gly Ile Asn Val
145                 150                 155                 160
Val Ala Ala Ile Leu Lys Lys Asp Asp Gly Val Leu Val Asn Asn Arg
                    165                 170                 175
Leu Arg Lys Thr Leu Pro Val Val Asp Glu Val Thr Leu Leu Glu Gln
                    180                 185                 190
Val Pro Glu Gly Val Met Ala Ala Val Glu Val Ala Ala Pro Gly Gln
                    195                 200                 205
Val Val Arg Ile Leu Ser Asn Pro Tyr Gly Ile Ala Thr Phe Phe Gly
                    210                 215                 220
Leu Ser Pro Glu Glu Thr Gln Ala Ile Val Pro Ile Ala Arg Ala Leu
225                 230                 235                 240
Ile Gly Asn Arg Ser Ala Val Val Leu Lys Thr Pro Gln Gly Asp Val
                    245                 250                 255
Gln Ser Arg Val Ile Pro Ala Gly Asn Leu Tyr Ile Ser Gly Glu Lys
                    260                 265                 270
Arg Arg Gly Glu Ala Asp Val Ala Glu Gly Ala Glu Ala Ile Met Gln
                    275                 280                 285
Ala Met Ser Ala Cys Ala Pro Val Arg Asp Ile Arg Gly Glu Pro Gly
                    290                 295                 300
Thr His Ala Gly Gly Met Leu Glu Arg Val Arg Lys Val Met Ala Ser
305                 310                 315                 320
Leu Thr Gly His Glu Met Ser Ala Ile Tyr Ile Gln Asp Leu Leu Ala
                    325                 330                 335
Val Asp Thr Phe Ile Pro Arg Lys Val Gln Gly Gly Met Ala Gly Glu
                    340                 345                 350
Cys Ala Met Glu Asn Ala Val Gly Met Ala Ala Met Val Lys Ala Asp
                    355                 360                 365
Arg Leu Gln Met Gln Val Ile Ala Arg Glu Leu Ser Ala Arg Leu Gln
                    370                 375                 380
Thr Glu Val Val Val Gly Gly Val Glu Ala Asn Met Ala Ile Ala Gly
385                 390                 395                 400
Ala Leu Thr Thr Pro Gly Cys Ala Ala Pro Leu Ala Ile Leu Asp Leu
                    405                 410                 415
Gly Ala Gly Ser Thr Asp Ala Ala Ile Val Asn Ala Glu Gly Gln Ile
                    420                 425                 430
Thr Ala Val His Leu Ala Gly Ala Gly Asn Met Val Ser Leu Leu Ile
                    435                 440                 445
```

-continued

```
Lys Thr Glu Leu Gly Leu Glu Asp Leu Ser Leu Ala Glu Ala Ile Lys
        450                 455                 460
Lys Tyr Pro Leu Ala Lys Val Glu Ser Leu Phe Ser Ile Arg His Glu
465                 470                 475                 480
Asn Gly Ala Val Glu Phe Phe Arg Glu Ala Leu Ser Pro Ala Val Phe
                485                 490                 495
Ala Lys Val Val Tyr Ile Lys Glu Gly Glu Leu Val Pro Ile Asp Asn
            500                 505                 510
Ala Ser Pro Leu Glu Lys Ile Arg Leu Val Arg Arg Gln Ala Lys Glu
        515                 520                 525
Lys Val Phe Val Thr Asn Cys Leu Arg Ala Leu Arg Gln Val Ser Pro
    530                 535                 540
Gly Gly Ser Ile Arg Asp Ile Ala Phe Val Val Leu Val Gly Gly Ser
545                 550                 555                 560
Ser Leu Asp Phe Glu Ile Pro Gln Leu Ile Thr Glu Ala Leu Ser His
                565                 570                 575
Tyr Gly Val Val Ala Gly Gln Gly Asn Ile Arg Gly Thr Glu Gly Pro
            580                 585                 590
Arg Asn Ala Val Ala Thr Gly Leu Leu Leu Ala Gly Gln Ala Asn
        595                 600                 605

<210> SEQ ID NO 51
<211> LENGTH: 13669
<212> TYPE: DNA
<213> ORGANISM: Artificial Sequence
<220> FEATURE:
<223> OTHER INFORMATION: Plasmid

<400> SEQUENCE: 51
tagtaaagcc ctcgctagat tttaatgcgg atgttgcgat tacttcgcca actattgcga      60
taacaagaaa aagccagcct ttcatgatat atctcccaat ttgtgtaggg cttattatgc     120
acgcttaaaa ataataaaag cagacttgac ctgatagttt ggctgtgagc aattatgtgc     180
ttagtgcatc taacgcttga gttaagccgc gccgcgaagc ggcgtcggct tgaacgaatt     240
gttagacatt atttgccgac taccttggtg atctcgcctt tcacgtagtg acaaattct      300 tccaactgat ctgcgcgcga ggccaagcga tcttcttctt gtccaagata agcctgtcta     360
gcttcaagta tgacgggctg atactgggcc ggcaggcgct ccattgccca gtcggcagcg     420
acatccttcg gcgcgatttt gccggttact gcgctgtacc aaatgcggga caacgtaagc     480 actcatttc gctcatcgcc agccagtcg ggcggcgagt tccatagcgt taaggtttca     540
tttagcgcct caaatagatc ctgttcagga accggatcaa agagttcctc cgccgctgga     600
cctaccaagg caacgctatg ttctcttgct tttgtcagca agatagccag atcaatgtcg     660
atcgtggctg gctcgaagat acctgcaaga atgtcattgc gctgccattc tccaaattgc     720
agttcgcgct tagctggata acgccacgga atgatgtcgt cgtgcacaac aatggtgact     780
tctacagcgc ggagaatctc gctctctcca ggggaagccg aagtttccaa aaggtcgttg     840
atcaaagctc gccgcgttgt ttcatcaagc cttacggtca ccgtaaccag caaatcaata     900
tcactgtgtg gcttcaggcc gccatccact gcggagccgt acaaatgtac ggccagcaac     960
gtcggttcga gatggcgctc gatgacgcca actacctctg atagttgagt cgatacttcg    1020
gcgatcaccg cttccctcat gatgtttaac tttgttttag ggcgactgcc ctgctgcgta    1080
acatcgttgc tgctccataa catcaaacat cgacccacgg cgtaacgcgc ttgctgcttg    1140
gatgcccgag gcatagactg taccccaaaa aaacagtcat aacaagccat gaaaaccgcc    1200
```

```
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgttttcc acggtgtgcg tcacccggca accttgggca gcagcgaagt cgaggcattt  1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctggaagg cgagcatcgt tgttcgccc agcttctgta tggaacgggc    1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgattttt ccccacggga ggcgtcactg    1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatcttttt tacaccgttt tcatctgtgc atatggacag ttttcccttt gatatgtaac   2220
ggtgaacagt tgttctactt tgtttgtta gtcttgatgc ttcactgata gatcaagag    2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520
atttttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta atctttact tattggtttc aaaacccatt ggttaagcct tttaaactca    2700
tggtagttat tttcaagcat taacatgaac ttaaattcat caaggctaat ctctatattt   2760
gccttgtgag ttttcttttg tgttagttct tttaataacc actcataaat cctcatagag   2820
tatttgtttt caaaagactt aacatgttcc agattatatt ttatgaattt ttttaactgg   2880
aaaagataag gcaatatctc ttcactaaaa actaattcta attttcgct tgagaacttg     2940
gcatagtttg tccactggaa aatctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg gctagtcaa    3300
tgataattac tagtccttttt cctttgagtt gtgggtatct gtaaattctg ctagaccttt  3360
gctgaaaac ttgtaaattc tgctagaccc tctgtaaatt ccgctagacc tttgtgtgtt    3420
tttttgttt atattcaagt ggttataatt tatagaataa agaaagaata aaaaagata     3480
aaagaatag atcccagccc tgtgtataac tcactacttt agtcagttcc gcagtattac    3540
aaaaggatgt cgcaaacgct gtttgctcct ctacaaaaca gaccttaaaa ccctaaaggc   3600
```

```
ttaagtagca ccctcgcaag ctcgggcaaa tcgctgaata ttccttttgt ctccgaccat    3660
caggcacctg agtcgctgtc tttttcgtga cattcagttc gctgcgctca cggctctggc    3720
agtgaatggg ggtaaatggc actacaggcg ccttttatgg attcatgcaa ggaaactacc    3780
cataatacaa gaaaagcccg tcacgggctt ctcagggcgt tttatggcgg gtctgctatg    3840
tggtgctatc tgacttttg ctgttcagca gttcctgccc tctgattttc cagtctgacc    3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcggacgggg gcactggaac gagaagtcag    4140
gcgagccgtc acgcccttga caatgccaca tcctgagcaa ataattcaac cactaaacaa    4200
atcaaccgcg tttcccggag gtaaccaagc ttgcgggaga gaatgatgaa caagagccaa    4260
caagttcaga caatcaccct ggccgccgcc cagcaaatgg cggcggcggt ggaaaaaaaa    4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta tttttaatga gcaggtaatt ggcgccgtcg gcgttagcgg cggtacggtc    4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga gcaggggtc ccctgccaga    4860 ccataaccta tgacggaggc ggtgacgccg ctgcgctggg cgccctggcg gccagaagct    4920
cgcccctgcg ggtgggtatc gggctcagcg cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcacgtggcg cgcacccagt cccgtcggct cgaacgcctg ctgacggcca    5520
tggaccgcgc gcatccgctg cgcgacgcgc tcaaacgcta cagcaatcgc ctgtcggatg    5580
ccctgttctc catggcgcga atcgaagaga ctaggcctga tgcttgcgct tgaactggcc    5640
tagcaaacac agaaaaaagc ccgcacctga cagtgcgggc tttttttttc ctaggcgatc    5700
tgtgctgttt gccacggtat gcagcaccag cgcgagatta tgggctcgca cgctcgactg    5760
tcggacgggg gcactggaac gagaagtcag gcgagccgtc acgcccttga caatgccaca    5820
tcctgagcaa ataattcaac cactaaacaa atcaaccgcg tttcccggag gtaaccaagc    5880
ttcacctttt gagccgatga acaatgaaaa gatcaaaacg atttgcagta ctggcccagc    5940
gccccgtcaa tcaggacggg ctgattggcg agtggcctga agagggctg atcgccatgg    6000
```

```
acagcccctt tgacccggtc tcttcagtaa aagtggacaa cggtctgatc gtcgaactgg    6060
acggcaaacg ccgggaccag tttgacatga tcgaccgatt tatcgccgat tacgcgatca    6120
acgttgagcg cacagagcag gcaatgcgcc tggaggcggt ggaaatagcc cgtatgctgg    6180
tggatattca cgtcagccgg gaggagatca ttgccatcac taccgccatc acgccggcca    6240
aagcggtcga ggtgatggcg cagatgaacg tggtggagat gatgatggcg ctgcagaaga    6300
tgcgtgcccg ccgaccccc tccaaccagt gccacgtcac caatctcaaa gataatccgg    6360
tgcagattgc cgctgacgcc gccgaggccg ggatccgcgg cttctcagaa caggagacca    6420
cggtcggtat cgcgcgctac gcgccgttta cgccctggc gctgttggtc ggttcgcagt    6480
gcggccgccc cggcgtgttg acgcagtgct cggtggaaga ggccaccgag ctggagctgg    6540
gcatgcgtgg cttaaccagc tacgccgaga cggtgtcggt ctacggcacc gaagcggtat    6600
ttaccgacgg cgatgatacg ccgtggtcaa aggcgttcct cgcctcggcc tacgcctccc    6660
gcgggttgaa aatgcgctac acctccggca ccggatccga agcgctgatg ggctattcgg    6720
agagcaagtc gatgctctac ctcgaatcgc gctgcatctt cattactaaa ggcgccgggg    6780
ttcagggact gcaaaacggc gcggtgagct gtatcggcat gaccggcgct gtgccgtcgg    6840
gcattcgggc ggtgctggcg gaaaacctga tcgcctctat gctcgacctc gaagtggcgt    6900
ccgccaacga ccagactttc tcccactcgg atattgccg caccgcgcgc accctgatgc    6960
agatgctgcc gggcaccgac tttattttct ccggctacag cgcggtgccg aactacgaca    7020
acatgttcgc cggctcgaac ttcgatgcgg aagattttga tgattacaac atcctgcagc    7080
gtgacctgat ggttgacggc ggcctgcgtc cggtgaccga ggcggaaacc attgccattc    7140
gccagaaagc ggcgcgggcg atccaggcgg ttttccgcga gctggggctg ccgccaatcg    7200
ccgacgagga ggtggaggcc gccacctacg cgcacgcag caacgagatg ccgccgcgta    7260
acgtggtgga ggatctgagt gcggtggaag agatgatgaa cgcaacatc accggcctcg    7320 atattgtcgg cgcgctgagc cgcagcggct ttgaggatat cgccagcaat attctcaata    7380
tgctgcgcca gcgggtcacc ggcgattacc tgcagacctc ggccattctc gatcggcagt    7440
tcgaggtggt gagtgcggtc aacgacatca atgactatca ggggccgggc accggctatc    7500
gcatctctgc cgaacgctgg gcggagatca aaaatattcc gggcgtggtt cagcccgaca    7560
ccattgaata aggcggtatt cctgtgcaac agacaaccca aattcagccc tcttttaccc    7620
tgaaaacccg cgagggcggg gtagcttctg ccgatgaacg cgccgatgaa gtggtgatcg    7680
gcgtcggccc tgccttcgat aaacaccagc atcacactct gatcgatatg ccccatggcg    7740
cgatcctcaa agagctgatt ccggggtgg aagaagaggg gcttcacgcc cgggtggtgc    7800
gcattctgcg cacgtccgac gtctcctta tggcctggga tgcggccaac ctgagcggct    7860
cggggatcgg catcggtatc cagtcgaagg ggaccacggt catccatcag cgcgatctgc    7920
tgccgctcag caacctggag ctgttctccc aggcgccgct gctgacgctg agacctaccc    7980
ggcagattgg caaaaacgct gcgcgctatg cgcgcaaaga gtcaccttcg ccggtgccgg    8040
tggtgaacga tcagatggtg cggccgaaat ttatggccaa agccgcgcta tttcatatca    8100
aagagaccaa acatgtggtg caggacgccg agcccgtcac cctgcacatc gacttagtaa    8160
gggagtgacc atgagcgaga aaaccatgcg cgtgcaggat tatccgttag ccacccgctg    8220
cccggagcat atcctgacgc ctaccggcaa accattgacc gatattaccc tcgagaaggt    8280
gctctctggc gaggtgggcc cgcaggatgt gcggatctcc cgccagaccc ttgagtacca    8340
ggcgcagatt gccgagcaga tgcagcgcca tgcggtggcg cgcaatttcc gccgcgcggc    8400
```

```
ggagcttatc gccattcctg acgagcgcat tctggctatc tataacgcgc tgcgcccgtt   8460
ccgctcctcg caggcggagc tgctggcgat cgccgacgag ctggagcaca cctggcatgc   8520
gacagtgaat gccgcctttg tccgggagtc ggcggaagtg tatcagcagc ggcataagct   8580
gcgtaaagga agctaagcgg aggtcagcat gccgttaata gccgggattg atatcggcaa   8640
cgccaccacc gaggtggcgc tggcgtccga ctacccgcag gcgagggcgt tgttgccag    8700
cgggatcgtc gcgacgacgg gcatgaaagg gacgcgggac aatatcgccg ggaccctcgc   8760
cgcgctggag caggccctgg cgaaaacacc gtggtcgatg agcgatgtct ctcgcatcta   8820
tcttaacgaa gccgcgccgg tgattggcga tgtggcgatg gagaccatca ccgagaccat   8880
tatcaccgaa tcgaccatga tcggtcataa cccgcagacg ccgggcgggg tgggcgttgg   8940
cgtggggacg actatcgccc tcgggcggct ggcgacgctg ccggcggcgc agtatgccga   9000
ggggtggatc gtactgattg acgacgccgt cgatttcctt gacgccgtgt ggtggctcaa   9060
tgaggcgctc gaccggggga tcaacgtggt ggcggcgatc ctcaaaaagg acgacggcgt   9120
gctggtgaac aaccgcctgc gtaaaaccct gccggtggtg gatgaagtga cgctgctgga   9180
gcaggtcccc gaggggggtaa tggcggcggt ggaagtggcc gcgccgggcc aggtggtgcg   9240
gatcctgtcg aatccctacg ggatcgccac cttcttcggg ctaagcccgg aagagaccca   9300
ggccatcgtc cccatcgccc gcgccctgat tggcaaccgt tccgcggtgg tgctcaagac   9360
cccgcagggg gatgtgcagt cgcgggtgat cccggcgggc aacctctaca ttagcggcga   9420
aaagcgccgc ggagaggccg atgtcgccga gggcgcggaa gccatcatgc aggcgatgag   9480
cgcctgcgct ccggtacgcg acatccgcgg cgaaccgggc acccacgccg gcggcatgct   9540
tgagcgggtg cgcaaggtaa tggcgtccct gaccggccat gagatgagcg cgatatacat   9600
ccaggatctg ctggcggtgg atacgtttat tccgcgcaag gtgcagggcg ggatggccgg   9660
cgagtgcgcc atggagaatg ccgtcggat ggcggcgatg gtgaaagcgg atcgtctgca   9720
aatgcaggtt atcgcccgcg aactgagcgc ccgactgcag accgaggtgg tggtgggcgg   9780
cgtggaggcc aacatggcca tcgccggggc gttaaccact cccggctgtg cggcgccgct   9840
ggcgatcctc gacctcggcg ccggctcgac ggatgcggcg atcgtcaacg cggaggggca   9900
gataacggcg gtccatctcg ccggggcggg gaatatggtc agcctgttga ttaaaaccga   9960
gctgggcctc gaggatcttt cgctggcgga agcgataaaa aaatacccgc tggccaaagt  10020
ggaaagcctg ttcagtattc gtcacgagaa tggcgcggtg gagttctttc gggaagccct  10080
cagcccggcg gtgttcgcca aagtggtgta catcaaggag ggcgaactgg tgccgatcga  10140
taacgccagc ccgctggaaa aaattcgtct cgtgcgccgg caggcgaaag agaaagtgtt  10200
tgtcaccaac tgcctgcgcg cgctgcgcca ggtctcaccc ggcggttcca ttcgcgatat  10260
cgcctttgtg gtgctggtgg gcggctcatc gctggacttt gagatcccgc agcttatcac  10320
ggaagccttg tcgcactatg gcgtggtcgc cgggcagggc aatattcggg gaacagaagg  10380
gccgcgcaat gcggtcgcca ccgggctgct actggccggt caggcgaatt aaacgggcgc  10440
tcgcgccagc ctctaggtac aaataaaaaa ggcacgtcag atgacgtgcc tttttcttg  10500
tctagagtac tggcgaaagg gggatgtgct gcaaggcgat taagttgggt aacgccaggg  10560
ttttcccagt cacgacgttg taaaacgacg gccagtgaat tcgagctcgg tacccggggc  10620
ggccgcgcta gcgcccgatc cagctggagt ttgtagaaac gcaaaaggc catccgtcag  10680
gatggccttc tgcttaattt gatgcctggc agtttatggc gggcgtcctg cccgccaccc  10740
tccgggccgt tgcttcgcaa cgttcaaatc cgctcccggc ggatttgtcc tactcaggag  10800
```

```
agcgttcacc gacaaacaac agataaaacg aaaggcccag tctttcgact gagcctttcg   10860
ttttatttga tgcctggcag ttccctactc tcgcatgggg agaccccaca ctaccatcgg   10920
cgctacggcg tttcacttct gagttcggca tggggtcagg tgggaccacc gcgctactgc   10980
cgccaggcaa attctgtttt atcagaccgc ttctgcgttc tgatttaatc tgtatcaggc   11040
tgaaaatctt ctctcatccg ccaaaacagc caagcttgca tgcctgcagc ccgggttacc   11100
atttcaacag atcgtcctta gcatataagt agtcgtcaaa aatgaattca acttcgtctg   11160
tttcggcatt gtagccgcca actctgatgg attcgtggtt tttgacaatg atgtcacagc   11220 cttttttcctt taggaagtcc aagtcgaaag tagtggcaat accaatgatc ttacaaccgg   11280
cggcttttcc ggcggcaata cctgctggag cgtcttcaaa tactactacc ttagatttgg   11340
aagggtcttg ctcattgatc ggatatccta agccattcct gcccttcaga tatggttctg   11400
gatgaggctt accctgtttg acatcattag cggtaatgaa gtactttggt ctcctgattc   11460
ccagatgctc gaaccatttt tgtgccatat cacgggtacc ggaagttgcc acagcccatt   11520
tctcttttgg tagagcgttc aaagcgttgc acagcttaac tgcacctggg acttcaatgg   11580
atttttcacc gtacttgacc ggaatttcag cttctaattt gttaacatac tcttcattgg   11640
caaagtctgg agcgaactta gcaatggcat caaacgttct ccaaccatgc gagacttgga   11700
taacgtgttc agcatcgaaa taaggtttgt ccttaccgaa atccctccag aatgcagcaa   11760
tggctggttg agagatgata atggtaccgt cgacgtcgaa caaagcggcg ttaactttca   11820
aagatagagg tttagtagtc aatcccataa ttctagtctg tttcctggat ccaataaatc   11880
taatcttcat gtagatctaa ttcttcaatc atgtccggca ggttcttcat tgggtagttg   11940
ttgtaaacga tttggtatac ggcttcaaat aatgggaagt cttcgacaga gcccacatgtt  12000 tccaaccatt cgtgaacttc tttgcaggta attaaacctt gagcggattg gccattcaac   12060
aactcctttt cacattccca ggcgtcctta ccagaagtag ccattagcct agcaaccttg   12120
acgtttctac caccagcgca ggtggtgatc aaatcagcaa caccagcaga ctcttggtag   12180
tatgtttctt ctctagattc tgggaaaaac atttgaccga atctgatgat ctcacccaaa   12240
ccgactcttt ggatggcagc agaagcgttg ttaccccagc ctagaccttc gacgaaacca   12300
caacctaagg caacaacgtt cttcaaagca ccacagatgg agataccagc aacatcttcg   12360
atgacactaa cgtggaagta aggtctgtgg aacaaggcct ttagaacctt atggtcgacg   12420
tccttgccct cgcctctgaa atcctttgga atgtggtaag caactgttgt ttcagaccag   12480
tgttcttgag cgacttcggt ggcaatgtta gcaccagata gagcaccaca ttgaatacct   12540
agttcctcag tgatgtaaga ggatagcaat tggacacctt tagcaccaac ttcaaaaccc   12600
tttagacagg agatagctct gacgtgtgaa tcaacatgac ctttcaattg gctacagata   12660
cggggcaaaa attgatgtgg aatgttgaaa acgatgatgt cgacatcctt gactgaatca   12720
atcaagtctg gattagcaac caaattgtcg ggtagagtga tgccaggcaa gtatttcacg   12780
ttttgatgtc tagtatttat gatttcagtc aattttttcac cattgatctc ttcttcgaac   12840
acccacattt gtactattgg agcgaaaact tctgggtatc ccttacaatt ttcggcaacc   12900
accttggcaa tagtagtacc ccagttacca gatccaatca cagtaacctt gaaaggcttt   12960
tcggcagcct tcaaagaaac agaagaggaa cttctctttc taccagcatt caagtggccg   13020
gaagttaagt ttaatctatc agcagcagca gccatggaat tgtcctcctt actagtcatg   13080
gtctgtttcc tgtgtgaaat tgttatccgc tcacaattcc acacattata cgagccggat   13140
gattaattgt caacagctca tttcagaata tttgccagaa ccgttatgat gtcggcgcaa   13200
```

-continued

```
aaaacattat ccagaacggg agtgcgcctt gagcgacacg aattatgcag tgatttacga      13260
cctgcacagc cataccacag cttccgatgg ctgcctgacg ccagaagcat tggtgcacgc      13320
tagccagtac atttaaatgg taccctctag tcaaggcctt aagtgagtcg tattacggac      13380
tggccgtcgt tttacaacgt cgtgactggg aaaaccctgg cgttacccaa cttaatcgcc      13440
ttgcagcaca tccccctttc gccagctggc gtaatagcga agaggcccgc accgatcgcc      13500
cttcccaaca gttgcgcagc ctgaatgcgc aatggcgcct gatgcggtat tttctcctta      13560
cgcatctgtg cggtatttca caccgcatat ggtgcactct cagtacaatc tgctctgatg      13620
ccgcatagtt aagccagccc cgacacccgc caacacccgc tgacgagct                  13669
```

<210> SEQ ID NO 52
<211> LENGTH: 13543
<212> TYPE: DNA
<213> ORGANISM: Artificial Sequence
<220> FEATURE:
<223> OTHER INFORMATION: Plasmid

<400> SEQUENCE: 52

```
tagtaaagcc ctcgctagat tttaatgcgg atgttgcgat tacttcgcca actattgcga        60
taacaagaaa aagccagcct ttcatgatat atctcccaat ttgtgtaggg cttattatgc       120
acgcttaaaa ataataaaag cagacttgac ctgatagttt ggctgtgagc aattatgtgc       180
ttagtgcatc taacgcttga gttaagccgc gccgcgaagc ggcgtcggct tgaacgaatt       240
gttagacatt atttgccgac taccttggtg atctcgcctt tcacgtagtg acaaattct       300 tccaactgat ctgcgcgcga ggccaagcga tcttcttctt gtccaagata agcctgtcta       360
gcttcaagta tgacgggctg atactgggcc ggcaggcgct ccattgccca gtcggcagcg       420
acatccttcg gcgcgatttt gccggttact gcgctgtacc aaatgcggga caacgtaagc       480
actacatttc gctcatcgcc agcccagtcg ggcggcgagt tccatagcgt taaggtttca       540
tttagcgcct caaatagatc ctgttcagga accggatcaa agagttcctc cgccgctgga       600
cctaccaagg caacgctatg ttctcttgct tttgtcagca agatagccag atcaatgtcg       660
atcgtggctg gctcgaagat acctgcaaga atgtcattgc gctgccattc tccaaattgc       720
agttcgcgct tagctggata acgccacgga atgatgtcgt cgtgcacaac aatggtgact       780
tctacagcgc ggagaatctc gctctctcca ggggaagccg aagtttccaa aaggtcgttg       840
atcaaagctc gccgcgttgt ttcatcaagc cttacggtca ccgtaaccag caaatcaata       900
tcactgtgtg gcttcaggcc gccatccact gcggagccgt acaaatgtac ggccagcaac       960
gtcggttcga gatggcgctc gatgacgcca actacctctg atagttgagt cgatacttcg      1020
gcgatcaccg cttccctcat gatgtttaac tttgttttag ggcgactgcc ctgctgcgta      1080
acatcgttgc tgctccataa catcaaacat cgacccacgg cgtaacgcgc ttgctgcttg      1140
gatgcccgag gcatagactg taccccaaaa aaacagtcat aacaagccat gaaaaccgcc      1200
actgcgccgt taccaccgct gcgttcggtc aaggttctgg accagttgcg tgagcgcata      1260
cgctacttgc attacagctt acgaaccgaa caggcttatg tccactgggt tcgtgccttc      1320
atccgtttcc acggtgtgcg tcacccggca accttgggca gcagcgaagt cgaggcattt      1380
ctgtcctggc tggcgaacga gcgcaaggtt cggtctccca cgcatcgtca ggcattggcg      1440
gccttgctgt tcttctacgg caaggtgctg tgcacggatc tgccctggct tcaggagatc      1500
ggaagacctc ggccgtcgcg gcgcttgccg gtggtgctga cccgggatga agtggttcgc      1560
atcctcggtt ttctggaagg cgagcatcgt ttgttcgccc agcttctgta tggaacgggc      1620
```

```
atgcggatca gtgagggttt gcaactgcgg gtcaaggatc tggatttcga tcacggcacg    1680
atcatcgtgc gggagggcaa gggctccaag gatcgggcct tgatgttacc cgagagcttg    1740
gcacccagcc tgcgcgagca ggggaattaa ttcccacggg ttttgctgcc cgcaaacggg    1800
ctgttctggt gttgctagtt tgttatcaga atcgcagatc cggcttcagc cggtttgccg    1860
gctgaaagcg ctatttcttc cagaattgcc atgatttttt ccccacggga ggcgtcactg    1920
gctcccgtgt tgtcggcagc tttgattcga taagcagcat cgcctgtttc aggctgtcta    1980
tgtgtgactg ttgagctgta acaagttgtc tcaggtgttc aatttcatgt tctagttgct    2040
ttgttttact ggtttcacct gttctattag gtgttacatg ctgttcatct gttacattgt    2100
cgatctgttc atggtgaaca gctttgaatg caccaaaaac tcgtaaaagc tctgatgtat    2160
ctatcttttt tacaccgttt tcatctgtgc atatggacag ttttccettt gatatgtaac    2220 ggtgaacagt tgttctactt tgtttgtta gtcttgatgc ttcactgata gatacaagag    2280
ccataagaac ctcagatcct tccgtattta gccagtatgt tctctagtgt ggttcgttgt    2340
ttttgcgtga gccatgagaa cgaaccattg agatcatact tactttgcat gtcactcaaa    2400 aatttttgcct caaaactggt gagctgaatt tttgcagtta aagcatcgtg tagtgttttt    2460
cttagtccgt tatgtaggta ggaatctgat gtaatggttg ttggtatttt gtcaccattc    2520 attttatct ggttgttctc aagttcggtt acgagatcca tttgtctatc tagttcaact    2580
tggaaaatca acgtatcagt cgggcggcct cgcttatcaa ccaccaattt catattgctg    2640
taagtgttta aatctttact tattggtttc aaaacccatt ggttaagcct ttaaactca    2700 tggtagttat tttcaagcat taacatgaac ttaaattcat caaggctaat ctctatattt    2760
gccttgtgag ttttctttg tgttagttct tttaataacc actcataaat cctcatagag    2820
tatttgtttt caaaagactt aacatgttcc agattatatt ttatgaattt ttttaactgg    2880
aaaagataag gcaatatctc ttcactaaaa actaattcta attttttcgct tgagaacttg    2940 gcatagtttg tccactggaa aatctcaaag cctttaacca aaggattcct gatttccaca    3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgatttaa tcactatacc aattgagatg gctagtcaa    3300 tgataattac tagtccttt cctttgagtt gtgggtatct gtaaattctg ctagacccttt   3360 gctggaaaac ttgtaaattc tgctagaccc tctgtaaatt ccgctagacc tttgtgtgtt    3420 tttttgttt atattcaagt ggttataatt tatagaataa agaagaata aaaaagata     3480 aaagaatag atcccagccc tgtgtataac tcactacttt agtcagttcc gcagtattac    3540
aaaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc tttttcgtga cattcagttc gctgcgctca cggctctggc    3720
agtgaatggg ggtaaatggc actacaggcg cctttttatgg attcatgcaa ggaaactacc    3780
cataatacaa gaaaagcccg tcacgggctt ctcaggcgt tttatggcgg gtctgctatg    3840
tggtgctatc tgactttttg ctgttcagca gttcctgccc tctgattttc cagtctgacc    3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
```

```
cgaccggagg cttttgactg ctaggcgatc tgtgctgttt gccacggtat gcagcaccag   4080
cgcgagatta tgggctcgca cgctcgactg tcggacgggg gcactggaac gagaagtcag   4140
gcgagccgtc acgcccttga ctatgccaca tcctgagcaa ataattcaac cactaaacaa   4200
atcaaccgcg tttcccggag gtaaccaagc ttgcggagaa gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta tttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg ggctggagga gcaggggggtc ccctgccaga   4860 ccataaccta tgacggaggc ggtgacgccg ctgcgctggg cgccctggcg gccagaagct   4920
cgcccctgcg ggtgggtatc gggctcagcc cgtccggcga gatagccctc actcatgccc   4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaaggcac caccgccctg tacggcggca   5160
gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
gcaatatggc cgagagcggc ccgttaaaac agttcgtgat cccggggagg aatctctgcct   5460 ctgcccagct gcacgtggcg cgcacccagt cccgtcggct cgaacgcctg ctgacggcca   5520
tggaccgcgc gcatccgctg cgcgacgcgc tcaaacgcta cagcaatcgc ctgtcggatg   5580
ccctgttctc catggcgcga atcgaagaga ctaggcctga tgcttgcgct tgaactggcc   5640
tagcaaacac agaaaaaagc ccgcacctga cagtgcgggc ttttttttc ctaggcgatc   5700 tgtgctgttt gccacggtat gcagcaccag cgcgagatta tgggctcgca cgctcgactg   5760
tcggacgggg gcactggaac gagaagtcag gcgagccgtc acgcccttga ctatgccaca   5820
tcctgagcaa ataattcaac cactaaacaa atcaaccgcg tttcccggag gtaaccaagc   5880
ttcacctttt gagccgatga acaatgaaaa gatcaaaacg atttgcagta ctggcccagc   5940 gcccccgtcaa tcaggacggg ctgattggcg agtggcctga agaggggctg atcgccatgg   6000 acagccccctt tgacccggtc tcttcagtaa aagtggacaa cggtctgatc gtcgaactgg   6060
acggcaaacg ccgggaccag tttgacatga tcgaccgatt tatcgccgat tacgcgatca   6120
acgttgagcg cacagagcag gcaatgcgcc tggaggcggt ggaaatagcc cgtatgctgg   6180
tggatattca cgtcagccgg gaggagatca ttgccatcac taccgccatc acgcggccaa   6240
aagcggtcga ggtgatggcg cagatgaacg tggtggagat gatgatggcg ctgcagaaga   6300
tgcgtgcccg ccggacccc ccaaccagt gccacgtcac caatctcaaa gataatccgg   6360
tgcagattgc cgctgacgcc gccgaggccg ggatccgcgg cttctcagaa caggagacca   6420
```

```
cggtcggtat cgcgcgctac gcgccgttta acgccctggc gctgttggtc ggttcgcagt    6480
gcggccgccc cggcgtgttg acgcagtgct cggtggaaga ggccaccgag ctggagctgg    6540
gcatgcgtgg cttaaccagc tacgccgaga cggtgtcggt ctacggcacc gaagcggtat    6600
ttaccgacgg cgatgatacg ccgtggtcaa aggcgttcct cgcctcggcc tacgcctccc    6660
gcgggttgaa aatgcgctac acctccggca ccggatccga agcgctgatg ggctattcgg    6720
agagcaagtc gatgctctac ctcgaatcgc gctgcatctt cattactaaa ggcgccgggg    6780
ttcagggact gcaaaacggc gcggtgagct gtatcggcat gaccggcgct gtgccgtcgg    6840
gcattcgggc ggtgctggcg gaaaacctga tcgcctctat gctcgacctc gaagtggcgt    6900
ccgccaacga ccagactttc tcccactcgg atattcgccg caccgcgcgc accctgatgc    6960
agatgctgcc gggcaccgac tttatttctc ccggctacag cgcggtgccg aactacgaca    7020
acatgttcgc cggctcgaac ttcgatgcgg aagattttga tgattacaac atcctgcagc    7080
gtgacctgat ggttgacggc ggcctgcgtc cggtgaccga ggcggaaacc attgccattc    7140
gccagaaagc ggcgcgggcg atccaggcgg ttttccgcga gctgggctg ccgccaatcg    7200 ccgacgagga ggtggaggcc gccacctacg cgcacggcag caacgagatg ccgccgcgta    7260
acgtggtgga ggatctgagt gcggtggaag agatgatgaa gcgcaacatc accggcctcg    7320
atattgtcgg cgcgctgagc cgcagcggct ttgaggatat cgccagcaat attctcaata    7380
tgctgcgcca gcgggtcacc ggcgattacc tgcagacctc ggccattctc gatcggcagt    7440
tcgaggtggt gagtgcggtc aacgacatca atgactatca ggggccgggc accggctatc    7500
gcatctctgc cgaacgctgg gcggagatca aaaatattcc gggcgtggtt cagcccgaca    7560
ccattgaata aggcggtatt cctgtgcaac agacaaccca aattcagccc tcttttaccc    7620 tgaaacccg cgagggcggg gtagcttctg ccgatgaacg cgccgatgaa gtggtgatcg    7680
gcgtcggccc tgccttcgat aaacaccagc atcacactct gatcgatatg ccccatggcg    7740
cgatcctcaa agagctgatt gccggggtgg aagaagaggg gcttcacgcc cggtggtgc    7800 gcattctgcg cacgtccgac gtctcctttta tggcctggga tgcggccaac ctgagcggct    7860
cggggatcgg catcggtatc cagtcgaagg ggaccacggt catccatcag cgcgatctgc    7920
tgccgctcag caacctggag ctgttctccc aggcgccgct gctgacgctg agacctacc    7980 ggcagattgg caaaaacgct gcgcgctatg cgcgcaaaga gtcaccttcg ccggtgccgg    8040
tggtgaacga tcagatggtg cggccgaaat ttatggccaa agccgcgcta tttcatatca    8100
aagagaccaa acatgtggtg caggacgccg agcccgtcac cctgcacatc gacttagtaa    8160
gggagtgacc atgagcgaga aaaccatgcg cgtgcaggat tatccgttag ccacccgctg    8220 cccgagcat atcctgacgc ctaccggcaa accattgacc gatattaccc tcgagaaggt    8280
gctctctggc gaggtgggcc cgcaggatgt gcggatctcc cgccagaccc ttgagtacca    8340
ggcgcagatt gccgagcaga tgcagcgcca tgcgtggcg cgcaatttcc gccgcgcggc    8400
ggagcttatc gccattcctg acgagcgcat tctggctatc tataacgcgc tgcgcccgtt    8460
ccgctcctcg caggcggagc tgctggcgat cgccgacgag ctggagcaca cctggcatgc    8520
gacagtgaat gccgccttttg tccgggagtc ggcggaagtg tatcagcagc ggcataagct    8580
gcgtaaagga agctaagcgg aggtcagcat gccgttaata gccgggattg atatcggcaa    8640
cgccaccacc gaggtggcgc tggcgtccga ctacccgcag gcgagggcgt tgttgccag    8700 cgggatcgtc gcgacgacgg gcatgaaagg gacgcgggac aatatcgccg ggaccctcgc    8760
cgcgctggag caggccctgg cgaaaacacc gtggtcgatg agcgatgtct ctcgcatcta    8820
```

```
tcttaacgaa gccgcgccgg tgattggcga tgtggcgatg gagaccatca ccgagaccat    8880
tatcaccgaa tcgaccatga tcggtcataa cccgcagacg ccgggcgggg tgggcgttgg    8940
cgtggggacg actatcgccc tcgggcggct ggcgacgctg ccgccggcgc agtatgccga    9000
ggggtggatc gtactgattg acgacgccgt cgatttcctt gacgccgtgt ggtggctcaa    9060
tgaggcgctc gaccggggga tcaacgtggt ggcggcgatc ctcaaaaagg acgacggcgt    9120
gctggtgaac aaccgcctgc gtaaaaccct gccggtggtg gatgaagtga cgctgctgga    9180
gcaggtcccc gagggggtaa tggcggcggt ggaagtggcc gcgccgggcc aggtggtgcg    9240
gatcctgtcg aatccctacg ggatcgccac cttcttcggg ctaagcccgg aagagaccca    9300
ggccatcgtc cccatcgccc gcgccctgat tggcaaccgt tccgcggtgg tgctcaagac    9360
cccgcagggg gatgtgcagt cgcggtgat cccggcgggc aacctctaca ttagcggcga    9420
aaagcgccgc ggagaggccg atgtcgccga gggcgcggaa gccatcatgc aggcgatgag    9480
cgcctgcgct ccggtacgcg catccgcgg cgaaccgggc acccacgccg gcggcatgct    9540
tgagcgggtg cgcaaggtaa tggcgtccct gaccggccat gagatgagcg cgatatacat    9600
ccaggatctg ctggcggtgg atacgtttat tccgcgcaag gtgcagggcg ggatggccgg    9660
cgagtgcgcc atggagaatg ccgtcgggat ggcggcgatg gtgaaagcgg atcgtctgca    9720
aatgcaggtt atcgcccgcg aactgagcgc ccgactgcag accgaggtgg tggtgggcgg    9780
cgtggaggcc aacatggcca tcgccggggc gttaaccact cccggctgtg cggcgccgct    9840
ggcgatcctc gacctcggcg ccggctcgac ggatgcggcg atcgtcaacg cggaggggca    9900
gataacggcg gtccatctcg ccggggcggg gaatatggtc agcctgttga ttaaaaccga    9960
gctgggcctc gaggatcttt cgctggcgga agcgataaaa aaataccgc tggccaaagt   10020
ggaaagcctg ttcagtattc gtcacagaga atggcgcggtg gagttctttc gggaagccct   10080
cagcccggcg gtgttcgcca aagtggtgta catcaaggag ggcgaactgg tgccgatcga   10140
taacgccagc ccgctggaaa aaattcgtct cgtgcgccgg caggcgaaag agaaagtgtt   10200
tgtcaccaac tgcctgcgcg cgctgcgcca ggtctcaccc ggcggttcca ttcgcgatat   10260
cgcctttgtg gtgctggtgg gcggctcatc gctggacttt gagatcccgc agcttatcac   10320
ggaagccttg tcgcactatg gcgtggtcgc cgggcagggc aatattcggg gaacagaagg   10380
gccgcgcaat gcggtcgcca ccgggctgct actggccggt caggcgaatt aaacgggcgc   10440
tcgcgccagc ctctaggtac aaataaaaaa ggcacgtcag atgacgtgcc ttttttcttg   10500
tctagcgtgc accaatgctt ctggcgtcag gcagccatcg gaagctgtgg tatgctgtgt   10560
caggtcgtaa atcactgcat aattcgtgtc gctcaaggcg cactcccgtt ctggataatg   10620
ttttttgcgc cgacatcata acggttctgg caaatattct gaaatgagct gttgacaatt   10680
aatcatccgg ctcgtataat gtgtggaatt gtgagcggat aacaatttca cacaggaaac   10740
agaccatgac tagtaaggag gacaattcca tggctgctgc tgctgataga ttaaacttaa   10800
cttccggcca cttgaatgct ggtagaaaga gaagttcctc ttctgtttct ttgaaggctg   10860
ccgaaaagcc tttcaaggtt actgtgattg gatctggtaa ctggggtact actattgcca   10920
aggtggttgc cgaaaattgt aagggatacc agaagttttt cgctccaata gtacaaatgt   10980
gggtgttcga agaagagatc aatggtgaaa aattgactga atcataaat actagacatc   11040
aaaacgtgaa atacttgcct ggcatcactc tacccgacaa tttggttgct aatccagact   11100
tgattgattc agtcaaggat gtcgacatca tcgtttttca cattccacat caatttttgc   11160
cccgtatctg tagccaattg aaaggtcatg ttgattcaca cgtcagagct atctcctgtc   11220
```

```
taaagggttt tgaagttggt gctaaaggtg tccaattgct atcctcttac atcactgagg   11280
aactaggtat tcaatgtggt gctctatctg gtgctaacat tgccaccgaa gtcgctcaag   11340
aacactggtc tgaaacaaca gttgcttacc acattccaaa ggatttcaga ggcgagggca   11400
aggacgtcga ccataaggtt ctaaaggcct tgttccacag accttacttc cacgttagtg   11460
tcatcgaaga tgttgctggt atctccatct gtggtgcttt gaagaacgtt gttgccttag   11520
gttgtggttt cgtcgaaggt ctaggctggg gtaacaacgc ttctgctgcc atccaaagag   11580
tcggtttggg tgagatcatc agattcggtc aaatgttttt cccagaatct agagaagaaa   11640
catactacca agagtctgct ggtgttgctg atttgatcac cacctgcgct ggtggtagaa   11700
acgtcaaggt tgctaggcta atggctactt ctggtaagga cgcctgggaa tgtgaaaagg   11760
agttgttgaa tggccaatcc gctcaaggtt taattacctg caagaagtt cacgaatggt   11820
tggaaacatg tggctctgtc gaagacttcc cattatttga agccgtatac caaatcgttt   11880
acaacaacta cccaatgaag aacctgccgg acatgattga agaattagat ctacatgaag   11940
attagattta ttggatccag gaaacagact agaattatgg gattgactac taaacctcta   12000
tctttgaaag ttaacgccgc tttgttcgac gtcgacggta ccattatcat ctctcaacca   12060
gccattgctg cattctggag ggatttcggt aaggacaaac cttatttcga tgctgaacac   12120
gttatccaag tctcgcatgg ttggagaacg tttgatgcca ttgctaagtt cgctccagac   12180
tttgccaatg aagagtatgt taacaaatta gaagctgaaa ttccggtcaa gtacggtgaa   12240
aaatccattg aagtcccagg tgcagttaag ctgtgcaacg ctttgaacgc tctaccaaaa   12300
gagaaatggg ctgtggcaac ttccggtacc cgtgatatgg cacaaaaatg gttcgagcat   12360
ctggaatca ggagaccaaa gtacttcatt accgctaatg atgtcaaaca gggtaagcct   12420
catccagaac catatctgaa gggcaggaat ggcttaggat atccgatcaa tgagcaagac   12480
ccttccaaat ctaaggtagt agtatttgaa gacgctccag caggtattgc cgccggaaaa   12540
gccgccggtt gtaagatcat tggtattgcc actactttcg acttggactt cctaaaggaa   12600
aaaggctgtg acatcattgt caaaaaccac gaatccatca gagttggcgg ctacaatgcc   12660
gaaacagacg aagttgaatt catttttgac gactacttat atgctaagga cgatctgttg   12720
aaatggtaac ccgggctgca ggcatgcaag cttggctgtt ttggcggatg agaagagatt   12780
ttcagcctga tacagattaa atcagaacgc agaagcggtc tgataaaaca gaatttgcct   12840
ggcggcagta gcgcggtggt cccacctgac cccatgccga actcagaagt gaaacgccgt   12900
agcgccgatg gtagtgtggg gtctccccat gcgagagtag ggaactgcca ggcatcaaat   12960
aaaacgaaag gctcagtcga agactgggc cttccgtttt atctgttgtt tgtcggtgaa   13020
cgctctcctg agtaggacaa atccgccggg agcggatttg aacgttgcga agcaacggcc   13080
cggagggtgg cgggcaggac gcccgccata aactgccagg catcaaatta agcagaaggc   13140
catcctgacg gatggccttt ttgcgtttct acaaactcca gctggatcgg gcgctagagt   13200
atacatttaa atggtacccct ctagtcaagg ccttaagtga gtcgtattac ggactggccg   13260
tcgttttaca acgtcgtgac tgggaaaacc ctggcgttac ccaacttaat cgccttgcag   13320
cacatccccc tttcgccagc tggcgtaata gcgaagaggc ccgcaccgat cgcccttccc   13380
aacagttgcg cagcctgaat ggcgaatggc gcctgatgcg gtattttctc cttacgcatc   13440
tgtgcggtat ttcacaccgc atatggtgca ctctcagtac aatctgctct gatgccgcat   13500
agttaagcca gccccgacac ccgccaacac ccgctgacga gct                     13543
```

<210> SEQ ID NO 53

<211> LENGTH: 13543
<212> TYPE: DNA
<213> ORGANISM: Artificial Sequence
<220> FEATURE:
<223> OTHER INFORMATION: Plasmid

<400> SEQUENCE: 53

| | | | | | |
|---|---|---|---|---|---|
| tagtaaagcc | ctcgctagat | tttaatgcgg | atgttgcgat | tacttcgcca | actattgcga | 60 |
| taacaagaaa | aagccagcct | ttcatgatat | atctcccaat | ttgtgtaggg | cttattatgc | 120 |
| acgcttaaaa | ataataaaag | cagacttgac | ctgatagttt | ggctgtgagc | aattatgtgc | 180 |
| ttagtgcatc | taacgcttga | gttaagccgc | gccgcgaagc | ggcgtcggct | tgaacgaatt | 240 |
| gttagacatt | atttgccgac | taccttggtg | atctcgcctt | tcacgtagtg | gacaaattct | 300 |
| tccaactgat | ctgcgcgcga | ggccaagcga | tcttcttctt | gtccaagata | agcctgtcta | 360 |
| gcttcaagta | tgacgggctg | atactgggcc | ggcaggcgct | ccattgccca | gtcggcagcg | 420 |
| acatccttcg | cgcgattttt | gccggttact | gcgctgtacc | aaatgcggga | caacgtaagc | 480 |
| actacatttc | gctcatcgcc | agcccagtcg | ggcggcgagt | tccatagcgt | taaggtttca | 540 |
| tttagcgcct | caaatagatc | ctgttcagga | accggatcaa | agagttcctc | cgccgctgga | 600 |
| cctaccaagg | caacgctatg | ttctcttgct | tttgtcagca | agatagccag | atcaatgtcg | 660 |
| atcgtggctg | gctcgaagat | acctgcaaga | atgtcattgc | gctgccattc | tccaaattgc | 720 |
| agttcgcgct | tagctggata | acgccacgga | atgatgtcgt | cgtgcacaac | aatggtgact | 780 |
| tctacacgcgc | ggagaatctc | gctctctcca | ggggaagccg | aagtttccaa | aaggtcgttg | 840 |
| atcaaagctc | gccgcgttgt | ttcatcaagc | cttacggtca | ccgtaaccag | caaatcaata | 900 |
| tcactgtgtg | gcttcaggcc | gccatccact | gcggagccgt | acaaatgtac | ggccagcaac | 960 |
| gtcggttcga | tggcgctc | gatgacgcca | actacctctg | atagttgagt | cgatacttcg | 1020 |
| gcgatcaccg | cttccctcat | gatgtttaac | tttgttttag | ggcgactgcc | ctgctgcgta | 1080 |
| acatcgttgc | tgctccataa | catcaaacat | cgacccacgg | cgtaacgcgc | ttgctgcttg | 1140 |
| gatgcccgag | gcatagactg | taccccaaaa | aaacagtcat | aacaagccat | gaaaaccgcc | 1200 |
| actgcgccgt | taccaccgct | gcgttcggtc | aaggttctgg | accagttgcg | tgagcgcata | 1260 |
| cgctacttgc | attacagctt | acgaaccgaa | caggcttatg | tccactgggt | tcgtgccttc | 1320 |
| atccgttcc | acggtgtgcg | tcacccggca | accttgggca | gcagcgaagt | cgaggcattt | 1380 |
| ctgtcctggc | tggcgaacga | gcgcaaggtt | tcggtctcca | cgcatcgtca | ggcattggcg | 1440 |
| gccttgctgt | tcttctacgg | caaggtgctg | tgcacggatc | tgccctggct | tcaggagatc | 1500 |
| ggaagacctc | ggccgtcgcg | gcgcttgccg | gtggtgctga | ccccggatga | agtggttcgc | 1560 |
| atcctcggtt | ttctggaagg | cgagcatcgt | ttgttcgccc | agcttctgta | tggaacgggc | 1620 |
| atgcggatca | gtgagggttt | gcaactgcgg | gtcaaggatc | tggatttcga | tcacggcacg | 1680 |
| atcatcgtgc | gggagggcaa | gggctccaag | gatcgggcct | tgatgttacc | cgagagcttg | 1740 |
| gcacccagcc | tgcgcgagca | ggggaattaa | ttcccacggg | ttttgctgcc | cgcaaacggg | 1800 |
| ctgttctggt | gttgctagtt | tgttatcaga | atcgcagatc | cggcttcagc | cggtttgccg | 1860 |
| gctgaaagcg | ctatttcttc | cagaattgcc | atgattttt | ccccacggga | ggcgtcactg | 1920 |
| gctcccgtgt | tgtcggcagc | tttgattcga | taagcagcat | cgcctgtttc | aggctgtcta | 1980 |
| tgtgtgactg | ttgagctgta | acaagttgtc | tcaggtgttc | aatttcatgt | tctagttgct | 2040 |
| ttgttttact | ggtttcacct | gttctattag | gtgttacatg | ctgttcatct | gttacattgt | 2100 |
| cgatctgttc | atggtgaaca | gctttgaatg | caccaaaaac | tcgtaaaagc | tctgatgtat | 2160 |

```
ctatcttttt tacaccgttt tcatctgtgc atatggacag ttttcccttt gatatgtaac    2220
ggtgaacagt tgttctactt ttgtttgtta gtcttgatgc ttcactgata gatacaagag    2280
ccataagaac ctcagatcct tccgtattta gccagtatgt tctctagtgt ggttcgttgt    2340
ttttgcgtga gccatgagaa cgaaccattg agatcatact tactttgcat gtcactcaaa    2400
aattttgcct caaaactggt gagctgaatt tttgcagtta aagcatcgtg tagtgttttt    2460
cttagtccgt tatgtaggta ggaatctgat gtaatggttg ttggtatttt gtcaccattc    2520
atttttatct ggttgttctc aagttcggtt acgagatcca tttgtctatc tagttcaact    2580
tggaaaatca acgtatcagt cgggcggcct cgcttatcaa ccaccaattt catattgctg    2640
taagtgttta aatctttact tattggtttc aaaacccatt ggttaagcct tttaaactca    2700
tggtagttat tttcaagcat taacatgaac ttaaattcat caaggctaat ctctatattt    2760
gccttgtgag ttttcttttg tgttagttct tttaataacc actcataaat cctcatagag    2820
tatttgtttt caaaagactt aacatgttcc agattatatt ttatgaattt ttttaactgg    2880
aaaagataag gcaatatctc ttcactaaaa actaattcta atttttcgct tgagaacttg    2940
gcatagtttg tccactggaa aatctcaaag cctttaacca aaggattcct gatttccaca    3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgatttta tcactatacc aattgagatg ggctagtcaa    3300
tgataattac tagtcctttt cctttgagtt gtgggtatct gtaaattctg ctagaccttt    3360
gctggaaaac ttgtaaattc tgctagaccc tctgtaaatt ccgctagacc tttgtgtgtt    3420 tttttgttt atattcaagt ggttataatt tatagaataa agaaagaata aaaaaagata    3480 aaagaatag atcccagccc tgtgtataac tcactacttt agtcagttcc gcagtattac    3540
aaaaggatgt cgcaaacgct gttttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc tttttcgtga cattcagttc gctgcgctca cggctctggc    3720
agtgaatggg ggtaaatggc actacaggcg ccttttatgg attcatgcaa ggaaactacc    3780
cataatacaa gaaaagcccg tcacgggctt ctcagggcgt tttatggcgg gtctgctatg    3840
tggtgctatc tgacttttg ctgttcagca gttcctgccc tctgattttc cagtctgacc    3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcggacgggg gcactggaac gagaagtcag    4140
gcgagccgtc acgcccttga caatgccaca tcctgagcaa ataattcaac cactaaacaa    4200
atcaaccgcg tttcccggag gtaaccaagc ttgcgggaga gaatgatgaa caagagccaa    4260
caagttcaga caatcaccct ggccgccgcc cagcaaatgg cggcggcggt ggaaaaaaaa    4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
```

```
ctgccagtta tttttaatga gcaggtaatt ggcgccgtcg gcgttagcgg cggtacggtc    4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg gctggagga cagggggtc ccctgccaga    4860 ccataaccta tgacggaggc ggtgacgccg ctgcgctggg cgccctggcg ccagaagct    4920 cgccctgcg ggtgggtatc gggctcagcg cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaaggcac caccgccctg tacgcggca    5160 gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctgggg ctgaactggc cagcgatgcg cggggcctga    5340
cccgcctgag ccagacgatc ggcgaagagg agatacccgc cctggagcgg cttatcgacc    5400
gcaatatggc cgagagcggc ccgttaaaac agttcgtgat cccggggagg aatctcgcct    5460
ctgcccagct gcacgtggcg cgcacccagt cccgtcggct cgaacgcctg ctgacggcca    5520
tggaccgcgc gcatccgctg cgcgacgcgc tcaaacgcta cagcaatcgc ctgtcggatg    5580
ccctgttctc catggcgcga atcgaagaga ctaggcctga tgcttgcgct tgaactggcc    5640
tagcaaacac agaaaaaagc ccgcacctga cagtgcgggc tttttttttc ctaggcgatc    5700
tgtgctgttt gccacggtat gcagcaccag cgcgagatta tgggctcgca cgctcgactg    5760
tcggacgggg gcactggaac gagaagtcag gcgagccgtc acgcccttga caatgccaca    5820
tcctgagcaa ataattcaac cactaaacaa atcaaccgcg tttccggag gtaaccaagc    5880 ttcacctttt gagccgatga acaatgaaaa gatcaaaacg atttgcagta ctggcccagc    5940
gccccgtcaa tcaggacggg ctgattggcg agtggcctga agaggggctg atcgccatgg    6000
acagcccctt tgacccggtc tcttcagtaa aagtggacaa cggtctgatc gtcgaactgg    6060
acggcaaacg ccgggaccag tttgacatga tcgaccgatt tatcgccgat tacgcgatca    6120
acgttgagcg cacagagcag gcaatgcgcc tggaggcggt ggaaatagcc cgtatgctgg    6180
tggatattca cgtcagccgg gaggagatca ttgccatcac taccgccatc acgccggcca    6240
aagcggtcga ggtgatggcg cagatgaacg tggtggagat gatgatgcg ctgcagaaga    6300 tgcgtgcccg ccggaccccc tccaaccagt gccacgtcac caatctcaaa gataatccgg    6360
tgcagattgc cgctgacgcc gccgaggcg ggatccgcgg cttctcagaa caggagacca    6420
cggtcggtat cgcgcgctac gcgccgttta acgccctggc gctgttggtc ggttcgcagt    6480
gcggccgccc cggcgtgttg acgcagtgct cggtggaaga ggccaccgag ctggagctgg    6540
gcatgcgtgg cttaaccagc tacgccgaga cggtgtcggt ctacggcacc gaagcggtat    6600
ttaccgacgg cgatgatacg ccgtggtcaa aggcgttcct cgcctcggcc tacgcctccc    6660
gcgggttgaa aatgcgctac acctccggca ccggatccga agcgctgatg ggctattcgg    6720
agagcaagtc gatgctctac ctcgaatcgc gctgcatctt cattactaaa ggcgccgggg    6780
ttcagggact gcaaaacggc gcggtgagct gtatcggcat gaccggcgct gtgccgtcgg    6840
gcattcgggc ggtgctggcg gaaaacctga tcgcctctat gctcgacctc gaagtggcgt    6900
ccgccaacga ccagactttc tcccactcgg atattcgccg caccgcgcgc accctgatgc    6960
```

```
agatgctgcc gggcaccgac tttattttct ccggctacag cgcggtgccg aactacgaca   7020
acatgttcgc cggctcgaac ttcgatgcgg aagattttga tgattacaac atcctgcagc   7080
gtgacctgat ggttgacggc ggcctgcgtc cggtgaccga ggcggaaacc attgccattc   7140
gccagaaagc ggcgcgggcg atccaggcgg ttttccgcga gctggggctg ccgccaatcg   7200
ccgacgagga ggtggaggcc gccacctacg cgcacggcag caacgagatg ccgccgcgta   7260
acgtggtgga ggatctgagt gcggtggaag agatgatgaa gcgcaacatc accggcctcg   7320
atattgtcgg cgcgctgagc cgcagcggct ttgaggatat cgccagcaat attctcaata   7380
tgctgcgcca gcgggtcacc ggcgattacc tgcagacctc ggccattctc gatcggcagt   7440
tcgaggtggt gagtgcggtc aacgacatca atgactatca ggggccgggc accggctatc   7500
gcatctctgc cgaacgctgg gcggagatca aaaatattcc gggcgtggtt cagcccgaca   7560
ccattgaata aggcggtatt cctgtgcaac agacaaccca aattcagccc tcttttaccc   7620
tgaaaacccg cgagggcggg gtagcttctg ccgatgaacg cgccgatgaa gtggtgatcg   7680
gcgtcggccc tgccttcgat aaacaccagc atcacactct gatcgatatg ccccatggcg   7740
cgatcctcaa agagctgatt gccggggtgg aagaagaggg gcttcacgcc cgggtggtgc   7800
gcattctgcg cacgtccgac gtctccttta tggcctggga tgcggccaac ctgagcggct   7860
cggggatcgg catcggtatc cagtcgaagg ggaccacggt catccatcag cgcgatctgc   7920
tgccgctcag caacctggag ctgttctccc aggcgccgct gctgacgctg gagacctacc   7980
ggcagattgg caaaaacgct gcgcgctatg cgcgcaaaga gtcaccttcg ccggtgccgg   8040
tggtgaacga tcagatggtg cggccgaaat ttatggccaa agccgcgcta tttcatatca   8100
aagagaccaa acatgtggtg caggacgccg agcccgtcac cctgcacatc gacttagtaa   8160
gggagtgacc atgagcgaga aaaccatgcg cgtgcaggat tatccgttag ccacccgctg   8220
cccggagcat atcctgacgc ctaccggcaa accattgacc gatattaccc tcgagaaggt   8280
gctctctggc gaggtgggcc cgcaggatgt gcggatctcc cgccagaccc ttgagtacca   8340
ggcgcagatt gccgagcaga tgcagcgcca tgccggtggcg cgcaatttcc gccgcgcggc   8400
ggagcttatc gccattcctg acgagcgcat tctggctatc tataacgcgc tgcgcccgtt   8460
ccgctcctcg caggcggagc tgctggcgat cgccgacgag ctggagcaca cctggcatgc   8520
gacagtgaat gccgcctttg tccgggagtc ggcggaagtg tatcagcagc ggcataagct   8580
gcgtaaagga agctaagcgg aggtcagcat gccgttaata gccgggattg atatcggcaa   8640
cgccaccacc gaggtggcgc tggcgtccga ctacccgcag gcgagggcgt ttgttgccag   8700
cgggatcgtc gcgacgacgg gcatgaaagg gacgcgggac aatatcgccg ggaccctcgc   8760
cgcgctggag caggccctgg cgaaaacacc gtggtcgatg agcgatgtct ctcgcatcta   8820
tcttaacgaa gccgcgccgg tgattggcga tgtggcgatg gagaccatca ccgagaccat   8880
tatcaccgaa tcgaccatga tcggtcataa cccgcagacg ccgggcgggg tgggcgttgg   8940
cgtggggacg actatcgccc tcgggcggct ggcgacgctg ccggcggcgc agtatgccga   9000
ggggtggatc gtactgattg acgacgccgt cgatttccct gacgccgtgt ggtggctcaa   9060
tgaggcgctc gaccgggggga tcaacgtggt ggcggcgatc ctcaaaaagg acgacggcgt   9120
gctggtgaac aaccgcctgc gtaaaaccct gccggtggtg gatgaagtga cgctgctgga   9180
gcaggtcccc gagggggtaa tggcggcggt ggaagtggcc gcgccgggcc aggtggtgcg   9240
gatcctgtcg aatccctacg ggatcgccac cttcttcggg ctaagcccgg aagagaccca   9300
ggccatcgtc cccatcgccc gcgccctgat tggcaaccgt tccgcggtgg tgctcaagac   9360
```

```
cccgcagggg gatgtgcagt cgcgggtgat cccggcgggc aacctctaca ttagcggcga   9420
aaagcgccgc ggagaggccg atgtcgccga gggcgcggaa gccatcatgc aggcgatgag   9480
cgcctgcgct ccggtacgcg acatccgcgg cgaaccgggc acccacgccg cggcatgct    9540 tgagcggtg cgcaaggtaa tggcgtccct gaccggccat gagatgagcg cgatatacat    9600
ccaggatctg ctggcggtgg atacgtttat tccgcgcaag gtgcagggcg ggatggccgg   9660
cgagtgcgcc atggagaatg ccgtcggat ggcggcgatg gtgaaagcgg atcgtctgca    9720
aatgcaggtt atcgcccgcg aactgagcgc ccgactgcag accgaggtgg tggtgggcgg   9780
cgtggaggcc aacatggcca tcgccggggc gttaaccact cccggctgtg cggcgccgct   9840
ggcgatcctc gacctcggcg ccggctcgac ggatgcggcg atcgtcaacg cggagggca    9900 gataacggcg gtccatctcg ccggggcggg gaatatggtc agcctgttga ttaaaaccga   9960
gctgggcctc gaggatcttt cgctggcgga agcgataaaa aaatacccgc tggccaaagt   10020
ggaaagcctg ttcagtattc gtcacgagaa tggcgcggtg gagttctttc gggaagccct   10080
cagcccggcg gtgttcgcca aagtggtgta catcaaggag ggcgaactgg tgccgatcga   10140
taacgccagc ccgctggaaa aaattcgtct cgtgcgccgg caggcgaaag agaaagtgtt   10200
tgtcaccaac tgcctgcgcg cgctgcgcca ggtctcaccc ggcggttcca ttcgcgatat   10260
cgcctttgtg gtgctggtgg gcggctcatc gctggactt gagatcccgc agcttatcac    10320
ggaagccttg tcgcactatg gcgtggtcgc cgggcagggc aatattcggg aacagaagg    10380 gccgcgcaat gcggtcgcca ccgggctgct actggccggt caggcgaatt aaacgggcgc   10440
tcgcgccagc ctctaggtac aaataaaaaa ggcacgtcag atgacgtgcc ttttttcttg   10500
tctagcgtgc accaatgctt ctggcgtcag gcagccatcg gaagctgtgg tatggctgtg   10560
caggtcgtaa atcactgcat aattcgtgtc gctcaaggcg cactcccgtt ctggataatg   10620
ttttttgcgc cgacatcata acggttctgg caaatattct gaaatgagct gttgacaatt   10680
aatcatccgg ctcgtataat gtgtggaatt gtgagcggat aacaatttca cacaggaaac   10740
agaccatgac tagtaaggag gacaattcca tggctgctgc tgctgataga ttaaacttaa   10800
cttccggcca cttgaatgct ggtagaaaga gaagttcctc ttctgtttct ttgaaggctg   10860
ccgaaaagcc tttcaaggtt actgtgattg gatctggtaa ctggggtact actattgcca   10920
aggtggttgc cgaaaattgt aagggatacc cagaagtttt cgctccaata gtacaaatgt   10980
gggtgttcga agaagagatc aatggtgaaa aattgactga aatcataaat actagacatc   11040
aaaacgtgaa atacttgcct ggcatcactc tacccgacaa tttggttgct aatccagact   11100
tgattgattc agtcaaggat gtcgacatca tcgttttcaa cattccacat caatttttgc   11160
cccgtatctg tagccaattg aaaggtcatg ttgattcaca cgtcagagct atctcctgtc   11220
taaagggttt tgaagttggt gctaaaggtg tccaattgct atcctcttac atcactgagg   11280
aactaggtat tcaatgtggt gctctatctg gtgctaacat tgccaccgaa gtcgctcaag   11340
aacactggtc tgaaacaaca gttgcttacc acattccaaa ggatttcaga ggcgagggca   11400
aggacgtcga ccataaggtt ctaaaggcct tgttccacag accttacttc cacgttagtg   11460
tcatcgaaga tgttgctggt atctccatct gtggtgcttt gaagaacgtt gttgccttag   11520
gttgtggttt cgtcgaaggt ctaggctggg gtaacaacgc ttctgctgcc atccaaagag   11580
tcggtttggg tgagatcatc agattcggtc aaatgttttt cccagaatct agagaagaaa   11640
catactacca agagtctgct ggtgttgctg atttgatcac cacctgcgct ggtggtagaa   11700
acgtcaaggt tgctaggcta atggctactt ctggtaagga cgcctgggaa tgtgaaaagg   11760
```

```
agttgttgaa tggccaatcc gctcaaggtt taattacctg caaagaagtt cacgaatggt    11820
tggaaacatg tggctctgtc gaagacttcc cattatttga agccgtatac caaatcgttt    11880
acaacaacta cccaatgaag aacctgccgg acatgattga agaattagat ctacatgaag    11940
attagattta ttggatccag gaaacagact agaattatgg gattgactac taaacctcta    12000
tctttgaaag ttaacgccgc tttgttcgac gtcgacggta ccattatcat ctctcaacca    12060
gccattgctg cattctggag ggatttcggt aaggacaaac cttatttcga tgctgaacac    12120
gttatccaag tctcgcatgg ttggagaacg tttgatgcca ttgctaagtt cgctccagac    12180
tttgccaatg aagagtatgt taacaaatta gaagctgaaa ttccggtcaa gtacggtgaa    12240
aaatccattg aagtcccagg tgcagttaag ctgtgcaacg ctttgaacgc tctaccaaaa    12300
gagaaatggg ctgtggcaac ttccggtacc cgtgatatgg cacaaaaatg gttcgagcat    12360
ctgggaatca ggagaccaaa gtacttcatt accgctaatg atgtcaaaca gggtaagcct    12420
catccagaac catatctgaa gggcaggaat ggcttaggat atccgatcaa tgagcaagac    12480
ccttccaaat ctaaggtagt agtatttgaa gacgctccag caggtattgc cgccggaaaa    12540
gccgccggtt gtaagatcat tggtattgcc actactttcg acttggactt cctaaaggaa    12600
aaaggctgtg acatcattgt caaaaaccac gaatccatca gagttggcgg ctacaatgcc    12660
gaaacagacg aagttgaatt cattttttgac gactacttat atgctaagga cgatctgttg    12720
aaatggtaac ccgggctgca ggcatgcaag cttggctgtt ttggcggatg agagaagatt    12780
ttcagcctga tacagattaa atcagaacgc agaagcggtc tgataaaaca gaatttgcct    12840
ggcggcagta gcgcggtggt cccacctgac cccatgccga actcagaagt gaaacgccgt    12900
agcgccgatg gtagtgtggg gtctccccat gcgagagtag ggaactgcca ggcatcaaat    12960
aaaacgaaag gctcagtcga aagactgggc ctttcgtttt atctgttgtt tgtcggtgaa    13020
cgctctcctg agtaggacaa atccgccggg agcggatttg aacgttgcga agcaacggcc    13080
cggagggtgg cgggcaggac gcccgccata aactgccagg catcaaatta agcagaaggc    13140
catcctgacg gatggccttt ttgcgtttct acaaactcca gctggatcgg gcgctagagt    13200
atacatttaa atggtaccct ctagtcaagg ccttaagtga gtcgtattac ggactggccg    13260
tcgttttaca acgtcgtgac tgggaaaacc ctggcgttac ccaacttaat cgccttgcag    13320
cacatccccc tttcgccagc tggcgtaata gcgaagaggc ccgcaccgat cgcccttccc    13380
aacagttgcg cagcctgaat ggcgaatggc gcctgatgcg gtattttctc cttacgcatc    13440
tgtgcggtat ttcacaccgc atatggtgca ctctcagtac aatctgctct gatgccgcat    13500
agttaagcca gccccgacac ccgccaacac ccgctgacga gct                      13543

<210> SEQ ID NO 54
<211> LENGTH: 13402
<212> TYPE: DNA
<213> ORGANISM: Artificial Sequence
<220> FEATURE:
<223> OTHER INFORMATION: Plamid

<400> SEQUENCE: 54
tagtaaagcc ctcgctagat tttaatgcgg atgttgcgat tacttcgcca actattgcga      60
taacaagaaa aagccagcct ttcatgatat atctcccaat ttgtgtaggg cttattatgc     120
acgcttaaaa ataataaaag cagacttgac ctgatagttt ggctgtgagc aattatgtgc     180
ttagtgcatc taacgcttga gttaagccgc gccgcgaagc ggcgtcggct tgaacgaatt     240
gttagacatt atttgccgac taccttggtg atctcgcctt tcacgtagtg gacaaattct     300
```

```
tccaactgat ctgcgcgcga ggccaagcga tcttcttctt gtccaagata agcctgtcta    360
gcttcaagta tgacgggctg atactgggcc ggcaggcgct ccattgccca gtcggcagcg    420
acatccttcg gcgcgatttt gccggttact gcgctgtacc aaatgcggga caacgtaagc    480
actacatttc gctcatcgcc agcccagtcg ggcggcgagt tccatagcgt taaggtttca    540
tttagcgcct caaatagatc ctgttcagga accggatcaa agagttcctc cgccgctgga    600
cctaccaagg caacgctatg ttctcttgct tttgtcagca agatagccag atcaatgtcg    660
atcgtggctg gctcgaagat acctgcaaga atgtcattgc gctgccattc tccaaattgc    720
agttcgcgct tagctggata cgccacggaa tgatgtcgt cgtgcacaac aatggtgact    780
tctacagcgc ggagaatctc gctctctcca ggggaagccg aagtttccaa aaggtcgttg    840
atcaaagctc gccgcgttgt ttcatcaagc cttacggtca ccgtaaccag caaatcaata    900
tcactgtgtg gcttcaggcc gccatccact gcggagccgt acaaatgtac ggccagcaac    960 gtcggtcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg taccccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgtttcc acggtgtgcg tcacccgca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgattttt ccccacggga ggcgtcactg   1920
gctcccgtgt tgtcggcagc tttgattcga taagcagcat cgcctgtttc aggctgtcta   1980
tgtgtgactt tgagctgta acaagttgtc tcaggtgttc aatttcatgt tctagttgct   2040 ttgtttact ggtttcacct gttctattag gtgttacatg ctgttcatct gttacattgt   2100
cgatctgttc atggtgaaca gctttgaatg caccaaaaac tcgtaaaagc tctgatgtat   2160 ctatctttt tacaccgttt tcatctgtgc atatggacag ttttcccttt gatatgtaac   2220
ggtgaacagt tgttctactt tgttttgtta gtccttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520 attttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta atctttact tattggtttc aaaacccatt ggttaagcct tttaaactca   2700
```

-continued

```
tggtagttat tttcaagcat taacatgaac ttaaattcat caaggctaat ctctatattt      2760
gccttgtgag ttttcttttg tgttagttct tttaataacc actcataaat cctcatagag      2820
tatttgtttt caaaagactt aacatgttcc agattatatt ttatgaattt ttttaactgg      2880
aaaagataag gcaatatctc ttcactaaaa actaattcta atttttcgct tgagaacttg      2940
gcatagtttg tccactggaa atctcaaag cctttaacca aaggattcct gatttccaca       3000
gttctcgtca tcagctctct ggttgcttta gctaatacac cataagcatt ttccctactg      3060
atgttcatca tctgagcgta ttggttataa gtgaacgata ccgtccgttc tttccttgta     3120
gggttttcaa tcgtggggtt gagtagtgcc acacagcata aaattagctt ggtttcatgc      3180
tccgttaagt catagcgact aatcgctagt tcatttgctt tgaaaacaac taattcagac      3240
atacatctca attggtctag gtgattttaa tcactatacc aattgagatg ggctagtcaa      3300
tgataattac tagtcctttt cctttgagtt gtgggtatct gtaaattctg ctagacccttt    3360 gctggaaaac ttgtaaattc tgctagaccc tctgtaaatt ccgctagacc tttgtgtgtt     3420 tttttgttt atattcaagt ggttataatt tatagaataa agaaagaata aaaaagata       3480 aaagaatag atcccagccc tgtgtataac tcactacttt agtcagttcc gcagtattac      3540
aaaaggatgt cgcaaacgct gtttgctcct ctacaaaaca gaccttaaaa ccctaaaggc     3600
ttaagtagca ccctcgcaag ctcgggcaaa tcgctgaata ttccttttgt ctccgaccat     3660
caggcacctg agtcgctgtc ttttcgtga cattcagttc gctgcgctca cggctctggc     3720
agtgaatggg ggtaaatggc actacaggcg cctttatgg attcatgcaa ggaaactacc     3780
cataatacaa gaaaagcccg tcacgggctt ctcagggcgt tttatggcgg gtctgctatg    3840
tggtgctatc tgacttttg ctgttcagca gttcctgccc tctgattttc cagtctgacc      3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg ctttgactg ctaggcgatc tgtgctgttt ccacggtat gcagcaccag       4080 cgcgagatta tgggctcgca cgctcgactg tcggacgggg gcactggaac gagaagtcag    4140
gcgagccgtc acgcccttga caatgccaca tcctgagcaa ataattcaac cactaaacaa     4200
atcaaccgcg tttcccggag gtaaccaagc ttgcgggaga gaatgatgaa caagagccaa    4260
caagttcaga caatcaccct ggccgccgcc cagcaaatgg cggcggcggt ggaaaaaaaa     4320
gccactgaga tcaacgtggc ggtggtgttt tccgtagttg accgcggagg caacacgctg    4380
cttatccagc ggatggacga ggccttcgtc tccagctgcg atatttcct gaataaagcc     4440 tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta ttttaatga gcaggtaatt ggcgccgtcg gcgttagcgg cggtacggtc     4620
gagcaggatc aattattagc ccagtgcgcc ctggattgtt tttccgcatt ataacctgaa     4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga cagggggtc ccctgccaga    4860 ccataaccta tgacggaggc ggtgacgccg ctgcgctggg cgccctggcg ccagaagct     4920 cgccctgcg ggtgggtatc gggctcagcg cgtccggcga atagccctc actcatgccc      4980 agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
```

```
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcaccctgat gcttgcgctt gaactggcct agcaaacaca gaaaaaagcc    5520
cgcacctgac agtgcgggct ttttttttcc taggcgatct gtgctgtttg ccacggtatg    5580
cagcaccagc gcgagattat gggctcgcac gctcgactgt cggacggggg cactggaacg    5640
agaagtcagg cgagccgtca cgcccttgac aatgccacat cctgagcaaa taattcaacc    5700
actaaacaaa tcaaccgcgt ttcccggagg taaccaagct tcaccttttg agccgatgaa    5760
caatgaaaag atcaaaacga tttgcagtac tggcccagcg ccccgtcaat caggacgggc    5820
tgattggcga gtggcctgaa gaggggctga tcgccatgga cagccccttt gacccggtct    5880
cttcagtaaa agtggacaac ggtctgatcg tcgaactgga cggcaaacgc cgggaccagt    5940
ttgacatgat cgaccgattt atcgccgatt acgcgatcaa cgttgagcgc acagagcagg    6000
caatgcgcct ggaggcggtg gaaatagccc gtatgctggt ggatattcac gtcagccggg    6060
aggagatcat tgccatcact accgccatca cgccggccaa agcggtcgag gtgatggcgc    6120
agatgaacgt ggtggagatg atgatggcgc tgcagaagat gcgtgcccgc cggacccccct    6180
ccaaccagtg ccacgtcacc aatctcaaag ataatccggt gcagattgcc gctgacgccg    6240
ccgaggccgg gatccgcggc ttctcagaac aggagaccac ggtcggtatc gcgcgctacg    6300
cgccgtttaa cgccctggcg ctgttggtcg gttcgcagtg cggccgcccc ggcgtgttga    6360
cgcagtgctc ggtggaagag gccaccgagc tggagctggg catgcgtggc ttaaccagct    6420
acgccgagac ggtgtcggtc tacggcaccg aagcggtatt taccgacggc gatgatacgc    6480
cgtggtcaaa ggcgttcctc gcctcggcct acgcctcccg cggggttgaaa atgcgctaca    6540
cctccggcac cggatccgaa gcgctgatgg gctattcgga gagcaagtcg atgctctacc    6600
tcgaatcgcg ctgcatcttc attactaaag gcgccggggt tcagggactg caaaacggcg    6660
cggtgagctg tatcggcatg accggcgctg tgccgtcggg cattcgggcg gtgctggcgg    6720
aaaacctgat cgcctctatg ctcgacctcg aagtggcgtc cgccaacgac cagactttct    6780
cccactcgga tattcgccgc accgcgcgca ccctgatgca gatgctgccg ggcaccgact    6840
ttattttctc cggctacagc gcggtgccga actacgacaa catgttcgcc ggctcgaact    6900
tcgatgcgga agattttgat gattacaaca tcctgcagcg tgacctgatg gttgacggcg    6960
gcctgcgtcc ggtgaccgag gcggaaacca ttgccattcg ccagaaagcg cgcgggcga    7020
tccaggcggt tttccgcgag ctgggctgc cgccaatcgc cgacgaggag gtggaggccg    7080
ccacctacgc gcacggcagc aacgagatgc cgccgcgtaa cgtggtggag gatctgagtg    7140
cggtggaaga gatgatgaag cgcaacatca ccggcctcga tattgtcggc gcgctgagcc    7200
gcagcggctt tgaggatatc gccagcaata ttctcaatat gctgcgccag cgggtcaccg    7260
gcgattacct gcagacctcg gccattctcg atcggcagtt cgaggtggtg agtgcggtca    7320
acgacatcaa tgactatcag gggccgggca ccggctatcg catctctgcc gaacgctggg    7380
cggagatcaa aaatattccg ggcgtggttc agcccgacac cattgaataa ggcggtattc    7440
ctgtgcaaca gacaacccaa attcagccct cttttaccct gaaaacccgc gagggcgggg    7500
```

```
tagcttctgc cgatgaacgc gccgatgaag tggtgatcgg cgtcggccct gccttcgata   7560
aacaccagca tcacactctg atcgatatgc cccatggcgc gatcctcaaa gagctgattg   7620
ccggggtgga agaagagggg cttcacgccc gggtggtgcg cattctgcgc acgtccgacg   7680
tctcctttat ggcctgggat gcggccaacc tgagcggctc ggggatcggc atcggtatcc   7740
agtcgaaggg gaccacggtc atccatcagc gcgatctgct gccgctcagc aacctggagc   7800
tgttctccca ggcgccgctg ctgacgctgg agacctaccg gcagattggc aaaaacgctg   7860
cgcgctatgc gcgcaaagag tcaccttcgc cggtgccggt ggtgaacgat cagatggtgc   7920
ggccgaaatt tatggccaaa gccgcgctat ttcatatcaa agagaccaaa catgtggtgc   7980
aggacgccga gcccgtcacc ctgcacatcg acttagtaag ggagtgacca tgagcgagaa   8040
aaccatgcgc gtgcaggatt atccgttagc cacccgctgc ccggagcata tcctgacgcc   8100
taccggcaaa ccattgaccg atattaccct cgagaaggtg ctctctggcg aggtgggccc   8160
gcaggatgtg cggatctccc gccagaccct tgagtaccag gcgcagattg ccgagcagat   8220
gcagcgccat gcggtggcgc gcaatttccg ccgcgcggcg gagcttatcg ccattcctga   8280
cgagcgcatt ctggctatct ataacgcgct gcgcccgttc cgctcctcgc aggcggagct   8340
gctggcgatc gccgacgagc tggagcacac ctggcatgcg acagtgaatg ccgcctttgt   8400
ccgggagtcg gcggaagtgt atcagcagcg gcataagctg cgtaaaggaa gctaagcgga   8460
ggtcagcatg ccgttaatag ccgggattga tatcggcaac gccaccaccg aggtggcgct   8520
ggcgtccgac tacccgcagg cgagggcgtt tgttgccagc gggatcgtcg cgacgacggg   8580
catgaaaggg acgcgggaca atatcgccgg gaccctcgcc gcgctggagc aggccctggc   8640
gaaaacaccg tggtcgatga gcgatgtctc tcgcatctat cttaacgaag ccgcgccggt   8700
gattggcgat gtggcgatgg agaccatcac cgagaccatt atcaccgaat cgaccatgat   8760
cggtcataac ccgcagacgc cgggcggggt gggcgttggc gtggggacga ctatcgccct   8820
cgggcggctg gcgacgctgc cggcggcgca gtatgccgag gggtggatcg tactgattga   8880
cgacgccgtc gatttccttg acgccgtgtg tgtggctcaat gaggcgctcg accgggggat   8940
caacgtggtg gcggcgatcc tcaaaaagga cgacggcgtg ctggtgaaca accgcctgcg   9000
taaaaccctg ccggtggtgg atgaagtgac gctgctggag caggtccccg agggggtaat   9060
ggcggcggtg gaagtggccg cgccgggcca ggtggtgcgg atcctgtcga tccctacgg    9120 gatcgccacc ttcttcgggc taagcccgga agagacccag gccatcgtcc ccatcgcccg   9180
cgccctgatt ggcaaccgtt ccgcggtggt gctcaagacc ccgcaggggg atgtgcagtc   9240
gcgggtgatc ccggcgggca acctctacat tagcggcgaa aagcgccgcg gagaggccga   9300
tgtcgccgag ggcgcggaag ccatcatgca ggcgatgagc cctgcgctc cggtacgcga    9360 catccgcggc gaaccgggca cccacgccgg cggcatgctt gagcgggtgc gcaaggtaat   9420
ggcgtccctg accggccatg agatgagcgc gatatacatc caggatctgc tggcggtgga   9480
tacgtttatt ccgcgcaagg tgcagggcgg gatggccggc gagtgcgcca tggagaatgc   9540
cgtcgggatg gcggcgatgg tgaaagcgga tcgtctgcaa atgcaggtta tcgcccgcga   9600
actgagcgcc cgactgcaga ccgaggtggt ggtgggcggc gtggaggcca acatggccat   9660
cgccggggcg ttaaccactc ccggctgtgc ggcgccgctg gcgatcctcg acctcggcgc   9720
cggctcgacg gatgcggcga tcgtcaacgc ggaggggcag ataacggcgg tccatctcgc   9780
cggggcgggg aatatggtca gcctgttgat taaaaccgag ctgggcctcg aggatctttc   9840
gctggcggaa gcgataaaaa aataccccgct ggccaaagtg gaaagcctgt tcagtattcg   9900
```

```
tcacgagaat ggcgcggtgg agttctttcg ggaagccctc agcccggcgg tgttcgccaa   9960
agtggtgtac atcaaggagg gcgaactggt gccgatcgat aacgccagcc cgctggaaaa  10020
aattcgtctc gtgcgccggc aggcgaaaga gaaagtgttt gtcaccaact gcctgcgcgc  10080
gctgcgccag gtctcacccg gcggttccat tcgcgatatc gcctttgtgg tgctggtggg  10140
cggctcatcg ctggactttg agatcccgca gcttatcacg gaagccttgt cgcactatgg  10200
cgtggtcgcc gggcagggca atattcgggg aacagaaggg ccgcgcaatg cggtcgccac  10260
cgggctgcta ctggccggtc aggcgaatta acgggcgct cgcgccagcc tctaggtaca  10320
aataaaaaag gcacgtcaga tgacgtgcct tttttcttgt ctagcgtgca ccaatgcttc  10380
tggcgtcagg cagccatcgg aagctgtggt atggctgtgc aggtcgtaaa tcactgcata  10440
attcgtgtcg ctcaaggcgc actcccgttc tggataatgt tttttgcgcc gacatcataa  10500
cggttctggc aaatattctg aaatgagctg ttgacaatta atcatccggc tcgtataatg  10560
tgtggaattg tgagcggata caatttcac acaggaaaca gaccatgact agtaaggagg  10620
acaattccat ggctgctgct gctgatagat aaacttaac ttccggccac ttgaatgctg  10680
gtagaaagag aagttcctct tctgtttctt gaaggctgc cgaaaagcct tcaaggtta  10740 ctgtgattgg atctggtaac tggggtacta ctattgccaa ggtggttgcc gaaaattgta  10800
agggataccc agaagttttc gctccaatag tacaaatgtg ggtgttcgaa gaagagatca  10860
atggtgaaaa attgactgaa atcataaata ctagacatca aaacgtgaaa tacttgcctg  10920
gcatcactct acccgacaat ttggttgcta atccagactt gattgattca gtcaaggatg  10980
tcgacatcat cgttttcaac attccacatc aattttttgcc ccgtatctgt agccaattga  11040
aaggtcatgt tgattcacac gtcagagcta tctcctgtct aaagggtttt gaagttggtg  11100
ctaaaggtgt ccaattgcta tcctcttaca tcactgagga actaggtatt caatgtggtg  11160
ctctatctgg tgctaacatt gccaccgaag tcgctcaaga acactggtct gaaacaacag  11220
ttgcttacca cattccaaag gatttcagag gcgagggcaa ggacgtcgac cataaggttc  11280
taaaggcctt gttccacaga ccttacttcc acgttagtgt catcgaagat gttgctggta  11340
tctccatctg tggtgctttg aagaacgttg ttgccttagg ttgtggtttc gtcgaaggtc  11400
taggctgggg taacaacgct tctgctgcca tccaaagagt cggtttgggt gagatcatca  11460
gattcggtca aatgttttc ccagaatcta gagaagaaac atactaccaa gagtctgctg  11520
gtgttgctga tttgatcacc acctgcgctg tggtagaaaa cgtcaaggtt gctaggctaa  11580
tggctacttc tggtaaggac gcctgggaat gtgaaaagga gttgttgaat ggccaatccg  11640
ctcaaggttt aattacctgc aaagaagttc acgaatggtt ggaaacatgt ggctctgtcg  11700
aagacttccc attatttgaa gccgtatacc aaatcgttta caacaactac ccaatgaaga  11760
acctgccgga catgattgaa gaattagatc tacatgaaga ttagatttat tggatccagg  11820
aaacagacta gaattatggg attgactact aaacctctat ctttgaaagt taacgccgct  11880
ttgttcgacg tcgacggtac cattatcatc tctcaaccag ccattgctgc attctggagg  11940
gatttcggta aggacaaacc ttatttcgat gctgaacacg ttatccaagt ctcgcatggt  12000
tggagaacgt ttgatgccat tgctaagttc gctccagact ttgccaatga agagtatgtt  12060
aacaaattag aagctgaaat tccggtcaag tacggtgaaa atccattga agtcccaggt  12120 gcagttaagc tgtgcaacgc tttgaacgct ctaccaaaag agaaatgggc tgtggcaact  12180
tccggtaccc gtgatatggc acaaaaatgg ttcgagcatc tgggaatcag agaccaaag  12240 tacttcatta ccgctaatga tgtcaaacag ggtaagcctc atccagaacc atatctgaag  12300
```

```
ggcaggaatg gcttaggata tccgatcaat gagcaagacc cttccaaatc taaggtagta   12360
gtatttgaag acgctccagc aggtattgcc gccggaaaag ccgccggttg taagatcatt   12420
ggtattgcca ctactttcga cttggacttc ctaaaggaaa aaggctgtga catcattgtc   12480
aaaaaccacg aatccatcag agttggcggc tacaatgccg aaacagacga agttgaattc   12540 attttgacg actacttata tgctaaggac gatctgttga aatggtaacc cgggctgcag   12600
gcatgcaagc ttggctgttt tggcggatga gagaagattt tcagcctgat acagattaaa   12660
tcagaacgca gaagcggtct gataaaacag aatttgcctg gcggcagtag cgcggtggtc   12720
ccacctgacc ccatgccgaa ctcagaagtg aaacgccgta gcgccgatgg tagtgtgggg   12780
tctccccatg cgagagtagg gaactgccag gcatcaaata aaacgaaagg ctcagtcgaa   12840
agactgggcc tttcgtttta tctgttgttt gtcggtgaac gctctcctga gtaggacaaa   12900
tccgccggga gcggatttga acgttgcgaa gcaacggccc ggagggtggc gggcaggacg   12960
cccgccataa actgccaggc atcaaattaa gcagaaggcc atcctgacgg atggcctttt   13020
tgcgtttcta caaactccag ctggatcggg cgctagagta tacatttaaa tggtaccctc   13080
tagtcaaggc cttaagtgag tcgtattacg gactggccgt cgttttacaa cgtcgtgact   13140
gggaaaaccc tggcgttacc caacttaatc gccttgcagc acatccccct ttcgccagct   13200
ggcgtaatag cgaagaggcc cgcaccgatc gcccttccca acagttgcgc agcctgaatg   13260
gcgaatggcg cctgatgcgg tatttctcc ttacgcatct gtgcggtatt tcacaccgca   13320
tatggtgcac tctcagtaca atctgctctg atgccgcata gttaagccag ccccgacacc   13380
cgccaacacc cgctgacgag ct                                             13402

<210> SEQ ID NO 55
<211> LENGTH: 14443
<212> TYPE: DNA
<213> ORGANISM: Artificial Sequence
<220> FEATURE:
<223> OTHER INFORMATION: Plasmid

<400> SEQUENCE: 55
ttctgataac aaactagcaa caccagaaca gcccgtttgc gggcagcaaa acccgtggga     60
attaattccc ctgctcgcgc aggctgggtg ccaagctctc gggtaacatc aaggcccgat    120
ccttggagcc cttcttacag agatgaaaaa caaaccgcga cgccaggcgg catcgcggtc    180
tcagagatat gtttacgtag atcgaagagc accggtgttt aaacgcccctt gacgatgcca    240 catcctgagc aaataattca accactaaac aaatcaaccg cgtttcccgg aggtaaccga    300
gctcatgatc ctgtgttgtg gtgaagccct gatcgacatg ctgccccggc agacgacgct    360
gggtgaggcg ggctttgccc cttacgcagg cggagcggtc ttcaacacgg caattgcgct    420
ggggcgtctt ggcgtccctt cagccttttt taccggtctt tccgacgaca tgatgggcga    480
tatcctgcgg gagaccctgc gggccagcaa ggtggatttc agctattgcg ccaccctgtc    540
gcgccccacc accattgcgt tcgttaagct ggttgatggc catgcgacct acgcttttta    600
cgacgagaac accgccggcc ggatgatcac cgaggccgaa cttccggcct tgggagcgga    660
ttgcgaagcg ctgcatttcg gcgccatcag ccttattccc gaaccctgcg gcagcaccta    720
tgaggcgctg atgacgcgcg agcatgagac ccgcgtcatc tcgctcgatc gaacattcg    780 tcccggcttc atccagaaca agcagtcgca catggcccgc atccgccgca tggcggcgat    840
gtctgacatc gtcaagttct cggatgagga cctggcgtgg ttcggtctgg aaggcgacga    900
ggacacgctt gcccgccact ggctgcacca cggtgcaaaa ctcgtcgttg tcacccgtgg    960
```

```
cgccaagggt gccgtgggtt acagcgccaa tctcaaggtg gaagtggcct ccgagcgcgt    1020
cgaagtggtc gatacggtcg cgccggcga tacgttcgat gccggcattc ttgcttcgct    1080
gaaaatgcag ggcctgctga ccaaagcgca ggtggcttcg ctgagcgaag agcagatcag    1140
aaaagctttg gcgcttggcg cgaaagccgc tgcggtcact gtctcgcggg ctggcgcaaa    1200
tccgcctttc gcgcatgaaa tcggtttgtg attaattaaa gcacgcagtc aaacaaaaaa    1260
cccgcgccat tgcgcgggtt tttttatgcc cgaaggcgcg ccagcacgca gtcaaacaaa    1320
aaacccgcgc cattgcgcgg gttttttat gcccgaacgg ccgaggtctt ccgatctcct    1380
gaagccaggg cagatccgtg cacagcacct tgccgtagaa gacagcaag gccgccaatg    1440 cctgacgatg cgtggagacc gaaaccttgc gctcgttcgc cagccaggac agaaatgcct    1500
cgacttcgct gctgcccaag gttgccgggt gacgcacacc gtggaaacgg atgaaggcac    1560
gaacccagtg gacataagcc tgttcggttc gtaagctgta atgcaagtag cgtatgcgct    1620
cacgcaactg gtccagaacc ttgaccgaac gcagcggtgg taacggcgca gtggcggttt    1680
tcatggcttg ttatgactgt ttttttgggg tacagtctat gcctcgggca tccaagcagc    1740
aagcgcgtta cgccgtgggt cgatgtttga tgttatggag cagcaacgat gttacgcagc    1800
agggcagtcg ccctaaaaca aagttaaaca tcatgaggga agcggtgatc gccgaagtat    1860
cgactcaact atcagaggta gttggcgtca tcgagcgcca tctcgaaccg acgttgctgg    1920
ccgtacattt gtacggctcc gcagtggatg gcggcctgaa gccacacagt gatattgatt    1980
tgctggttac ggtgaccgta aggcttgatg aaacaacgcg gcgagctttg atcaacgacc    2040
ttttggaaac ttcggcttcc cctggagaga gcgagattct ccgcgctgta gaagtcacca    2100
ttgttgtgca cgacgacatc attccgtggc gttatccagc taagcgcgaa ctgcaatttg    2160
gagaatggca gcgcaatgac attcttgcag gtatcttcga ccagccacg atcgacattg    2220 atctggctat cttgctgaca aaagcaagag aacatagcgt tgccttggta ggtccagcgg    2280
cggaggaact ctttgatccg gttcctgaac aggatctatt tgaggcgcta aatgaaacct    2340
taacgctatg gaactcgccg cccgactggg ctggcgatga gcgaaatgta gtgcttacgt    2400
tgtcccgcat ttggtacagc gcagtaaccg gcaaaatcgc gccgaaggat gtcgctgccg    2460
actgggcaat ggagcgcctg ccggcccagt atcagcccgt catacttgaa gctagacagg    2520
cttatcttgg acaagaagaa gatcgcttgg cctcgcgcgc agatcagttg gaagaatttg    2580
tccactacgt gaaaggcgag atcaccaagg tagtcggcaa ataatgtcta caattcgtt    2640 caagccgacg ccgcttcgcg gcgcggctta actcaagcgt tagatgcact aagcacataa    2700
ttgctcacag ccaaactatc aggtcaagtc tgcttttatt attttttaagc gtgcataata    2760 agccctacac aaattgggag atatatcatg aaaggctggc ttttcttgt tatcgcaata    2820 gttggcgaag taatcgcaac atccgcatta aaatctagcg agggctttac taagctcgtc    2880
agcgggtgtt ggcgggtgtc ggggctggct taactatgcg gcatcagagc agattgtact    2940
gagagtgcac catatgcggt gtgaaatacc gcacagatgc gtaaggagaa aataccgcat    3000
caggcgccat tcgccattca ggctgcgcaa ctgttgggaa gggcgatcgg tgcgggcctc    3060
ttcgctatta cgccagctgg cgaaaggggg atgtgctgca aggcgattaa gttgggtaac    3120
gccagggttt tcccagtcac gacgttgtaa aacgacggcc agtccgtaat acgactcact    3180
taaggccttg actagagggt accatttaaa tgtatactct agcgcccgat ccagctggag    3240
tttgtagaaa cgcaaaaagg ccatccgtca ggatggcctt ctgcttaatt tgatgcctgg    3300
cagtttatgg cgggcgtcct gcccgccacc ctccggggccg ttgcttcgca acgttcaaat    3360
```

-continued

```
ccgctcccgg cggatttgtc ctactcagga gagcgttcac cgacaaacaa cagataaaac    3420
gaaaggccca gtctttcgac tgagcctttc gttttatttg atgcctggca gttccctact    3480
ctcgcatggg gagacsccac actaccatcg gcgctacggc gtttcacttc tgagttcggc    3540
atggggtcag gtgggaccac cgcgctactg ccgccaggca aattctgttt tatcagaccg    3600
cttctgcgtt ctgatttaat ctgtatcagg ctgaaaatct tctctcatcc gccaaaacag    3660
ccaagcttgc atgcctgcag cccgggttac catttcaaca gatcgtcctt agcatataag    3720
tagtcgtcaa aaatgaattc aacttcgtct gtttcggcat tgtagccgcc aactctgatg    3780
gattcgtggt ttttgacaat gatgtcacag cctttttcct ttaggaagtc caagtcgaaa    3840
gtagtggcaa taccaatgat cttacaaccg gcggcttttc cggcggcaat acctgctgga    3900
gcgtcttcaa atactactac cttagatttg aagggtcttg ctcattgatc ggatatcct    3960 aagccattcc tgcccttcag atatggttct ggatgaggct taccctgttt gacatcatta    4020
gcggtaatga agtactttgg tctcctgatt cccagatgct cgaaccattt ttgtgccata    4080
tcacgggtac cggaagttgc cacagcccat ttctcttttg gtagagcgtt caaagcgttg    4140
cacagcttaa ctgcacctgg gacttcaatg gattttcac cgtacttgac cggaatttca    4200
gcttctaatt tgttaacata ctcttcattg gcaaagtctg gagcgaactt agcaatggca    4260
tcaaacgttc tccaaccatg cgagacttgg ataacgtgtt cagcatcgaa ataaggtttg    4320
tccttaccga aatccctcca gaatgcagca atggctggtt gagagatgat aatggtaccg    4380
tcgacgtcga acaaagcggc gttaactttc aaagatagag gtttagtagt caatcccata    4440
attctagtct gtttcctgga tccaataaat ctaatcttca tgtagatcta attcttcaat    4500
catgtccggc aggttcttca ttgggtagtt gttgtaaacg atttggtata cggcttcaaa    4560
taatgggaag tcttcgacag agccacatgt ttccaaccat tcgtgaactt ctttgcaggt    4620 aattaaaccct tgagcggatt ggccattcaa caactccttt tcacattccc aggcgtcctt    4680
accagaagta gccattagcc tagcaacctt gacgtttcta ccaccagcgc aggtggtgat    4740
caaatcagca acaccagcag actcttggta gtatgtttct tctctagatt ctgggaaaaa    4800
catttgaccg aatctgatga tctcacccaa accgactctt ggatggcag cagaagcgtt    4860 gttaccccag cctagacctt cgacgaaacc acaacctaag gcaacaacgt tcttcaaagc    4920
accacagatg gagataccag caacatcttc gatgacacta acgtggaagt aaggtctgtg    4980
gaacaaggcc tttagaacct tatggtcgac gtccttgccc tcgcctctga aatcctttgg    5040
aatgtggtaa gcaactgttg tttcagacca gtgttcttga gcgacttcgg tggcaatgtt    5100
agcaccagat agagcaccac attgaatacc tagttcctca gtgatgtaag aggatagcaa    5160
ttggacacct ttagcaccaa cttcaaaacc ctttagacag gagatagctc tgacgtgtga    5220
atcaacatga cctttcaatt ggctacagat acggggcaaa aattgatgtg gaatgttgaa    5280
aacgatgatg tcgacatcct tgactgaatc aatcaagtct ggattagcaa ccaaattgtc    5340
gggtagagtg atgccaggca agtatttcac gttttgatgt ctagtattta tgatttcagt    5400
caattttcca ccattgatct cttcttcgaa cacccacatt tgtactattg gagcgaaaac    5460
ttctgggtat cccttacaat tttcggcaac caccttggca atagtagtac cccagttacc    5520
agatccaatc acagtaacct tgaaaggctt ttcggcagcc ttcaaagaaa cagaagagga    5580
acttctcttt ctaccagcat tcaagtggcc ggaagttaag tttaatctat cagcagcagc    5640
agccatggaa ttgtcctcct tactagtcat ggtctgtttc ctgtgtgaaa ttgttatccg    5700
ctcacaattc cacacattat acgagccgga tgattaattg tcaacagctc atttcagaat    5760
```

```
atttgccaga accgttatga tgtcggcgca aaaaacatta tccagaacgg gagtgcgcct   5820
tgagcgacac gaattatgca gtgatttacg acctgcacag ccataccaca gcttccgatg   5880
gctgcctgac gccagaagca ttggtgcacg ctagacaaga aaaaaggcac gtcatctgac   5940
gtgccttttt tatttgtacc tagaggctgg cgcgagcgcc cgtttaattc gcctgaccgg   6000
ccagtagcag cccggtggcg accgcattgc gcggcccttc tgttccccga atattgccct   6060
gcccggcgac cacgccatag tgcgacaagg cttccgtgat aagctgcggg atctcaaagt   6120
ccagcgatga gccgcccacc agcaccacaa aggcgatatc gcgaatggaa ccgccgggtg   6180
agacctggcg cagcgcgcgc aggcagttgg tgacaaacac tttctctttc gcctgccggc   6240
gcacgagacg aattttttcc agcgggctgg cgttatcgat cggcaccagt tcgccctcct   6300
tgatgtacac cactttggcg aacaccgccg ggctgagggc ttcccgaaag aactccaccg   6360
cgccattctc gtgacgaata ctgaacaggc tttccacttt ggccagcggg tatttttta   6420 tcgcttccgc cagcgaaaga tcctcgaggc ccagctcggt tttaatcaac aggctgacca   6480
tattccccgc cccggcgaga tggaccgccg ttatctgccc ctccgcgttg acgatcgccg   6540
catccgtcga gccggcgccg aggtcgagga tcgccagcgg cgccgcacag ccgggagtgg   6600
ttaacgcccc ggcgatggcc atgttggcct ccacgccgcc caccaccacc tcggtctgca   6660
gtcgggcgct cagttcgcgg gcgataacct gcatttgcag acgatccgct ttcaccatcg   6720
ccgccatccc gacggcattc tccatggcgc actcgccggc catcccgccc tgcaccttgc   6780
gcggaataaa cgtatccacc gccagcgat cctggatgta tatcgcgctc atctcatggc   6840
cggtcaggga cgccattacc ttgcgcaccc gctcaagcat gccgccggcg tgggtgcccg   6900
gttcgccgcg gatgtcgcgt accggagcgc aggcgctcat cgcctgcatg atggcttccg   6960
cgccctcggc gacatcggcc tctccgcggc gcttttcgcc gctaatgtag aggttgcccg   7020
ccgggatcac ccgcgactgc acatccccct gcggggtctt gagcaccacc gcggaacggt   7080
tgccaatcag ggcgcgggcg atggggacga tggcctgggt ctcttccggg cttagcccga   7140
agaaggtggc gatcccgtag ggattcgaca ggatccgcac cacctggccc ggcgcggcca   7200
cttccaccgc cgccattacc ccctcgggga cctgctccag cagcgtcact tcatccacca   7260
ccggcagggt tttacgcagg cggttgttca ccagcacgcc gtcgtccttt ttgaggatcg   7320
ccgccaccac gttgatcccc cggtcgagcg cctcattgag ccaccacacg cgtcaagga   7380 aatcgacggc gtcgtcaatc agtacgatcc accctcggc atactgcgcc gccggcagcg   7440
tcgccagccg cccgagggcg atagtcgtcc ccacgccaac gccacccg ccggcgtct   7500 gcgggttatg accgatcatg gtcgattcgg tgataatggt ctcggtgatg gtctccatcg   7560
ccacatcgcc aatcaccggc gcggcttcgt taagatagat gcgagagaca tcgctcatcg   7620
accacggtgt tttcgccagg gcctgctcca gcgcggcgag ggtcccggcg atattgtccc   7680
gcgtcccttt catgcccgtc gtcgcgacga tcccgctggc aacaaacgcc ctcgcctgcg   7740
ggtagtcgga cgccagcgcc acctcggtgg tggcgttgcc gatatcaatc ccggctatta   7800
acggcatgct gacctccgct tagcttcctt tacgcagctt atgccgctgc tgatacactt   7860
ccgccgactc ccggacaaag gcggcattca ctgtcgcatg ccaggtgtgc tccagctcgt   7920
cggcgatcgc cagcagctcc gcctgcgagg agcggaacgg gcgcagcgcg ttatagatag   7980
ccagaatgcg ctcgtcagga atggcgataa gctccgccgc gcggcggaaa ttgcgcgcca   8040
ccgcatggcg ctgcatctgc tcggcaatct gcgcctggta ctcaagggtc tggcgggaga   8100
tccgcacatc ctgcgggccc acctcgccag agagcacctt ctcgagggta atatcggtca   8160
```

```
atggtttgcc ggtaggcgtc aggatatgct ccgggcagcg ggtggctaac ggataatcct    8220
gcacgcgcat ggttttctcg ctcatggtca ctcccttact aagtcgatgt gcagggtgac    8280
gggctcggcg tcctgcacca catgtttggt ctctttgata tgaaatagcg cggctttggc    8340
cataaatttc ggccgcacca tctgatcgtt caccaccggc accggcgaag gtgactcttt    8400
gcgcgcatag cgcgcagcgt ttttgccaat ctgccggtag gtctccagcg tcagcagcgg    8460
cgcctgggag aacagctcca ggttgctgag cggcagcaga tcgcgctgat ggatgaccgt    8520
ggtccccttc gactggatac cgatgccgat ccccgagccg ctcaggttgg ccgcatccca    8580
ggccataaag gagacgtcgg acgtgcgcag aatgcgcacc acccgggcgt gaagcccctc    8640
ttcttccacc ccggcaatca gctctttgag gatcgcgcca tggggcatat cgatcagagt    8700
gtgatgctgg tgtttatcga aggcagggcc gacgccgatc accacttcat cggcgcgttc    8760
atcggcagaa gctacccgc cctcgcgggt tttcaggta aaagagggct gaatttgggt     8820
tgtctgttgc acaggaatac cgccttgttc aatggtgtcg ggctgaacca cgcccggaat    8880
atttttgatc tccgcccagc gttcggcaga gatgcgatag ccggtgcccg gcccctgata    8940
gtcattgatg tcgttgaccg cactcaccac ctcgaactgc cgatcgaaaa tggccgaggt    9000
ctgcaggtaa tcgccggtga cccgctggcg cagcatattg agaatattgc tggcgatatc    9060
ctcaaagccg ctgcggctca gcgcgccgac aatatcgagg ccggtgatgt tgcgcttcat    9120
catctcttcc accgcactca gatcctccac cacgttacgc ggcggcatct cgttgctgcc    9180
gtgcgcgtag gtggcggcct ccacctcctc gtcggcgatt ggcggcagcc ccagctcgcg    9240
gaaaaccgcc tggatcgccc gcgccgcttt ctggcgaatg gcaatggttt ccgcctcggt    9300
caccggacgc aggccgccgt caaccatcag gtcacgctgc aggatgttgt aatcatcaaa    9360
atcttccgca tcgaagttcg agccggcgaa catgttgtcg tagttcggca ccgcgctgta    9420 gccgagaaa ataaagtcgg tgcccggcag catctgcatc agggtgcgcg cggtgcggcg     9480
aatatccgag tgggagaaag tctggtcgtt ggcggacgcc acttcgaggt cgagcataga    9540
ggcgatcagg ttttccgcca gcaccgcccg aatgcccgac ggcacagcgc cggtcatgcc    9600
gatacagctc accgcgccgt tttgcagtcc ctgaaccccg cgcctttag taatgaagat    9660 gcagcgcgat tcgaggtaga gcatcgactt gctctccgaa tagcccatca gcgcttcgga    9720
tccggtgccg gaggtgtagc gcattttcaa cccgcgggag gcgtaggccg aggcgaggaa    9780
cgcctttgac cacggcgtat catcgccgtc ggtaaatacc gcttcggtgc cgtagaccga    9840
caccgtctcg gcgtagctgg ttaagccacg catgcccagc tccagctcgg tggcctcttc    9900
caccgagcac tgcgtcaaca cgccggggcg gccgcactgc gaaccgacca acagcgccag    9960
ggcgttaaac ggcgcgtagc gcgcgatacc gaccgtggtc tcctgttctg agaagccgcg    10020
gatcccggcc tcggcggcgt cagcggcaat ctgcaccgga ttatctttga gattggtgac    10080
gtggcactgg ttgagggggg tccggcgggc acgcatcttc tgcagcgcca tcatcatctc    10140
caccacgttc atctgcgcca tcacctcgac cgctttggcc ggcgtgatgg cggtagtgat    10200
ggcaatgatc tcctcccggc tgacgtgaat atccaccagc atacgggcta tttccaccgc    10260
ctccaggcgc attgcctgct ctgtgcgctc aacgttgatc gcgtaatcgg cgataaatcg    10320
gtcgatcatg tcaaactggt cccggcgttt gccgtccagt tcgacgatca gaccgttgtc    10380 cactttact gaagagaccg ggtcaaaggg gctgtccatg gcgatcagcc cctcttcagg     10440
ccactcgcca atcagcccgt cctgattgac ggggcgctgg gccagtactg caaatcgttt    10500
tgatcttttc attgttcatc ggctcaaaag gtgaagcttg gttacctccg ggaaacgcgg    10560
```

```
ttgatttgtt tagtggttga attatttgct caggatgtgg cattgtcaag ggcgtgacgg    10620
ctcgcctgac ttctcgttcc agtgcccccg tccgacagtc gagcgtgcga gcccataatc    10680
tcgcgctggt gctgcatacc gtggcaaaca gcacagatcg cctaggaaaa aaaaagcccg    10740
cactgtcagg tgcgggcttt tttctgtgtt tgctaggcca gttcaagcgc aagcatcagg    10800
gtgcagctgg gcagaggcga gattcctccc cgggatcacg aactgtttta acgggccgct    10860
ctcggccata ttgcggtcga taagccgctc cagggcggtg atctcctctt cgccgatcgt    10920
ctggctcagg cgggtcaggc cccgcgcatc gctggccagt tcagcccccca gcacgaacag    10980 cgtctgctga atatggtgca ggcttttccg cagcccggcg tcgcgggtcg tggcgtagca    11040
gacgcccagc tgggatatca gttcatcgac ggtgccgtag gcctcgacgc gaatatggtc    11100
tttctcgatg cggctgccgc cgtacagggc ggtggtgcct ttatccccgg tgcgggtata    11160
gatacgatac attcagtttc tctcacttaa cggcaggact ttaaccagct gcccggcgtt    11220
ggcgccgagc gtacgcagtt gatcgtcgct atcggtgacg tgtccggtag ccagcggcgc    11280
gtccgccggc agctgggcat gagtgagggc tatctcgccg gacgcgctga gcccgatacc    11340
cacccgcagg ggcgagcttc tggccgccag ggcgcccagc gcagcggcgt caccgcctcc    11400
gtcataggtt atggtctggc aggggacccc ctgctcctcc agccccagc acagctcatt    11460 gatggcgccg gcatggtgcc cgcgcggatc gtaaaacagg cgtacgcctg gcggtgaaag    11520
cgacatgacg gtcccctcgt taacactcag aatgcctggc ggaacatacg atagctcata    11580
atataccttc tcgcttcagg ttataatgcg gaaaaacaat ccaggcgcca ctgggctaat    11640
aattgatcct gctcgaccgt accgccgcta acgccgacgg cgccaattac ctgctcatta    11700
aaaataactg gcaggccgcc gccaaaaata taattcgct gttggttggt tagctgcaga    11760
ccgtacagag attgtcctgg ctggaccgct gacgtaattt catgggtacc ttgcttcagg    11820
ctgcaggcgc tccaggcttt attcagggaa atatcgcagc tggagacgaa ggcctcgtcc    11880
atccgctgga taagcagcgt gttgcctccg cggtcaacta cggaaaacac caccgccacg    11940
ttgatctcag tggctttttt ttccaccgcc gccgccattt gctgggcggc ggccagggtg    12000
attgtctgaa cttgttggct cttgttcatc attctctccc gcaagcttgg ttacctccgg    12060
gaaacgcggt tgatttgttt agtggttgaa ttatttgctc aggatgtggc attgtcaagg    12120
gcgtgacggc tcgcctgact tctcgttcca gtgcccccgt ccgacagtcg agcgtgcgag    12180
cccataatct cgcgctggtg ctgcataccg tggcaaacag cacagatcgc ctagcagtca    12240
aaagcctccg gtcggaggct tttgactatt taaatgaatt cccgacagta agacgggtaa    12300
gcctgttgat gataccgctg ccttactggg tgcattagcc agtctgaatg acctgtcacg    12360
ggataatccg aagtggtcag actggaaaat cagaggcag gaactgctga acagcaaaaa    12420
gtcagatagc accacatagc agacccgcca taaaacgccc tgagaagccc gtgacgggct    12480
tttcttgtat tatgggtagt ttccttgcat gaatccataa aaggcgcctg tagtgccatt    12540
tacccccatt cactgccaga gccgtgagcg cagcgaactg aatgtcacga aaagacagc    12600 gactcaggtg cctgatggtc ggagacaaaa ggaatattca gcgatttgcc cgagcttgcg    12660
agggtgctac ttaagccttt agggttttaa ggtctgtttt gtagaggagc aaacagcgtt    12720
tgcgacatcc ttttgtaata ctgcggaact gactaaagta gtgagttata cacagggctg    12780
ggatctattc ttttttatctt tttttattct ttctttattc tataaattat aaccacttga    12840
atataaacaa aaaaaacaca caaaggtcta gcggaattta cagagggtct agcagaattt    12900
acaagttttc cagcaaaggt ctagcagaat ttacagatac ccacaactca aggaaaagg    12960
```

-continued

```
actagtaatt atcattgact agcccatctc aattggtata gtgattaaaa tcacctagac   13020
caattgagat gtatgtctga attagttgtt ttcaaagcaa atgaactagc gattagtcgc   13080
tatgacttaa cggagcatga aaccaagcta attttatgct gtgtggcact actcaacccc   13140
acgattgaaa accctacaag gaaagaacgg acggtatcgt tcacttataa ccaatacgct   13200
cagatgatga acatcagtag ggaaaatgct tatggtgtat tagctaaagc aaccagagag   13260
ctgatgacga gaactgtgga aatcaggaat cctttggtta aaggctttga gattttccag   13320
tggacaaact atgccaagtt ctcaagcgaa aaattagaat tagtttttag tgaagagata   13380
ttgccttatc ttttccagtt aaaaaaattc ataaaatata atctggaaca tgttaagtct   13440
tttgaaaaca aatactctat gaggatttat gagtggttat taaaagaact aacacaaaag   13500
aaaactcaca aggcaaatat agagattagc cttgatgaat ttaagttcat gttaatgctt   13560
gaaaataact accatgagtt taaaaggctt aaccaatggg ttttgaaacc aataagtaaa   13620
gatttaaaca cttacagcaa tatgaaattg gtggttgata agcgaggccg cccgactgat   13680
acgttgattt tccaagttga actagataga caaatggatc tcgtaaccga acttgagaac   13740
aaccagataa aaatgaatgg tgacaaaata ccaacaacca ttacatcaga ttcctaccta   13800
cataacggac taagaaaaac actacacgat gctttaactg caaaaattca gctcaccagt   13860
tttgaggcaa aattttgag tgacatgcaa agtaagtatg atctcaatgg ttcgttctca   13920
tggctcacgc aaaaacaacg aaccacacta gagaacatac tggctaaata cggaaggatc   13980
tgaggttctt atggctcttg tatctatcag tgaagcatca agactaacaa acaaagtag   14040 aacaactgtt caccgttaca tatcaaaggg aaaactgtcc atatgcacag atgaaaacgg   14100
tgtaaaaaag atagatacat cagagctttt acgagttttt ggtgcattca aagctgttca   14160
ccatgaacag atcgacaatg taacagatga acagcatgta acacctaata gaacaggtga   14220
aaccagtaaa acaaagcaac tagaacatga aattgaacac ctgagacaac ttgttacagc   14280
tcaacagtca cacatagaca gcctgaaaca ggcgatgctg cttatcgaat caaagctgcc   14340
gacaacacgg gagccagtga cgcctcccgt ggggaaaaaa tcatggcaat tctggaagaa   14400
atagcgcttt cagccggcaa accggctgaa gccggatctg cga                     14443
```

<210> SEQ ID NO 56
<211> LENGTH: 26
<212> TYPE: DNA
<213> ORGANISM: Artificial Sequence
<220> FEATURE:
<223> OTHER INFORMATION: Primer

<400> SEQUENCE: 56
gttaactcat ttggcttcat cacctt                                         26

<210> SEQ ID NO 57
<211> LENGTH: 26
<212> TYPE: DNA
<213> ORGANISM: Artificial Sequence
<220> FEATURE:
<223> OTHER INFORMATION: Primer

<400> SEQUENCE: 57
gttaacatga aaagctcaaa cagtct                                         26

<210> SEQ ID NO 58
<211> LENGTH: 100
<212> TYPE: DNA
<213> ORGANISM: Artificial Sequence
<220> FEATURE:

<223> OTHER INFORMATION: Primer

<400> SEQUENCE: 58
cgtctaccct tgttatacct cacaccgcaa ggagacgatc atgaccaata atccccttc    60 agcacagatt aagcccggcg gtgtaggctg gagctgcttc                         100

<210> SEQ ID NO 59
<211> LENGTH: 100
<212> TYPE: DNA
<213> ORGANISM: Artificial Sequence
<220> FEATURE:
<223> OTHER INFORMATION: Primer

<400> SEQUENCE: 59
gcatcaggca atgaataccc aatgcgacca gcttcttata tcagaacagc cccaacggtt   60
tatccgagta gctcaccagc catatgaata tcctccttag                         100

<210> SEQ ID NO 60
<211> LENGTH: 22
<212> TYPE: DNA
<213> ORGANISM: Artificial Sequence
<220> FEATURE:
<223> OTHER INFORMATION: Primer

<400> SEQUENCE: 60
atgaccaata atccccttc ag                                             22

<210> SEQ ID NO 61
<211> LENGTH: 21
<212> TYPE: DNA
<213> ORGANISM: Artificial Sequence
<220> FEATURE:
<223> OTHER INFORMATION: Primer

<400> SEQUENCE: 61
gcttcttata tcagaacagc c                                             21

<210> SEQ ID NO 62
<211> LENGTH: 23
<212> TYPE: DNA
<213> ORGANISM: Artificial Sequence
<220> FEATURE:
<223> OTHER INFORMATION: Primer

<400> SEQUENCE: 62
ggatctaaag cagaaaaatc tgc                                           23

<210> SEQ ID NO 63
<211> LENGTH: 30
<212> TYPE: DNA
<213> ORGANISM: Artificial Sequence
<220> FEATURE:
<223> OTHER INFORMATION: Primer

<400> SEQUENCE: 63
ttcaagctta aacaactgtt ctcccatacg                                    30

RECOMBINANT BACTERIA HAVING THE ABILITY TO METABOLIZE SUCROSE

FIELD OF THE INVENTION

The invention relates to the fields of microbiology and molecular biology. More specifically, recombinant bacteria having the ability to use sucrose as a carbon source and methods of utilizing such recombinant bacteria to produce products such as glycerol and glycerol-derived products are provided

BACKGROUND OF THE INVENTION

Many commercially useful microorganisms use glucose as their main carbohydrate source. However, a disadvantage of the use of glucose by microorganisms developed for production of commercially desirable products is the high cost of glucose. The use of sucrose and mixed feedstocks containing sucrose and other sugars as carbohydrate sources for microbial production systems would be more commercially desirable because these materials are usually readily available at a lower cost.

A production microorganism can function more efficiently when it can utilize any sucrose present in a mixed feedstock. Therefore, when a production microorganism does not have the ability to utilize sucrose efficiently as a major carbon source, it cannot operate as efficiently. For example, bacterial cells typically show preferential sugar use, with glucose being the most preferred. In artificial media containing mixtures of sugars, glucose is typically metabolized to its entirety ahead of other sugars. Moreover, many bacteria lack the ability to utilize sucrose. For example, less than 50% of *Escherichia coli* (*E. coli*) strains have the ability to utilize sucrose. Thus, when a production microorganism cannot utilize sucrose as a carbohydrate source, it is desirable to engineer the microorganism so that it can utilize sucrose.

Recombinant bacteria that have been engineered to utilize sucrose by incorporation of sucrose utilization genes have been reported. For example, Livshits et al. (U.S. Pat. No. 6,960,455) describe the production of amino acids using *Escherichia coli* strains containing genes encoding a metabolic pathway for sucrose utilization. Additionally, Olson et al. (*Appl. Microbiol. Biotechnol.* 74:1031-1040, 2007) describe *Escherichia coli* strains carrying genes responsible for sucrose degradation, which produce L-tyrosine or L-phenylalanine using sucrose as a carbon source. However, there is a need for bacterial strains that are engineered to utilize sucrose using new sucrose utilization genes and that have an improved ability to utilize sucrose. Additionally, there is a need for bacterial strains that are capable of producing glycerol and glycerol-derived products using sucrose as carbon source.

SUMMARY OF THE INVENTION

In one embodiment, the invention provides a recombinant bacterium comprising in its genome or on at least one recombinant construct:

(a) a nucleotide sequence encoding a polypeptide having sucrose transporter activity, the polypeptide having at least 95% sequence identity, based on a Clustal V method of alignment, when compared to an amino acid sequence as set forth in SEQ ID NO:24; and (b) a nucleotide sequence encoding a polypeptide having sucrose hydrolase activity, the polypeptide having at least 95% sequence identity, based on a Clustal V method of alignment, when compared to an amino acid sequence as set forth in SEQ ID NO:26;

wherein (a) and (b) are each operably linked to the same or a different promoter, further wherein said recombinant bacterium is capable of metabolizing sucrose.

In one embodiment, the recombinant bacterium produces 1,3-propanediol, glycerol, and/or 3-hydroxypropionic acid.

In another embodiment, the invention provides a process for making glycerol, 1,3-propanediol and/or 3-hydroxypropionic acid from sucrose comprising:

a) culturing the recombinant bacterium that produces 1,3-propanediol, glycerol, and/or 3-hydroxypropionic acid, disclosed herein, in the presence of sucrose; and b) optionally, recovering the glycerol, 1,3-propanediol and/or 3-hydroxypropionic acid produced.

BRIEF SEQUENCE DESCRIPTIONS

The following sequences conform with 37 C.F.R. 1.821 1.825 ("Requirements for Patent Applications Containing Nucleotide Sequences and/or Amino Acid Sequence Disclosures—the Sequence Rules") and consistent with World Intellectual Property Organization (WIPO) Standard ST.25 (2009) and the sequence listing requirements of the EPO and PCT (Rules 5.2 and 49.5 (a bis), and Section 208 and Annex C of the Administrative Instructions). The symbols and format used for nucleotide and amino acid sequence data comply with the rules set forth in 37 C.F.R. §1.822.

TABLE A

Summary of Gene and Protein SEQ ID Numbers

| Gene | Coding Sequence SEQ ID NO: | Encoded Protein SEQ ID NO: |
|---|---|---|
| GPD1 from *Saccharomyces cerevisiae* | 1 | 2 |
| GPD2 from *Saccharomyces cerevisiae* | 3 | 4 |
| GPP1 from *Saccharomyces cerevisiae* | 5 | 6 |
| GPP2 from *Saccharomyces cerevisiae* | 7 | 8 |
| dhaB1 from *Klebsiella pneumoniae* | 9 | 10 |
| dhaB2 from *Klebsiella pneumoniae* | 11 | 12 |
| dhaB3 from *Klebsiella pneumoniae* | 13 | 14 |
| aldB from *Escherichia coli* | 15 | 16 |
| aldA from *Escherichia coli* | 17 | 18 |
| aldH from *Escherichia coli* | 19 | 20 |
| galP from *Escherichia coli* | 21 | 22 |
| fruP from *Bacillus licheniformis* 14580 | 23 | 24 |
| fruA from *Bacillus licheniformis* 14580 | 25 | 26 |
| cscB from *Escherichia coli* EC3132 | 27 | 28 |
| cscA from *Escherichia coli* EC3132 | 29 | 30 |
| scrK from *Agrobacterium tumefaciens* | 31 | 32 |
| scrK from *Streptococcus mutans* | 33 | 34 |
| scrK From *Escherichia coli* | 35 | 36 |
| scrK from *Klebsiella pneumoniae* | 37 | 38 |
| cscK from *Escherichia coli* | 39 | 40 |
| cscK from *Enterococcus faecalis* | 41 | 42 |
| HXK1 from *Saccharomyces cerevisiae* | 43 | 44 |
| HXK2 from *Saccharomyces cerevisiae* | 45 | 46 |
| dhaT from *Klebsiella pneumoniae* | 47 | 48 |
| dhaX from *Klebsiella pneumoniae* | 49 | 50 |

SEQ ID NO:51 is the nucleotide sequence of plasmid pSYCO101.

SEQ ID NO:52 is the nucleotide sequence of plasmid pSYCO103.

SEQ ID NO:53 is the nucleotide sequence of plasmid pSYCO106.

SEQ ID NO:54 is the nucleotide sequence of plasmid pSYCO109.

SEQ ID NO:55 is the nucleotide sequence of plasmid pSYCO400/AGRO.

SEQ ID NOs:56-63 are the nucleotide sequences of primers used in the Examples herein.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a cell" includes one or more cells and equivalents thereof known to those skilled in the art, and so forth.

In the context of this disclosure, a number of terms and abbreviations are used. The following definitions are provided.

"Open reading frame" is abbreviated as "ORF".

"Polymerase chain reaction" is abbreviated as "PCR".

"American Type Culture Collection" is abbreviated as "ATCC".

The term "recombinant glycerol-producing bacterium" refers to a bacterium that has been genetically engineered to be capable of producing glycerol and/or glycerol-derived products.

The term "polypeptide having sucrose transporter activity" refers to a polypeptide that is capable of mediating the transport of sucrose into microbial cells.

The term "polypeptide having fructokinase activity" refers to a polypeptide that has the ability to catalyze the conversion of D-fructose+ATP to fructose-phosphate+ADP. Typical of fructokinase is EC 2.7.1.4. Enzymes that have some ability to phosphorylate fructose, whether or not this activity is their predominant activity, may be referred to as a fructokinase. Abbreviations used for genes encoding fructokinases and proteins having fructokinase activity include, for example, "Frk", "scrK", "cscK", "FK", and "KHK". Fructokinase is encoded by the scrK gene in *Agrobacterium tumefaciens* and *Streptococcus mutans*; and by the cscK gene in certain *Escherichia coli* strains.

The term "polypeptide having sucrose hydrolase activity" refers to a polypeptide that has the ability to catalyze the hydrolysis of sucrose to produce glucose and fructose. Such polypeptides are often referred to as "invertases" or "β-fructofuranosidases".

The terms "glycerol derivative" and "glycerol-derived products" are used interchangeably herein and refer to a compound that is synthesized from glycerol or in a pathway that includes glycerol. Examples of such products include 3-hydroxypropionic acid, methylglyoxal, 1,2-propanediol, and 1,3-propanediol.

The term "microbial product" refers to a product that is microbially produced, i.e., the result of a microorganism metabolizing a substance. The product may be naturally produced by the microorganism, or the microorganism may be genetically engineered to produce the product.

The terms "phosphoenolpyruvate-sugar phosphotransferase system", "PTS system", and "PTS" are used interchangeably herein and refer to the phosphoenolpyruvate-dependent sugar uptake system.

The terms "phosphocarrier protein HPr" and "PtsH" refer to the phosphocarrier protein encoded by ptsH in *E. coli*. The terms "phosphoenolpyruvate-protein phosphotransferase" and "PtsI" refer to the phosphotransferase, EC 2.7.3.9, encoded by ptsI in *E. coli*. The terms "glucose-specific IIA component", and "Crr" refer to enzymes designated as EC 2.7.1.69, encoded by crr in *E. coli*. PtsH, PtsI, and Crr comprise the PTS system.

The term "PTS minus" refers to a microorganism that does not contain a PTS system in its native state or a microorganism in which the PTS system has been inactivated through the inactivation of a PTS gene.

The terms "glycerol-3-phosphate dehydrogenase" and "G3PDH" refer to a polypeptide responsible for an enzyme activity that catalyzes the conversion of dihydroxyacetone phosphate (DHAP) to glycerol 3-phosphate (G3P). In vivo G3PDH may be NAD- or NADP-dependent. When specifically referring to a cofactor specific glycerol-3-phosphate dehydrogenase, the terms "NAD-dependent glycerol-3-phosphate dehydrogenase" and "NADP-dependent glycerol-3-phosphate dehydrogenase" will be used. As it is generally the case that NAD-dependent and NADP-dependent glycerol-3-phosphate dehydrogenases are able to use NAD and NADP interchangeably (for example by the enzyme encoded by gpsA), the terms NAD-dependent and NADP-dependent glycerol-3-phosphate dehydrogenase will be used interchangeably. The NAD-dependent enzyme (EC 1.1.1.8) is encoded, for example, by several genes including GPD1, also referred to herein as DAR1 (coding sequence set forth in SEQ ID NO:1; encoded protein sequence set forth in SEQ ID NO:2), or GPD2 (coding sequence set forth in SEQ ID NO:3; encoded protein sequence set forth in SEQ ID NO:4), or GPD3. The NADP-dependent enzyme (EC 1.1.1.94) is encoded, for example, by gpsA.

The terms "glycerol 3-phosphatase", "sn-glycerol 3-phosphatase", "D,L-glycerol phosphatase", and "G3P phosphatase" refer to a polypeptide having an enzymatic activity that is capable of catalyzing the conversion of glycerol 3-phosphate and water to glycerol and inorganic phosphate. G3P phosphatase is encoded, for example, by GPP1 (coding sequence set forth in SEQ ID NO:5; encoded protein sequence set forth in SEQ ID NO:6), or GPP2 (coding sequence set forth in SEQ ID NO:7; encoded protein sequence set forth in SEQ ID NO:8).

The term "glycerol dehydratase" or "dehydratase enzyme" refers to a polypeptide having enzyme activity that is capable of catalyzing the conversion of a glycerol molecule to the product, 3-hydroxypropionaldehyde (3-HPA).

For the purposes of the present invention the dehydratase enzymes include a glycerol dehydratase (E.C. 4.2.1.30) and a diol dehydratase (E.C. 4.2.1.28) having preferred substrates of glycerol and 1,2-propanediol, respectively. Genes for dehydratase enzymes have been identified in *Klebsiella pneumoniae, Citrobacter freundii, Clostridium pasteurianum, Salmonella typhimurium, Klebsiella oxytoca*, and *Lactobacillus reuteri*, among others. In each case, the dehydratase is composed of three subunits: the large or "α" subunit, the medium or "β" subunit, and the small or "γ" subunit. The genes are also described in, for example, Daniel et al. (*FEMS Microbiol. Rev.* 22, 553 (1999)) and Toraya and Mori (*J. Biol. Chem.* 274, 3372 (1999)). Genes encoding the large or "α" (alpha) subunit of glycerol dehydratase include dhaB1 (coding sequence set forth in SEQ ID NO:9, encoded protein sequence set forth in SEQ ID NO:10), gldA and dhaB; genes encoding the medium or "β" (beta) subunit include dhaB2 (coding sequence set forth in SEQ ID NO:11, encoded protein sequence set forth in SEQ ID NO:12), gldB, and dhaC; genes encoding the small or "γ" (gamma) subunit include dhaB3 (coding sequence set forth in SEQ ID NO:13, encoded protein sequence set forth in SEQ ID NO:14), gldC, and dhaE. Other genes encoding the large or "α" subunit of diol dehydratase include pduC and pddA; other genes encoding the medium or "β" subunit include pduD and pddB; and other genes encoding the small or "γ" subunit include pduE and pddC.

Glycerol and diol dehydratases are subject to mechanism-based suicide inactivation by glycerol and some other substrates (Daniel et al., *FEMS Microbiol. Rev.* 22, 553 (1999)). The term "dehydratase reactivation factor" refers to those proteins responsible for reactivating the dehydratase activity.

The terms "dehydratase reactivating activity", "reactivating the dehydratase activity" and "regenerating the dehydratase activity" are used interchangeably and refer to the phenomenon of converting a dehydratase not capable of catalysis of a reaction to one capable of catalysis of a reaction or to the phenomenon of inhibiting the inactivation of a dehydratase or the phenomenon of extending the useful half-life of the dehydratase enzyme in vivo. Two proteins have been identified as being involved as the dehydratase reactivation factor (see, e.g., U.S. Pat. No. 6,013,494 and references therein; Daniel et al., supra; Toraya and Mori, *J. Biol. Chem.* 274, 3372 (1999); and Tobimatsu et al., *J. Bacteriol.* 181, 4110 (1999)). Genes encoding one of the proteins include, for example, orfZ, dhaB4, gdrA, pduG and ddrA. Genes encoding the second of the two proteins include, for example, orfX, orf2b, gdrB, pduH and ddrB.

The terms "1,3-propanediol oxidoreductase", "1,3-propanediol dehydrogenase" and "DhaT" are used interchangeably herein and refer to the polypeptide(s) having an enzymatic activity that is capable of catalyzing the interconversion of 3-HPA and 1,3-propanediol provided the gene(s) encoding such activity is found to be physically or transcriptionally linked to a dehydratase enzyme in its natural (i.e., wild type) setting; for example, the gene is found within a dha regulon as is the case with dhaT from *Klebsiella pneumoniae*. Genes encoding a 1,3-propanediol oxidoreductase include, but are not limited to, dhaT from *Klebsiella pneumoniae, Citrobacter freundii*, and *Clostridium pasteurianum*. Each of these genes encode a polypeptide belonging to the family of type III alcohol dehydrogenases, which exhibits a conserved iron-binding motif, and has a preference for the $NAD^+$/NADH linked interconversion of 3-HPA and 1,3-propanediol (Johnson and Lin, *J. Bacteriol.* 169, 2050 (1987); Daniel et al., *J. Bacteriol.* 177, 2151 (1995); and Leurs et al., *FEMS Microbiol. Lett.* 154, 337 (1997)). Enzymes with similar physical properties have been isolated from *Lactobacillus brevis* and *Lactobacillus buchneri* (Veiga da Dunha and Foster, *Appl. Environ. Microbiol.* 58, 2005 (1992)).

The term "dha regulon" refers to a set of associated polynucleotides or open reading frames encoding polypeptides having various biological activities, including but not limited to a dehydratase activity, a reactivation activity, and a 1,3-propanediol oxidoreductase. Typically a dha regulon comprises the open reading frames dhaR, orfY, dhaT, orfX, orfW, dhaB1, dhaB2, dhaB3, and orfZ as described in U.S. Pat. No. 7,371,558.

The terms "aldehyde dehydrogenase" and "Ald" refer to a polypeptide that catalyzes the conversion of an aldehyde to a carboxylic acid. Aldehyde dehydrogenases may use a redox cofactor such as NAD, NADP, FAD, or PQQ. Typical of aldehyde dehydrogenases is EC 1.2.1.3 (NAD-dependent); EC 1.2.1.4 (NADP-dependent); EC 1.2.99.3 (PQQ-dependent); or EC 1.2.99.7 (FAD-dependent). An example of an NADP-dependent aldehyde dehydrogenase is AldB (SEQ ID NO:16), encoded by the *E. coli* gene aldB (coding sequence set forth in SEQ ID NO:15). Examples of NAD-dependent aldehyde dehydrogenases include AldA (SEQ ID NO:18), encoded by the *E. coli* gene aldA (coding sequence set forth in SEQ ID NO:17); and AldH (SEQ ID NO:20), encoded by the *E. coli* gene aldH (coding sequence set forth in SEQ ID NO:19).

The terms "glucokinase" and "Glk" are used interchangeably herein and refer to a protein that catalyzes the conversion of D-glucose+ATP to glucose 6-phosphate+ADP. Typical of glucokinase is EC 2.7.1.2. Glucokinase is encoded by glk in *E. coli*.

The terms "phosphoenolpyruvate carboxylase" and "Ppc" are used interchangeably herein and refer to a protein that catalyzes the conversion of phosphoenolpyruvate+$H_2O$+$CO_2$ to phosphate+oxaloacetic acid. Typical of phosphoenolpyruvate carboxylase is EC 4.1.1.31. Phosphoenolpyruvate carboxylase is encoded by ppc in *E. coli*.

The terms "glyceraldehyde-3-phosphate dehydrogenase" and "GapA" are used interchangeably herein and refer to a protein having an enzymatic activity capable of catalyzing the conversion of glyceraldehyde 3-phosphate+phosphate+$NAD^+$ to 3-phospho-D-glyceroyl-phosphate+NADH+$H^+$. Typical of glyceraldehyde-3-phosphate dehydrogenase is EC 1.2.1.12. Glyceraldehyde-3-phosphate dehydrogenase is encoded by gapA in *E. coli*.

The terms "aerobic respiration control protein" and "ArcA" are used interchangeably herein and refer to a global regulatory protein. The aerobic respiration control protein is encoded by arcA in *E. coli*.

The terms "methylglyoxal synthase" and "MgsA" are used interchangeably herein and refer to a protein having an enzymatic activity capable of catalyzing the conversion of dihydroxyacetone phosphate to methylglyoxal+phosphate. Typical of methylglyoxal synthase is EC 4.2.3.3. Methylglyoxal synthase is encoded by mgsA in *E. coli*.

The terms "phosphogluconate dehydratase" and "Edd" are used interchangeably herein and refer to a protein having an enzymatic activity capable of catalyzing the conversion of 6-phospho-gluconate to 2-keto-3-deoxy-6-phospho-gluconate+$H_2O$. Typical of phosphogluconate dehydratase is EC 4.2.1.12. Phosphogluconate dehydratase is encoded by edd in *E. coli*.

The term "YciK" refers to a putative enzyme encoded by yciK which is translationally coupled to btuR, the gene encoding Cob(I)alamin adenosyltransferase in *E. coli*.

The term "cob(I)alamin adenosyltransferase" refers to an enzyme capable of transferring a deoxyadenosyl moiety from ATP to the reduced corrinoid. Typical of cob(I)alamin adenosyltransferase is EC 2.5.1.17. Cob(I)alamin adenosyltransferase is encoded by the gene "btuR" in *E. coli*, "cobA" in *Salmonella typhimurium*, and "cobO" in *Pseudomonas denitrificans*.

The terms "galactose-proton symporter" and "GalP" are used interchangeably herein and refer to a protein having an enzymatic activity capable of transporting a sugar and a proton from the periplasm to the cytoplasm. D-glucose is a preferred substrate for GalP. Galactose-proton symporter is encoded by galP in *Escherichia coli* (coding sequence set forth in SEQ ID NO:21, encoded protein sequence set forth in SEQ ID NO:22).

The term "non-specific catalytic activity" refers to the polypeptide(s) having an enzymatic activity capable of catalyzing the interconversion of 3-HPA and 1,3-propanediol and specifically excludes 1,3-propanediol oxidoreductase(s). Typically these enzymes are alcohol dehydrogenases. Such enzymes may utilize cofactors other than $NAD^+$/NADH, including but not limited to flavins such as FAD or FMN. A gene for a non-specific alcohol dehydrogenase (yqhD) is found, for example, to be endogenously encoded and functionally expressed within *E. coli* K-12 strains.

The terms "1.6 long GI promoter", "1.20 short/long GI Promoter", and "1.5 long GI promoter" refer to polynucleotides or fragments containing a promoter from the *Streptomyces lividans* glucose isomerase gene as described in U.S. Pat. No. 7,132,527. These promoter fragments include a mutation which decreases their activities as compared to the wild type *Streptomyces lividans* glucose isomerase gene promoter.

The terms "function" and "enzyme function" are used interchangeably herein and refer to the catalytic activity of an enzyme in altering the rate at which a specific chemical reaction occurs without itself being consumed by the reaction. It is understood that such an activity may apply to a reaction in equilibrium where the production of either product or substrate may be accomplished under suitable conditions.

The terms "polypeptide" and "protein" are used interchangeably herein.

The terms "carbon substrate" and "carbon source" are used interchangeably herein and refer to a carbon source capable of being metabolized by the recombinant bacteria disclosed herein and, particularly, carbon sources comprising sucrose. The carbon source may further comprise other monosaccharides, disaccharides, oligosaccharides; or polysaccharides.

The terms "host cell" and "host bacterium" are used interchangeably herein and refer to a bacterium capable of receiving foreign or heterologous genes and capable of expressing those genes to produce an active gene product.

The term "production microorganism" as used herein refers to a microorganism, including, but not limited to, those that are recombinant, used to make a specific product such as 1,3-propanediol, glycerol, 3-hydroxypropionic acid, polyunsaturated fatty acids, and the like.

As used herein, "nucleic acid" means a polynucleotide and includes a single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably herein and refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof.

"Gene" refers to a nucleic acid fragment that expresses a specific protein, and which may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise genes inserted into a non-native organism, genes introduced into a new location within the native host, or chimeric genes.

The term "native nucleotide sequence" refers to a nucleotide sequence that is normally found in the host microorganism.

The term "non-native nucleotide sequence" refers to a nucleotide sequence that is not normally found in the host microorganism.

The term "native polypeptide" refers to a polypeptide that is normally found in the host microorganism.

The term "non-native polypeptide" refers to a polypeptide that is not normally found in the host microorganism.

The terms "encoding" and "coding" are used interchangeably herein and refer to the process by which a gene, through the mechanisms of transcription and translation, produces an amino acid sequence.

The term "coding sequence" refers to a nucleotide sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence (i.e., ORF) and, 3) a 3' untranslated region (e.g., a terminator) that, in eukaryotes, usually contains a polyadenylation site. The expression cassette(s) is usually included within a vector, to facilitate cloning and transformation. Different organisms, including bacteria, yeast, and fungi, can be transformed with different expression cassettes as long as the correct regulatory sequences are used for each host.

"Transformation" refers to the transfer of a nucleic acid molecule into a host organism, resulting in genetically stable inheritance. The nucleic acid molecule may be a plasmid that replicates autonomously, for example, or it may integrate into the genome of the host organism. Host organisms transformed with the nucleic acid fragments are referred to as "recombinant" or "transformed" organisms or "transformants". "Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. Chimeric genes can be designed for use in suppression by linking a nucleic acid fragment or subfragment thereof, whether or not it encodes an active enzyme, in the sense or antisense orientation relative to a promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein.

The terms "substantially similar" and "corresponds substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences. Moreover, the skilled artisan recognizes that substantially similar nucleic acid sequences encompassed by this invention are also defined by their ability to hybridize (under moderately stringent conditions, e.g., 0.5×SSC (standard sodium citrate), 0.1% SDS (sodium dodecyl sulfate), 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences are two nucleotide sequences wherein the complement of one of the nucleotide sequences typically has about at least 80% sequence identity, or 90% sequence identity, up to and including 100% sequence identity (i.e., fully complementary) to the other nucleotide sequence.

The term "stringent conditions" or "stringent hybridization conditions" includes reference to conditions under which a probe will selectively hybridize to its target sequence. Probes are typically single stranded nucleic acid sequences which are complementary to the nucleic acid sequences to be detected. Probes are "hybridizable" to the nucleic acid sequence to be detected. Generally, a probe is less than about 1000 nucleotides in length, optionally less than 500 nucleotides in length.

Hybridization methods are well defined. Typically the probe and sample are mixed under conditions which will permit nucleic acid hybridization. This involves contacting the probe and sample in the presence of an inorganic or organic salt under the proper concentration and temperature conditions. Optionally a chaotropic agent may be added. Nucleic acid hybridization is adaptable to a variety of assay formats. One of the most suitable is the sandwich assay format. A primary component of a sandwich-type assay is a solid support. The solid support has adsorbed to it or covalently coupled to it an immobilized nucleic acid probe that is unlabeled and complementary to one portion of the sequence.

Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the thermal melting point ($T_m$) can be approximated from the equation of Meinkoth et al., *Anal. Biochem.* 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, *CABIOS*. 5:151-153 (1989); Higgins, D. G. et al., *Comput. Appl. Biosci.* 8:189-191 (1992)) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, supra; Higgins, D. G. et al., supra) and found in the MegAlign™ v6.1 program of the LASERGENE bioinformatics computing suite (DNASTAR Inc., Madison, Wis.). Default parameters for multiple alignment correspond to GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB. After alignment of the sequences using the Clustal W program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

Thus, the invention encompasses more than the specific exemplary nucleotide sequences disclosed herein. For example, alterations in the gene sequence which reflect the degeneracy of the genetic code are contemplated. Also, it is well known in the art that alterations in a gene which result in the production of a chemically equivalent amino acid at a given site, but do not affect the functional properties of the encoded protein are common. Substitutions are defined for the discussion herein as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize under stringent conditions, as defined above.

Preferred substantially similar nucleic acid fragments of the instant invention are those nucleic acid fragments whose nucleotide sequences are at least 70% identical to the nucleotide sequence of the nucleic acid fragments reported herein. More preferred nucleic acid fragments are at least 90% identical to the nucleotide sequence of the nucleic acid fragments reported herein. Most preferred are nucleic acid fragments that are at least 95% identical to the nucleotide sequence of the nucleic acid fragments reported herein.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, may now use all or a substantial portion of the disclosed sequences for purposes known to those skilled in this art.

The term "complementary" describes the relationship between two sequences of nucleotide bases that are capable of Watson-Crick base-pairing when aligned in an anti-parallel orientation. For example, with respect to DNA, adenosine is capable of base-pairing with thymine and cytosine is capable of base-pairing with guanine. Accordingly, the instant invention may make use of isolated nucleic acid molecules that are complementary to the complete sequences as reported in the accompanying Sequence Listing and the specification as well as those substantially similar nucleic acid sequences.

The term "isolated" refers to a polypeptide or nucleotide sequence that is removed from at least one component with which it is naturally associated.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

"3' non-coding sequences", "transcription terminator" and "termination sequences" are used interchangeably herein and refer to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described infra.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

A "plasmid" or "vector" is an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "genetically altered" refers to the process of changing hereditary material by genetic engineering, transformation and/or mutation.

The term "recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation, natural transduction, natural transposition) such as those occurring without deliberate human intervention.

The terms "recombinant construct", "expression construct", "chimeric construct", "construct", and "recombinant DNA construct", are used interchangeably herein. A recombinant construct comprises an artificial combination of nucleic acid fragments, e.g., regulatory and coding sequences that are not found together in nature. For example, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events may result in different levels and patterns of expression (Jones et al., *EMBO J.* 4:2411-2418 (1985); De Almeida et al., *Mol. Gen. Genetics* 218:78-86 (1989)), and thus that multiple events may need be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., an mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The term "homologous" refers to proteins or polypeptides of common evolutionary origin with similar catalytic function. The invention may include bacteria producing homologous proteins via recombinant technology.

Disclosed herein are recombinant bacteria that have been engineered to utilize sucrose using new sucrose utilization genes from *Bacillus licheniformis*. Specifically, the recombinant bacteria disclosed herein comprise in their genome or on at least one recombinant construct: a nucleotide sequence encoding a polypeptide having sucrose transporter activity, the polypeptide having at least 95% sequence identity, based on a Clustal V method of alignment, when compared to an amino acid sequence as set forth in SEQ ID NO:24; and a nucleotide sequence encoding a polypeptide having sucrose hydrolase activity, the polypeptide having at least 95% sequence identity, based on a Clustal V method of alignment, when compared to an amino acid sequence as set forth in SEQ ID NO:26. The nucleotide sequences are each operably linked to the same or a different promoter. In some embodiments, the recombinant bacteria are capable of metabolizing sucrose to produce glycerol and/or glycerol-derived products.

Suitable host bacteria for use in the construction of the recombinant bacteria disclosed herein include, but are not limited to, organisms of the genera: *Escherichia, Streptococcus, Agrobacterium, Bacillus, Corynebacterium, Lactobacillus, Clostridium, Gluconobacter, Citrobacter, Enterobacter, Klebsiella, Aerobacter, Methylobacter, Salmonella, Streptomyces,* and *Pseudomonas.*

In one embodiment, the host bacterium is selected from the genera: *Escherichia, Klebsiella, Citrobacter,* and *Aerobacter.*

In another embodiment, the host bacterium is *Escherichia coli.*

In some embodiments, the host bacterium is PTS minus. In these embodiments, the host bacterium is PTS minus in its native state, or may be rendered PTS minus through inactivation of a PTS gene as described below.

In production microorganisms, it is sometimes desirable to unlink the transport of sugars and the use of phosphoenolpyruvate (PEP) for phosphorylation of the sugars being transported.

The term "down-regulated" refers to reduction in, or abolishment of, the activity of active protein(s), as compared to the activity of the wildtype protein(s). The PTS may be inactivated (resulting in a "PTS minus" organism) by down-regulating expression of one or more of the endogenous genes encoding the proteins required in this type of transport. Down-regulation typically occurs when one or more of these genes has a "disruption", referring to an insertion, deletion, or targeted mutation within a portion of that gene, that results in either a complete gene knockout such that the gene is deleted from the genome and no protein is translated or a protein has been translated such that it has an insertion, deletion, amino acid substitution or other targeted mutation. The location of the disruption in the protein may be, for example, within the N-terminal portion of the protein or within the C-terminal portion of the protein. The disrupted protein will have impaired activity with respect to the protein that was not disrupted, and can be non-functional. Down-regulation that results in low or lack of expression of the protein, could also result via manipulating the regulatory sequences, transcription and translation factors and/or signal transduction pathways or by use of sense, antisense or RNAi technology, etc.

Sucrose transporter polypeptides are polypeptides that are capable of mediating the transport of sucrose into microbial cells. Sucrose transport polypeptides are known in the art, for example the CscB polypeptide from *E. coli* wild-type strain EC3132 (set forth in SEQ ID NO:28), encoded by the cscB gene (coding sequence set forth in SEQ ID NO:27), as described by Jahreis et al. (*J. Bacteriol.* 184:5307-5316, 2002). The fruP gene from *Bacillus licheniformis* ATCC® 14580 (coding sequence set forth in SEQ ID NO:23) encodes a polypeptide (set forth in SEQ ID NO:24) that is 39% identical to the known *Escherichia coli* strain EC3132 sucrose transport protein, CscB. However, there is no known activity demonstrated for this polypeptide.

In one embodiment, the nucleotide sequence encoding a polypeptide having sucrose transporter activity has at least 95% sequence identity, based on BLASTN method of alignment, when compared to a nucleotide sequence as set forth in SEQ ID NO:23.

In another embodiment, the nucleotide sequence encoding a polypeptide having sucrose transporter activity has the nucleotide sequence set forth in SEQ ID NO:23.

In one embodiment, the polypeptide having sucrose transporter activity has at least 95% sequence identity, based on a Clustal V method of alignment, when compared to an amino acid sequence as set forth in SEQ ID NO:24.

In another embodiment, the polypeptide having sucrose transporter activity has the amino acid sequence set forth in SEQ ID NO:24.

Polypeptides having sucrose hydrolase activity have the ability to catalyze the hydrolysis of sucrose to produce fructose and glucose. Polypeptides having sucrose hydrolase activity are known, and include, CscA from *E. coli* wild-type strain EC3132 (set forth in SEQ ID NO:30), encoded by gene cscA (coding sequence set forth in SEQ ID NO:29), as described by Jahreis et al. (*J. Bacteriol.* 184:5307-5316, 2002). The fruA gene from *Bacillus licheniformis* ATCC® 14580 (coding sequence set forth in SEQ ID NO:25) encodes a polypeptide (set forth in SEQ ID NO:26) that is 43% identical to the known *Escherichia coli* strain EC3132 sucrose hydrolase, CscA. However, there is no known activity demonstrated for this polypeptide.

In one embodiment, the nucleotide sequence encoding a polypeptide having sucrose hydrolase activity has at least 95% sequence identity, based on BLASTN method of alignment, when compared to a nucleotide sequence as set forth in SEQ ID NO:25.

In another embodiment, the nucleotide sequence encoding a polypeptide having sucrose hydrolase activity has the nucleotide sequence set forth in SEQ ID NO:25.

In one embodiment, the polypeptide having sucrose hydrolase activity has at least 95% sequence identity, based on a Clustal V method of alignment, when compared to an amino acid sequence as set forth in SEQ ID NO:26.

In another embodiment, the polypeptide having sucrose hydrolase activity has the amino acid sequence set forth in SEQ ID NO:26.

The recombinant bacteria disclosed herein may further comprise in their genome or on at least one recombinant construct, a nucleotide sequence encoding a polypeptide having fructokinase activity to enable the bacteria to utilize the fructose produced by the hydrolysis of sucrose. Polypeptides having fructokinase activity include fructokinases (designated EC 2.7.1.4) and various hexose kinases having fructose phosphorylating activity (EC 2.7.1.3 and EC 2.7.1.1). Fructose phosphorylating activity may be exhibited by hexokinases and ketohexokinases. Representative genes encoding polypeptides from a variety of microorganisms, which may be used to construct the recombinant bacteria disclosed herein, are listed in Table 1. One skilled in the art will know that proteins that are substantially similar to a protein which is able to phosphorylate fructose (such as encoded by the genes listed in Table 1) may also be used.

TABLE 1

Sequences Encoding Enzymes with Fructokinase Activity

| Source | Gene Name | EC Number | Nucleotide SEQ ID NO: | Protein SEQ ID NO: |
|---|---|---|---|---|
| *Agrobacterium tumefaciens* | scrK (fructokinase) | 2.7.1.4 | 31 | 32 |
| *Streptococcus mutans* | scrK (fructokinase) | 2.7.1.4 | 33 | 34 |
| *Escherichia coli* | scrK (fructokinase | 2.7.1.4 | 35 | 36 |
| *Klebsiella pneumoniae* | scrK (fructokinase | 2.7.1.4 | 37 | 38 |
| *Escherichia coli* | cscK (fructokinase) | 2.7.1.4 | 39 | 40 |
| *Enterococcus faecalis* | cscK (fructokinase) | 2.7.1.4 | 41 | 42 |
| *Saccharomyces cerevisiae* | HXK1 (hexokinase) | 2.7.1.1 | 43 | 44 |
| *Saccharomyces cerevisiae* | HXK2 (hexokinase) | 2.7.1.1 | 45 | 46 |

In one embodiment, the polypeptide having fructokinase activity has at least 95% sequence identity, based on the Clustal V method of alignment, to an amino acid sequence as set forth in SEQ ID NO:32, SEQ ID NO:34, SEQ ID NO:36, SEQ ID NO:38, SEQ ID NO:40, SEQ ID NO:42, SEQ ID NO:44, or SEQ ID NO:46.

In another embodiment, the polypeptide having fructokinase activity has the amino acid sequence set forth in SEQ ID NO:40.

The coding sequence of the genes encoding polypeptides having sucrose transporter activity and polypeptides having sucrose hydrolase activity may be used to isolate nucleotide sequences encoding homologous polypeptides from the same or other microbial species. For example, homologs of the genes may be identified using sequence analysis software, such as BLASTN, to search publically available nucleic acid sequence databases. Additionally, the isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202; ligase chain reaction (LCR), Tabor, S. et al., *Proc. Acad. Sci.* USA 82, 1074, 1985); or strand displacement amplification (SDA), Walker, et al., *Proc. Natl. Acad. Sci. U.S.A.*, 89: 392, (1992)). For example, the nucleotide sequence encoding the polypeptides described above may be employed as a hybridization probe for the identification of homologs.

One of ordinary skill in the art will appreciate that genes encoding these polypeptides isolated from other sources may also be used in the recombinant bacteria disclosed herein. Additionally, variations in the nucleotide sequences encoding the polypeptides may be made without affecting the amino acid sequence of the encoded polypeptide due to codon degeneracy, and that amino acid substitutions, deletions or additions that produce a substantially similar protein may be included in the encoded protein.

The nucleotide sequences encoding the polypeptides having sucrose transporter activity and polypeptides having sucrose hydrolase activity may be isolated using PCR (see, e.g., U.S. Pat. No. 4,683,202) and primers designed to bound the desired sequence, for example as described in Example 1 herein. Other methods of gene isolation are well known to one skilled in the art such as by using degenerate primers or heterologous probe hybridization. The nucleotide sequences can also be chemically synthesized or purchased from vendors such as DNA2.0 Inc. (Menlo Park, Calif.).

Expression of the polypeptides may be effected using one of many methods known to one skilled in the art. For example, the nucleotide sequences encoding the polypeptides described above may be introduced into the bacterium on at least one multicopy plasmid, or by integrating one or more copies of the coding sequences into the host genome. The nucleotide sequences encoding the polypeptides may be introduced into the host bacterium separately (e.g., on separate plasmids) or in any combination (e.g., on a single plasmid, as described in the Examples herein).

The introduced coding regions that are either on a plasmid(s) or in the genome may be expressed from at least one highly active promoter. An integrated coding region may either be introduced as a part of a chimeric gene having its own promoter, or it may be integrated adjacent to a highly active promoter that is endogenous to the genome or in a highly expressed operon. Suitable promoters include, but are not limited to, CYC1, HIS3, GAL1, GAL10, ADH1, PGK, PHO5, GAPDH, ADC1, TRP1, URA3, LEU2, ENO, and lac, ara, tet, trp, $IP_L$, $IP_R$, T7, tac, and trc (useful for expression in

*Escherichia coli*) as well as the amy, apr, npr promoters and various phage promoters useful for expression in *Bacillus*. The promoter may also be the *Streptomyces lividans* glucose isomerase promoter or a variant thereof, described by Payne et al. (U.S. Pat. No. 7,132,527).

In one embodiment, the recombinant bacteria disclosed herein are capable of producing glycerol. Biological processes for the preparation of glycerol using carbohydrates or sugars are known in yeasts and in some bacteria, other fungi, and algae. Both bacteria and yeasts produce glycerol by converting glucose or other carbohydrates through the fructose-1,6-bisphosphate pathway in glycolysis. In the method of producing glycerol disclosed herein, host bacteria may be used that naturally produce glycerol. In addition, bacteria may be engineered for production of glycerol and glycerol derivatives. The capacity for glycerol production from a variety of substrates may be provided through the expression of the enzyme activities glycerol-3-phosphate dehydrogenase (G3PDH) and/or glycerol-3-phosphatase as described in U.S. Pat. No. 7,005,291. Genes encoding these proteins that may be used for expressing the enzyme activities in a host bacterium are described in U.S. Pat. No. 7,005,291. Suitable examples of genes encoding polypeptides having glycerol-3-phosphate dehydrogenase activity include, but are not limited to, GPD1 from *Saccharomyces cerevisiae* (coding sequence set forth in SEQ ID NO:1, encoded protein sequence set forth in SEQ ID NO:2) and GPD2 from *Saccharomyces cerevisiae* (coding sequence set forth in SEQ ID NO:3, encoded protein sequence set forth in SEQ ID NO:4). Suitable examples of genes encoding polypeptides having glycerol-3-phosphatase activity include, but are not limited to, GPP1 from *Saccharomyces cerevisiae* (coding sequence set forth in SEQ ID NO:5, encoded protein sequence set forth in SEQ ID NO:6) and GPP2 from *Saccharomyces cerevisiae* (coding sequence set forth in SEQ ID NO:7, encoded protein sequence set forth in SEQ ID NO:8).

Increased production of glycerol may be attained through reducing expression of target endogenous genes. Down-regulation of endogenous genes encoding glycerol kinase and glycerol dehydrogenase activities further enhance glycerol production as described in U.S. Pat. No. 7,005,291. Increased channeling of carbon to glycerol may be accomplished by reducing the expression of the endogenous gene encoding glyceraldehyde 3-phosphate dehydrogenase, as described in U.S. Pat. No. 7,371,558. Down-regulation may be accomplished by using any method known in the art, for example, the methods described above for down-regulation of genes of the PTS system.

Glycerol provides a substrate for microbial production of useful products. Examples of such products, i.e., glycerol derivatives include, but are not limited to, 3-hydroxypropionic acid, methylglyoxal, 1,2-propanediol, and 1,3-propanediol.

In another embodiment, the recombinant bacteria disclosed herein are capable of producing 1,3-propanediol. The glycerol derivative 1,3-propanediol is a monomer having potential utility in the production of polyester fibers and the manufacture of polyurethanes and cyclic compounds. 1,3-Propanediol can be produced by a single microorganism by bioconversion of a carbon substrate other than glycerol or dihydroxyacetone, as described in U.S. Pat. No. 5,686,276. In this bioconversion, glycerol is produced from the carbon substrate, as described above. Glycerol is converted to the intermediate 3-hydroxypropionaldehyde by a dehydratase enzyme, which can be encoded by the host bacterium or can be introduced into the host by recombination. The dehydratase can be glycerol dehydratase (E.C. 4.2.1.30), diol dehydratase (E.C. 4.2.1.28) or any other enzyme able to catalyze this conversion. A suitable example of genes encoding the "α" (alpha), "β" (beta), and "γ" (gamma) subunits of a glycerol dehydratase include, but are not limited to dhaB1 (coding sequence set forth in SEQ ID NO:9), dhaB2 (coding sequence set forth in SEQ ID NO:11), and dhaB3 (coding sequence set forth in SEQ ID NO:13), respectively, from *Klebsiella pneumoniae*. The further conversion of 3-hydroxypropionaldehyde to 1,3-propandeiol can be catalyzed by 1,3-propanediol dehydrogenase (E.C. 1.1.1.202) or other alcohol dehydrogenases. A suitable example of a gene encoding a 1,3-propanediol dehydrogenase is dhaT from *Klebsiella pneumoniae* (coding sequence set forth in SEQ ID NO:47, encoded protein sequence set forth in SEQ ID NO:48).

Bacteria can be recombinantly engineered to provide more efficient production of glycerol and the glycerol derivative 1,3-propanediol. For example, U.S. Pat. No. 7,005,291 discloses transformed microorganisms and a method for production of glycerol and 1,3-propanediol with advantages derived from expressing exogenous activities of one or both of glycerol-3-phosphate dehydrogenase and glycerol-3-phosphate phosphatase while disrupting one or both of endogenous activities glycerol kinase and glycerol dehydrogenase.

U.S. Pat. No. 6,013,494 describes a process for the production of 1,3-propanediol using a single microorganism comprising exogenous glycerol-3-phosphate dehydrogenase, glycerol-3-phosphate phosphatase, dehydratase, and 1,3-propanediol oxidoreductase (e.g., dhaT). U.S. Pat. No. 6,136,576 discloses a method for the production of 1,3-propanediol comprising a recombinant microorganism further comprising a dehydratase and protein X (later identified as being a dehydratase reactivation factor peptide).

U.S. Pat. No. 6,514,733 describes an improvement to the process where a significant increase in titer (grams product per liter) is obtained by virtue of a non-specific catalytic activity (distinguished from 1,3-propanediol oxidoreductase encoded by dhaT) to convert 3-hydroxypropionaldehyde to 1,3-propanediol. Additionally, U.S. Pat. No. 7,132,527 discloses vectors and plasmids useful for the production of 1,3-propanediol.

Increased production of 1,3-propanediol may be achieved by further modifications to a host bacterium, including down-regulating expression of some target genes and up-regulating, expression of other target genes, as described in U.S. Pat. No. 7,371,558. For utilization of glucose as a carbon source in a PTS minus host, expression of glucokinase activity may be increased.

Additional genes whose increased or up-regulated expression increases 1,3-propanediol production include genes encoding:

phosphoenolpyruvate carboxylase typically characterized as EC 4.1.1.31 cob(I)alamin adenosyltransferase, typically characterized as EC 2.5.1.17 non-specific catalytic activity that is sufficient to catalyze the interconversion of 3-HPA and 1,3-propanediol, and specifically excludes 1,3-propanediol oxidoreductase (s), typically these enzymes are alcohol dehydrogenases Genes whose reduced or down-regulated expression increases 1,3-propanediol production include genes encoding:

aerobic respiration control protein
methylglyoxal synthase
acetate kinase
phosphotransacetylase
aldehyde dehydrogenase A
aldehyde dehydrogenase B
triosephosphate isomerase
phosphogluconate dehydratase In another embodiment, the recombinant bacteria disclosed herein are capable of producing 3-hydroxypropionic acid. 3-Hydroxypropionic acid has utility for specialty synthesis and can be converted to commercially important intermediates by known art in the chemical industry, e.g., acrylic acid by dehydration, malonic acid by oxidation, esters by esterification reactions with alcohols, and 1,3-propanediol by reduction. 3-Hydroxypropionic acid may be produced biologically from a fermentable carbon source by a single microorganism, as described in copending and commonly owned U.S. patent application Ser. No. 12/815,461. In one representative biosynthetic pathway, a carbon substrate is converted to 3-hydroxypropionaldehyde, as described above for the production of 1,3-propanediol. The 3-hydroxypropionaldehyde is converted to 3-hydroxypropionic acid by an aldehyde dehydrogenase. Suitable examples of aldehyde dehydrogenases include, but are not limited to, AldB (SEQ ID NO:16), encoded by the E. coli gene aldB (coding sequence set forth in SEQ ID NO:15); AldA (SEQ ID NO:18), encoded by the E. coli gene aldA (coding sequence set forth in SEQ ID NO:17); and AldH (SEQ ID NO:20), encoded by the E. coli gene aldH (coding sequence asset forth in SEQ ID NO:19).

Many of the modifications described above to improve 1,3-propanediol production by a recombinant bacterium can also be made to improve 3-hydroxypropionic acid production. For example, the elimination of glycerol kinase prevents glycerol, formed from G3P by the action of G3P phosphatase, from being re-converted to G3P at the expense of ATP. Also, the elimination of glycerol dehydrogenase (for example, gldA) prevents glycerol, formed from DHAP by the action of NAD-dependent glycerol-3-phosphate dehydrogenase, from being converted to dihydroxyacetone. Mutations can be directed toward a structural gene so as to impair or improve the activity of an enzymatic activity or can be directed toward a regulatory gene, including promoter regions and ribosome binding sites, so as to modulate the expression level of an enzymatic activity.

Up-regulation or down-regulation may be achieved by a variety of methods which are known to those skilled in the art. It is well understood that up-regulation or down-regulation of a gene refers to an alteration in the level of activity present in a cell that is derived from the protein encoded by that gene relative to a control level of activity, for example, by the activity of the protein encoded by the corresponding (or non-altered) wild-type gene.

Specific genes involved in an enzyme pathway may be up-regulated to increase the activity of their encoded function(s). For example, additional copies of selected genes may be introduced into the host cell on multicopy plasmids such as pBR322. Such genes may also be integrated into the chromosome with appropriate regulatory sequences that result in increased activity of their encoded functions. The target genes may be modified so as to be under the control of non-native promoters or altered native promoters. Endogenous promoters can be altered in vivo by mutation, deletion, and/or substitution.

Alternatively, it may be useful to reduce or eliminate the expression of certain genes relative to a given activity level. Methods of down-regulating (disrupting) genes are known to those of skill in the art.

Down-regulation can occur by deletion, insertion, or alteration of coding regions and/or regulatory (promoter) regions. Specific down regulations may be obtained by random mutation followed by screening or selection, or, where the gene sequence is known, by direct intervention by molecular biology methods known to those skilled in the art. A particularly useful, but not exclusive, method to effect down-regulation is to alter promoter strength.

Furthermore, down-regulation of gene expression may be used to either prevent expression of the protein of interest or result in the expression of a protein that is non-functional. This may be accomplished for example, by 1) deleting coding regions and/or regulatory (promoter) regions, 2) inserting exogenous nucleic acid sequences into coding regions and/or regulatory (promoter) regions, and 3) altering coding regions and/or regulatory (promoter) regions (for example, by making DNA base pair changes). Specific disruptions may be obtained by random mutation followed by screening or selection, or, in cases where the gene sequences in known, specific disruptions may be obtained by direct intervention using molecular biology methods know to those skilled in the art. A particularly useful method is the deletion of significant amounts of coding regions and/or regulatory (promoter) regions.

Methods of altering recombinant protein expression are known to those skilled in the art, and are discussed in part in Baneyx, Curr. Opin. Biotechnol. (1999) 10:411; Ross, et al., J. Bacteriol. (1998) 180:5375; deHaseth, et al., J. Bacteriol. (1998) 180:3019; Smolke and Keasling, Biotechnol. Bioeng. (2002) 80:762; Swartz, Curr. Opin. Biotech. (2001) 12:195; and Ma, et al., J. Bacteriol. (2002) 184:5733.

Recombinant bacteria containing the necessary changes in gene expression for metabolizing sucrose in the production of microbial products including glycerol and glycerol derivatives, as described above, may be constructed using techniques well known in the art, some of which are exemplified in the Examples herein.

The construction of the recombinant bacteria disclosed herein may be accomplished using a variety of vectors and transformation and expression cassettes suitable for the cloning, transformation and expression of coding regions that confer the ability to utilize sucrose in the production of glycerol and its derivatives in a suitable host microorganism. Suitable vectors are those which are compatible with the bacterium employed. Suitable vectors can be derived, for example, from a bacterium, a virus (such as bacteriophage T7 or a M-13 derived phage), a cosmid, a yeast or a plant. Protocols for obtaining and using such vectors are known to those skilled in the art (Sambrook et al., supra).

Initiation control regions, or promoters, which are useful to drive expression of coding regions for the instant invention in the desired host bacterium are numerous and familiar to those skilled in the art. Virtually any promoter capable of driving expression is suitable for use herein. For example, any of the promoters listed above may be used.

Termination control regions may also be derived from various genes native to the preferred hosts. Optionally, a termination site may be unnecessary; however, it is most preferred if included.

For effective expression of the instant polypeptides, nucleotide sequences encoding the polypeptides are linked operably through initiation codons to selected expression control regions such that expression results in the formation of the appropriate messenger RNA.

Particularly useful are the vectors pSYCO101, pSYCO103, pSYCO106, and pSYCO109, described in U.S. Pat. No. 7,371,558, and pSYCO400/AGRO, described in U.S. Pat. No. 7,524,660. The essential elements of these vectors are derived from the dha regulon isolated from Klebsiella pneumoniae and from Saccharomyces cerevisiae. Each vector contains the open reading frames dhaB1, dhaB2, dhaB3, dhaX (coding sequence set forth in SEQ ID NO:49;

encoded polypeptide sequence set forth in SEQ ID NO:50), orfX, DAR1, and GPP2 arranged in three separate operons. The nucleotide sequences of pSYCO101, pSYCO103, pSYCO106, pSYCO109, and pSYCO400/AGRO are set forth in SEQ ID NO:51, SEQ ID NO:52, SEQ ID NO:53, SEQ ID NO:54, and SEQ ID NO:55, respectively. The differences between the vectors are illustrated in the chart below [the prefix "p-" indicates a promoter; the open reading frames contained within each "( )" represent the composition of an operon]:

pSYCO101 (SEQ ID NO:51):
    p-trc (Dar1_GPP2) in opposite orientation compared to the other 2 pathway operons,
    p-1.6 long GI (dhaB1_dhaB2_dhaB3_dhaX), and
    p-1.6 long GI (orfY_orfX_orfW).

pSYCO103 (SEQ ID NO:52):
    p-trc (Dar1_GPP2) same orientation compared to the other 2 pathway operons,
    p-1.5 long GI (dhaB1_dhaB2_dhaB3_dhaX), and
    p-1.5 long GI (orfY_orfX_orfW).

pSYCO106 (SEQ ID NO:53):
    p-trc (Dar1_GPP2) same orientation compared to the other 2 pathway operons,
    p-1.6 long GI (dhaB1_dhaB2_dhaB3_dhaX), and
    p-1.6 long GI (orfY_orfX_orfW).

pSYCO109 (SEQ ID NO:54):
    p-trc (Dar1_GPP2) same orientation compared to the other 2 pathway operons,
    p-1.6 long GI (dhaB1_dhaB2_dhaB3_dhaX), and
    p-1.6 long GI (orfY_orfX).

pSYCO400/AGRO (SEQ ID NO:55):
    p-trc (Dar1_GPP2) same orientation compared to the other 2 pathway operons,
    p-1.6 long GI (dhaB1_dhaB2_dhaB3_dhaX), and
    p-1.6 long GI (orfY_orfX).
    p-1.20 short/long GI (scrK) opposite orientation compared to the pathway operons.

Once suitable expression cassettes are constructed, they are used to transform appropriate host bacteria. Introduction of the cassette containing the coding regions into the host bacterium may be accomplished by known procedures such as by transformation (e.g., using calcium-permeabilized cells, or electroporation) or by transfection using a recombinant phage virus (Sambrook et al., supra). Expression cassettes may be maintained on a stable plasmid in a host cell. In addition, expression cassettes may be integrated into the genome of the host bacterium through homologous or random recombination using vectors and methods well known to those skilled in the art. Site-specific recombination systems may also be used for genomic integration of expression cassettes.

In addition to the cells exemplified, cells having single or multiple mutations specifically designed to enhance the production of microbial products including glycerol and/or its derivatives may also be used. Cells that normally divert a carbon feed stock into non-productive pathways, or that exhibit significant catabolite repression may be mutated to avoid these phenotypic deficiencies.

Methods of creating mutants are common and well known in the art. A summary of some methods is presented in U.S. Pat. No. 7,371,558. Specific methods for creating mutants using radiation or chemical agents are well documented in the art. See, for example, Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.* 36, 227 (1992).

After mutagenesis has occurred, mutants having the desired phenotype may be selected by a variety of methods. Random screening is most common where the mutagenized cells are selected for the ability to produce the desired product or intermediate. Alternatively, selective isolation of mutants can be performed by growing a mutagenized population on selective media where only resistant colonies can develop. Methods of mutant selection are highly developed and well known in the art of industrial microbiology. See, for example, Brock, Supra; DeMancilha et al., *Food Chem.* 14, 313 (1984).

Fermentation media in the present invention comprise sucrose as a carbon substrate. Other carbon substrates such as glucose and fructose may also be present.

In addition to the carbon substrate, a suitable fermentation medium contains, for example, suitable minerals, salts, cofactors, buffers and other components, known to those skilled in the art, suitable for the growth of the cultures and promotion of the enzymatic pathway necessary for production of glycerol and its derivatives, for example 1,3-propanediol. Particular attention is given to Co(II) salts and/or vitamin $B_{12}$ or precursors thereof in production of 1,3-propanediol.

Adenosyl-cobalamin (coenzyme $B_{12}$) is an important cofactor for dehydratase activity. Synthesis of coenzyme $B_{12}$ is found in prokaryotes, some of which are able to synthesize the compound de novo, for example, *Escherichia blattae*, *Klebsiella* species, *Citrobacter* species, and *Clostridium* species, while others can perform partial reactions. *E. coli*, for example, cannot fabricate the corrin ring structure, but is able to catalyze the conversion of cobinamide to corrinoid and can introduce the 5'-deoxyadenosyl group. Thus, it is known in the art that a coenzyme $B_{12}$ precursor, such as vitamin $B_{12}$, needs be provided in *E. coli* fermentations. Vitamin $B_{12}$ may be added continuously to *E. coli* fermentations at a constant rate or staged as to coincide with the generation of cell mass, or may be added in single or multiple bolus additions.

Although vitamin $B_{12}$ is added to the transformed *E. coli* described herein, it is contemplated that other bacteria, capable of de novo vitamin $B_{12}$ biosynthesis will also be suitable production cells and the addition of vitamin $B_{12}$ to these bacteria will be unnecessary.

Typically bacterial cells are grown at 25 to 40° C. in an appropriate medium containing sucrose. Examples of suitable growth media for use herein are common commercially prepared media such as Luria Bertani (LB) broth, Sabouraud Dextrose (SD) broth or Yeast medium (YM) broth. Other defined or synthetic growth media may also be used, and the appropriate medium for growth of the particular bacterium will be known by someone skilled in the art of microbiology or fermentation science. The use of agents known to modulate catabolite repression directly or indirectly, e.g., cyclic adenosine 2':3'-monophosphate, may also be incorporated into the reaction media. Similarly, the use of agents known to modulate enzymatic activities (e.g., methyl viologen) that lead to enhancement of 1,3-propanediol production may be used in conjunction with or as an alternative to genetic manipulations with 1,3-propanediol production strains.

Suitable pH ranges for the fermentation are between pH 5.0 to pH 9.0, where pH 6.0 to pH 8.0 is typical as the initial condition.

Reactions may be performed under aerobic, anoxic, or anaerobic conditions depending on the requirements of the recombinant bacterium. Fed-batch fermentations may be performed with carbon feed, for example, carbon substrate, limited or excess.

Batch fermentation is a commonly used method. Classical batch fermentation is a closed system where the composition of the medium is set at the beginning of the fermentation and is not subject to artificial alterations during the fermentation. Thus, at the beginning of the fermentation, the medium is inoculated with the desired bacterium and fermentation is permitted to occur adding nothing to the system. Typically, however, "batch" fermentation is batch with respect to the addition of carbon source, and attempts are often made at controlling factors such as pH and oxygen concentration. In batch systems, the metabolite and biomass compositions of the system change constantly up to the time the fermentation is stopped. Within batch cultures, cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable for use herein and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, supra.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems, a number of factors affecting growth can be altered continuously while the cell concentration, measured by the turbidity of the medium, is kept constant. Continuous systems strive to maintain steady state growth conditions, and thus the cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using batch, fed-batch or continuous processes and that any known mode of fermentation would be suitable. Additionally, it is contemplated that cells may be immobilized on a substrate as whole cell catalysts and subjected to fermentation conditions for production of glycerol and glycerol derivatives, such as 1,3-propanediol.

In one embodiment, a process for making glycerol, 1,3-propanediol, and/or 3-hydroxypropionic acid from sucrose is provided. The process comprises the steps of culturing a recombinant bacterium, as described above, in the presence of sucrose, and optionally recovering the glycerol, 1,3-propanediol, and/or 3-hydroxypropionic acid produced. The product may be recovered using methods known in the art. For example, solids may be removed from the fermentation medium by centrifugation, filtration, decantation, or the like. Then, the product may be isolated from the fermentation medium, which has been treated to remove solids as described above, using methods such as distillation, liquid-liquid extraction, or membrane-based separation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques described in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

The meaning of abbreviations is as follows: "sec" means second(s), "min" means minute(s), "h" means hour(s), "nm" means nanometers, "μL" means microliter(s), "mL" means milliliter(s), "L" means liter(s), "mM" means millimolar, "M" means molar, "g" means gram(s), "μg" means microgram(s), "bp" means base pair(s), "kbp" means kilobase pair(s), "rpm" means revolutions per minute, "ATCC" means American Type Culture Collection, Manassas, Va.

Media and Culture Conditions:

Materials and methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials described for the growth and maintenance of bacterial cells may be obtained from Aldrich Chemicals (Milwaukee, Wis.), BD Diagnostic Systems (Sparks, Md.), Life Technologies (Rockville, Md.), New England Biolabs (Beverly, Mass.), or Sigma Chemical Company (St. Louis, Mo.), unless otherwise specified.

LB (Luria Bertani) medium contains following per liter of medium: Bacto-tryptone (10 g), Bacto-yeast extract (5 g), and NaCl (10 g). Supplements were added as described in the Examples below. All additions were pre-sterilized before they were added to the medium.

Molecular Biology Techniques:

Restriction enzyme digestions, ligations, transformations, and methods for agarose gel electrophoresis were performed as described in Sambrook, J., et al., *Molecular Cloning: A Laboratory Manual*, Second Edition, Cold Spring Harbor Laboratory Press (1989). Polymerase Chain Reactions (PCR)

techniques were found in White, B., *PCR Protocols: Current Methods and Applications*, Volume 15 (1993), Humana Press Inc., New York. N.Y.

Example 1

Recombinant *E. coli* Containing Putative Sucrose Metabolism Genes

The purpose of this Example was to construct a recombinant *E. coli* strain containing putative sucrose metabolism genes from *Bacillus licheniformis* ATCC® 14580, and having the ability to produce 1,3-propanediol (PDO) from sucrose.

*B. licheniformis* ATCC® 14580 genes fruP (coding sequence set forth in SEQ ID NO:23) and fruA (coding sequence set forth in SEQ ID N0:25), which are adjacent genes, were obtained by PCR amplification using a high fidelity polymerase, Phusion™ Flash (Finnzymes Oy, Espoo, Finland) using the following conditions: 98° C./10 sec; 30 cycles of 98° C./1 sec, 63° C./30 sec and 72° C./30 sec; and then 72° C./5 min using genomic DNA from *Bacillus licheniformis* ATCC® 14580 as template and the primers set forth in SEQ ID NO:56 and SEQ ID NO:57.

An adenosine nucleotide ("A") was added to the 3' ends of the 2741 bp PCR product with Taq polymerase for 10 min at 72° C. The PCR product was cloned into pBAD-TOPO® (Invitrogen, Carlsbad, Calif.) following the protocol supplied by the vendor. After transformation of *E. coli* strain TOP10 (Invitrogen) with selection for ampicillin resistance, plasmid DNA was isolated. The presence of the inserted DNA was verified by DNA sequence analysis. Two plasmids were retained and named "pBAD-TOPO *B. lichen* cscB&A 3a" and "pBAD-TOPO *B. lichen* cscB&A 3d". Plasmid pBAD-TOPO *B. lichen* cscB&A 3a was transformed into *E. coli* strain TTab pSYCO400/AGRO to generate strain PD02238. A control plasmid without inserted DNA, named "pBAD-TOPO ctl 3-8", was also transformed into *E. coli* strain TTab pSYCO400/AGRO to generate strain PD02242.

*E. coli* strain TTab pSYCO400/AGRO, a PTS minus strain, was constructed as follows. Strain TTab was generated by deletion of the aldB gene from strain TT aldA, described in U.S. Pat. No. 7,371,558 (Example 17). Briefly, an aldB deletion was made by first replacing 1.5 kbp of the coding region of aldB in *E. coli* strain MG1655 with the FRT-CmR-FRT cassette of the pKD3 plasmid (Datsenko and Wanner, *Proc. Natl. Acad. Sci. USA* 97:6640-6645, 2000). A replacement cassette was amplified with the primer pair SEQ ID NO:58 and SEQ ID NO:59 using pKD3 as the template. The primer SEQ ID NO:58 contains 80 bp of homology to the 5'-end of aldB and 20 bp of homology to pKD3. Primer SEQ ID NO:59 contains 80 bp of homology to the 3' end of aldB and 20 bp homology to pKD3. The PCR products were gel-purified and electroporated into MG1655/pKD46 competent cells (U.S. Pat. No. 7,371,558). Recombinant strains were selected on LB plates with 12.5 mg/L of chloramphenicol. The deletion of the aldB gene was confirmed by PCR, using the primer pair SEQ ID NO:60 and SEQ ID NO:61. The wild-type strain gave a 1.5 kbp PCR product while the recombinant strain gave a characteristic 1.1 kbp PCR product. A P1 lysate was prepared and used to move the mutation to the TT aldA strain to form the TT aldAΔaldB::Cm strain. A chloramphenicol-resistant clone was checked by genomic PCR with the primer pair SEQ ID NO:60 and SEQ ID NO:61 to ensure that the mutation was present. The chloramphenicol resistance marker was removed using the FLP recombinase (Datsenko and Wanner, supra) to create TTab. Strain TTab was then transformed with pSYCO400/AGRO (set forth in SEQ ID NO:55), described in U.S. Pat. No. 7,524,660 (Example 4), to generate strain TTab pSYCO400/AGRO.

As described in the cited references, strain TTab is a derivative of *E. coli* strain FM5 (ATCC® No. 53911) containing the following modifications:

deletion of glpK, gldA, ptsHI, crr, edd, arcA, mgsA, qor, ackA, pta, aldA and aldB genes;

upregulation of galP, glk, btuR, ppc, and yqhD genes; and downregulation of gapA gene.

Plasmid pSYCO400/AGRO contains genes encoding a glycerol production pathway (DAR1 and GPP2) and genes encoding a glycerol dehydratase and associated reactivating factor (dhaB123, dhaX, orfX, orfY), as well as a gene encoding a fructokinase (scrK).

Example 2

Production of 1,3-Propanediol from Sucrose

The purpose of this Example was to demonstrate that an *E. coli* strain comprising the putative sucrose metabolism genes from *B. licheniformis* ATCC® 4580 was able to metabolize sucrose and produce 1,3-propanediol (PDO) and glycerol.

*E. coli* strains PD02238 and PD02242, described in Example 1, were grown overnight in L-Broth, Miller's Modification (Teknova, Half Moon Bay, Calif.) supplemented with 100 mg/L spectinomycin and 100 mg/L ampicillin at 33° C. These cultures were used to inoculate shake flasks at an optical density of 0.01 units measured at 550 nm in MOPS minimal medium (Teknova, Half Moon Bay, Calif.) supplemented with 10 g/L sucrose. Vitamin B12 was added to the medium to a concentration of 0.1 mg/L. The cultures were incubated at 34° C. with shaking (225 rpm) for 144 hours, after which time the concentrations of sucrose, glycerol and 1,3-propanediol (PDO) in the broth were determined by high performance liquid chromatography.

Chromatographic separation was achieved using an Aminex HPX-87P column (Bio-Rad, Hercules, Calif.) with an isocratic mobile phase of distilled-deionized water at a flow rate of 0.5 mL/min and a column temperature of 85° C. Eluted compounds were quantified by refractive index detection with reference to a standard curve prepared from commercially purchased pure compounds dissolved to known concentrations in MOPS minimal medium. Retention times were sucrose at 12.2 min, 1,3-propanediol at 17.9 min, and glycerol at 23.6 min. *E. coli* strain PD02238 with the putative sucrose metabolism genes from *B. licheniformis* ATCC® 4580 metabolized sucrose (final concentration of 8.6 g/L) and produced 0.7 g/L PDO and 0.16 g/L glycerol. The control strain PD02242 did not metabolize sucrose (final concentration of 15.4 g/L, increased concentration from the initial concentration due to evaporation) and produced no detectable PDO or glycerol under these conditions.

Example 3

Recombinant *E. coli* Containing Putative Sucrose Metabolism Genes

The purpose of this Example was to construct a recombinant *E. coli* strain containing cloned sucrose metabolism genes from *Bacillus licheniformis* ATCC® 14580.

The origin of replication of the large native plasmid pMT100, described in U.S. Patent Application Publication No. 2008/0194032, from *E. coli* strain ATCC® 13281, was amplified by PCR using primers MTori1, set forth in SEQ ID NO:62, and MTori2, set forth in SEQ ID NO:63. A HindIII restriction enzyme recognition site was present in one of the PCR primers. The resulting PCR product was digested with the restriction enzymes DraI and HindIII and ligated to the SspI/HindIII fragment of pK194, described by Jobling and Holmes (*Nucleic Acids Res.* 18:5315, 1990), that contains a multiple cloning site and a kanamycin resistance gene. The resulting plasmid was named pMTori. To make plasmids pMTP1.20 and pMTP1.5, the EcoRI/HindIII fragment from pMTori1 was replaced with the EcoRI/HindIII fragment from the respective pMP38 plasmid, described in U.S. Pat. No. 7,132,527. The designations "1.20" and "1.5" refer to the variants of the glucose isomerase promoter described in U.S. Pat. No. 7,132,527.

The plasmid pBAD-TOPO *B. lichen* cscB&A 3d, described in Example 1, was digested with HpaI and a resulting 2.7 kbp fragment containing *Bacillus licheniformis* ATCC® 14580 genes fruP and fruA was isolated. Plasmids pMTP1.20 and pMTP1.5 were each digested with HpaI to linearize them and were then treated with calf intestinal alkaline phosphatase. The 2.7 kbp band from pBAD-TOPO *B. lichen* cscB&A 3d was ligated to the linearized pMTP1.20 or pMTP1.5 and the ligation mixes were used to transform *E. coli* TOP10 (Invitrogen) with selection for kanamycin resistance. Transformant colonies were picked and patched to agar plates made with Difco™ MacConkey agar base (Becton, Dickinson and Company, Sparks, Md.) containing 10 g/L sucrose and 25 μg/mL kanamycin, and transformants that resulted in pink growth, indicating fermentation of sucrose, were retained. Plasmid DNA was isolated, and DNA sequence analysis confirmed that the *Bacillus licheniformis* ATCC® 14580 genes fruP and fruA were present and oriented such that they would be expressed from the P1.20 promoter in a plasmid named "pMTP1.20cscB&A(*B. lichen*)-2" or from the P1.5 promoter in a plasmid named "pMTP1.5cscB&A(*B. lichen*)-1".

Plasmids pMTP1.20cscB&A(*B. lichen*)-2 and pMTP1.5cscB&A(*B. lichen*)-1 were transformed into *E. coli* strain FM5 (ATCC® 53911) to generate strains PD02487 and PD02489, respectively. Plasmids pMTP1.20 or pMTP1.5 without inserted DNA were also transformed into *E. coli* strain FM5 to generate strains PD02263 and PD02122, respectively.

*E. coli* strains PD02487, PD02489, PD02263 and PD02122 were grown overnight in LB (Luria Bertani) medium containing 25 μg/mL kanamycin at 37° C. The next day, these cultures were diluted 1:100 in the wells of a Bioscreen-C plate (instrument and plates purchased from Growth Curves USA, Piscataway N.J.) with MOPS minimal medium (Teknova, Half Moon Bay, Calif.) containing 10 g/L sucrose. The cultures were grown at 37° C. in triplicate with continuous shaking and the optical density was monitored. At 50 hours after inoculation, the optical density of the PD02487 culture was 0.188+/−0.003 and the optical density of the PD02489 culture was 0.272+/−0.016. In contrast, the optical density of the control cultures without sucrose metabolism genes were 0.043+/−0.008 for strain PD02263 and 0.031+/−0.003 for strain PD02122. These results demonstrate that the control strains were unable to grow with sucrose as sole carbon source, while the strains expressing *Bacillus licheniformis* ATCC® 14580 genes fruP and fruA were able to grow with sucrose as sole carbon source.

What is claimed is:

1. A recombinant bacterium comprising in its genome or on at least one recombinant construct:
   (a) a nucleotide sequence encoding a polypeptide having sucrose transporter activity, said polypeptide having at least 95% sequence identity to the amino acid sequence of SEQ ID NO:24, based on a Clustal V method of alignment; and
   (b) a nucleotide sequence encoding a polypeptide having sucrose hydrolase activity, said polypeptide having at least 95% sequence identity to the amino acid sequence of SEQ ID NO:26, based on a Clustal V method of alignment;
   wherein (a) and (b) are each operably linked to the same or a different promoter, wherein said recombinant bacterium has the ability to metabolize sucrose and wherein the recombinant bacterium produces 1,3-propanediol, glycerol, and/or 3-hydroxypropionic acid.

2. The recombinant bacterium of claim 1, wherein the nucleotide sequence encoding the polypeptide having sucrose transporter activity has at least 95% sequence identity to the nucleotide sequence of SEQ ID NO:23, based on BLASTN method of alignment.

3. The recombinant bacterium of claim 1, wherein the nucleotide sequence encoding the polypeptide having sucrose hydrolase activity has at least 95% sequence identity to the nucleotide sequence of SEQ ID NO:25, based on BLASTN method of alignment.

4. The recombinant bacterium of claim 1, further comprising in its genome or on at least one recombinant construct, a nucleotide sequence encoding a polypeptide having fructokinase activity.

5. The recombinant bacterium of claim 4, wherein the polypeptide having fructokinase activity has at least 95% sequence identity to the amino acid sequence of SEQ ID NO:32, SEQ ID NO:34, SEQ ID NO:36, SEQ ID NO:38, SEQ ID NO:40, SEQ ID NO:42, SEQ ID NO:44, or SEQ ID NO:46, based on the Clustal V method of alignment.

6. The recombinant bacterium of claim 4, wherein the polypeptide having fructokinase activity has the amino acid sequence of SEQ ID NO:40.

7. The recombinant bacterium of claim 1, wherein said bacterium is selected from the group consisting of the genera: *Escherichia*, *Klebsiella*, *Citrobacter*, and *Aerobacter*.

8. The recombinant bacterium of claim 7, wherein said bacterium is *Escherichia coli*.

9. A process for making glycerol, 1,3-propanediol and/or 3-hydroxypropionic acid from sucrose comprising:
   a) culturing the recombinant bacterium of claim 1 in the presence of sucrose;
   and b) recovering the glycerol, 1,3-propanediol and/or 3-hydroxypropionic acid produced.

\* \* \* \* \*